: US009828407B2

(12) United States Patent
Auriol et al.

(10) Patent No.: US 9,828,407 B2
(45) Date of Patent: Nov. 28, 2017

(54) WATER SOLUBLE AND ACTIVABLE PHENOLIC DERIVATIVES WITH DERMOCOSMETIC AND THERAPEUTIC APPLICATIONS AND PROCESS FOR PREPARING SAID DERIVATIVES

(71) Applicant: LIBRAGEN, Toulouse (FR)

(72) Inventors: Daniel Auriol, Toulouse (FR); Renaud Nalin, Dremil-Lafage (FR); Patrick Robe, Odars (FR); Fabrice Lefevre, Auterive (FR)

(73) Assignee: LIBRAGEN, Toulouse (FR)

( * ) Notice: Subject to any disclaimer, the term of this patent is extended or adjusted under 35 U.S.C. 154(b) by 540 days.

(21) Appl. No.: 14/084,793

(22) Filed: Nov. 20, 2013

(65) Prior Publication Data

US 2014/0088030 A1    Mar. 27, 2014

Related U.S. Application Data

(60) Division of application No. 13/052,633, filed on Mar. 21, 2011, now abandoned, which is a continuation of application No. 12/304,212, filed as application No. PCT/EP2007/055815 on Jun. 13, 2007, now abandoned.

(30) Foreign Application Priority Data

Jun. 14, 2006  (EP) .................................... 06290972

(51) Int. Cl.
| | |
|---|---|
| *C12P 19/44* | (2006.01) |
| *C07H 17/075* | (2006.01) |
| *C12P 17/02* | (2006.01) |
| *C12P 19/02* | (2006.01) |
| *C07H 15/203* | (2006.01) |
| *C07H 15/24* | (2006.01) |
| *C07H 15/26* | (2006.01) |
| *C12P 19/60* | (2006.01) |

(52) U.S. Cl.
CPC ......... *C07H 17/075* (2013.01); *C07H 15/203* (2013.01); *C07H 15/24* (2013.01); *C07H 15/26* (2013.01); *C12P 17/02* (2013.01); *C12P 19/02* (2013.01); *C12P 19/44* (2013.01); *C12P 19/60* (2013.01)

(58) Field of Classification Search
CPC .... C07H 17/075; C07H 15/26; C07H 15/203; C07H 15/24; C12P 19/60; C12P 19/44
See application file for complete search history.

(56) References Cited

U.S. PATENT DOCUMENTS

| | | | | |
|---|---|---|---|---|
| 4,968,438 A | * | 11/1990 | Soderquist ............ | C23F 11/124 210/750 |
| 2005/0272921 A1 | * | 12/2005 | Furuya .................. | A61K 8/602 536/18.6 |

OTHER PUBLICATIONS

Kitao, S. et al., Biosci. Biotech. Biochem., "alpha-D-Glucosyl Transfer to Phenolic Compounds by Sucrose Phosphorylase from Leuconostoc mesenteroides and Production of alpha-Arbutin", 1994, vol. 58, No. 1, pp. 38-42.*
Lim, E. et al. "Regioselectivity of glucosylation of caffeic acid by a UDP-glucose: glucosyltransferase is maintained in planta" *Biochemical Journal*, 2003, pp. 987-992, vol. 373, XP-002276051.
Bae, C. et al. "Microbial Approach to the Regioselective Glycosylation of Hydroxytyrosol" *Journal of the Korean Chemical Society*, 2004, pp. 111-114, vol. 48, No. 1, XP-002525761.
Braun, D. et al. "Glucoside derivatives as novel photostabilizers for rigid PVC" *Die Angewandte Makromolekulare Chemie*, 1999, pp. 93-100, vol. 271, XP-000878315.
Bertrand, A. et al. "*Leuconostoc mesenteroides* glucansucrase synthesis of flavonoid glucosides by acceptor reactions in aqueous-organic solvents" *Carbohydrate Research*, 2006, pp. 855-863, vol. 341.
Meulenbeld, G. H. et al. "Enhanced (+)-Catechin Transglucosylating Activity of Streptococcus mutans GS-5 Glucosyltransferase-D due to Fructose Removal" *Applied Environmental Microbiology*, Sep. 1999, pp. 4141-4147, vol. 65, No. 9, XP-002410550.
Kumarasamy, Y. et al. "The Assessment of Biological Activities Associated with the Major Constituents of the Methanol Extract of 'Wild Carrot' (*Daucus carota* L.) Seeds" *Journal of Herbal Pharmacotherapy*, 2005, pp. 61-72, vol. 5, No. 1, XP-008072520.
Sato, T. et al. "α-Anomer-Selective Glucosylation of (+)-Catechin by the Crude Enzyme, Showing Glucosyl Transfer Activity, of *Xanthomonas campestris* WU-9701" *Journal of Bioscience and Bioengineering*, 2000, pp. 625-630, vol. 90, No. 6, XP-002525762.
Brignolas, F. et al. "Induced Responses in Phenolic Metabolism in Two Norway Spruce Clones after Wounding and Inoculations with *Ophiostoma polonicum*, a Bark Beetle-Associated Fungus" *Plant Physiol.*, 1995, pp. 821-827, vol. 109, XP-002424933.
Nanjo, F. et al. "Radical Scavenging Activity of Tea Catechins and Their Related Compounds" *Bioscience, Biotechnology and Biochemistry*, 1999, pp. 1621-1623, vol. 63, No. 9.
Moon, Y.-H. et al. "Synthesis, Structure Analyses, and Characterization of Novel Epigallocatechin Gallate (EGCG) Glycosides Using the Glucansucrase from *Leuconostoc mesenteroides* B-1299CB" *Journal of Agricultural and Food Chemistry*, Jan. 2006, pp. 1230-1237, vol. 54, No. 4.

(Continued)

*Primary Examiner* — Eric Olson
*Assistant Examiner* — Bahar Craigo
(74) *Attorney, Agent, or Firm* — Saliwanchik, Lloyd & Eisenschenk

(57) ABSTRACT

The invention relates to the preparation of phenolic derivatives by enzymatic condensation of phenolics selected among pyrocatechol or its derivatives with the glucose moiety of sucrose. The production of said phenolic derivatives is achieved with a glucosyltransferase (EC 2.4.1.5). These O-α-glucosides of selected phenolics are new, have a solubility in water higher than that of their parent polyphenol and have useful applications in cosmetic and pharmaceutical compositions, such as antioxidative, antiviral, antibacterial, immune-stimulating, antiallergic, antihypertensive, anti-ischemic, antiarrythmic, antithrombotic, hypocholesterolemic, antilipoperoxidant, hepatoprotective, anti-inflammatory, anticarcinogenic, antimutagenic, antineoplastic, anti-thrombotic and vasodilatory formulations, or in any other field of application.

18 Claims, 17 Drawing Sheets

(56) References Cited

OTHER PUBLICATIONS

Remington, *The Science and Practice of Pharmacy*, 20$^{th}$ Edition, Lippincott Williams & Wilkins, 2000, pp. 218-220.
Van Well, R.M. et al. "Iodine Promoted Glycosylation with Glycosyl Iodides: α-Glycoside Synthesis" *Journal of Carbohydrate Chemistry*, 2005, pp. 463-474, vol. 24.
Van Rensburg, H. et al. "Enantioselective Synthesis of the Four Catechin Diastereomer Derivatives" *Tetrahedron Letters*, 1997, pp. 3089-3092, vol. 38, No. 17.
Satake, T. et al. "Studies on the Constituents of Fruits of *Helicteres isora* L." *Chem. Pharm. Bull.*, Oct. 1999, pp. 1444-1447, vol. 47, No. 10.
Vogelsang, K. et al. "Production of rosmarinic acid and a new rosmarinic acid 3'-0-β-$_D$-glucoside in suspension cultures of the hornwort *Anthoceros agrestis* Paton" *Planta*, 2006, pp. 369-373, vol. 223.
Du, Y. et al. "Total Synthesis of Quercetin 3-Sophorotrioside" *J. Org. Chem.*, 2004, pp. 2206-2209, vol. 69.
Du, Y. et al. "The first total synthesis of calabricoside A" *Tetrahedron Letters*, 2003, pp. 6887-6890, vol. 44.
Le Claire, E. et al. "Distribution of a New Rosmarinic Acid Derivative in *Eryngium alpinum* L. and Other Apiaceae" *Journal of Agricultural and Food Chemistry*, 2005, pp. 4367-4372, vol. 53.

\* cited by examiner

Verbascoside O-α-D-glucoside

Hamamelitannin glucoside

Gossypetin glucoside

Homoorientin glucoside

Orientin glucoside

Eriodictyol chalcone glucoside

Maritimein glucoside

Salsolinol glucoside 3,4-dihydroxyacetophenone glucoside

WATER SOLUBLE AND ACTIVABLE PHENOLIC DERIVATIVES WITH DERMOCOSMETIC AND THERAPEUTIC APPLICATIONS AND PROCESS FOR PREPARING SAID DERIVATIVES

CROSS-REFERENCE TO RELATED APPLICATIONS

This application is a divisional of U.S. application Ser. No. 13/052,633, filed Mar. 21, 2011, which is a continuation of U.S. application Ser. No. 12/304,212, filed Dec. 10, 2008, now abandoned, which is the U.S. national stage application of International Patent Application No. PCT/EP2007/055815, filed Jun. 13, 2007, the disclosures of which are hereby incorporated by reference in their entireties, including all figures, tables and amino acid or nucleic acid sequences.

FIELD OF THE INVENTION

The present invention relates to the preparation of phenolic derivatives, pharmaceutical and cosmetic compositions comprising such phenolic derivatives, and their use for the beauty of the skin and for treating diseases.

BACKGROUND OF THE INVENTION

Phenolic Compounds and their Properties

Phenolic compounds (also called phenolics), or polyphenols, constitute one of the most numerous and widely-distributed groups of substances in the plant kingdom, with more than 8,000 phenolic structures currently known. Polyphenols are products of the secondary metabolism of plants. The expression "phenolic compounds" embraces a considerable range of substances that possess an aromatic ring bearing one or more hydroxyl substituents. Most of the major classes of plant polyphenol are listed in Table 1, according to the number of carbon atoms of the basic skeleton. The structure of natural polyphenols varies from simple molecules, such as phenolic acids, to highly polymerized compounds, such as condensed tannins (HARBORNE J B (1980) Plant phenolics. In: BELL E A, CHARLWOOD BV (eds) Encyclopaedia of Plant Physiology, volume 8 Secondary Plant Products, Springer-Verlag, Berlin Heidelberg New York. Pp: 329-395).

The three important groups for humans are phenolic acids (C6-C1, C6-C2 and C6-C3), flavonoids (C6-C3-C6) and high-molecular-weight polyphenols (more than 30 carbon atoms). Indeed, the phenolics, particularly polyphenols, exhibit a wide variety of beneficial biological activities in mammals, including antiviral, antibacterial, immune-stimulating, antiallergic, antihypertensive, anti-ischemic, antiarrhythmic, antithrombotic, hypocholesterolemic, antilipoperoxidant, hepatoprotective, anti-inflammatory, anticarcinogenic, antimutagenic, antineoplastic, anti-thrombotic and vasodilatory actions. They are powerful antioxidants in vitro.

TABLE I

The major classes of phenolic compounds (or phenolics) in plants (HARBORNE JB, 1980)

| NUMBER OF CARBON ATOMS | BASIC SKELETON | CLASS | EXAMPLES |
|---|---|---|---|
| 6 | C6 | Simple phenols Benzoquinones | Catechol, hydroquinone 2,6-Dimethoxybenzoquinone |
| 7 | C6-C1 | Phenolic acids | Gallic, salicylic |
| 8 | C6-C2 | Acetophenones Tyrosine derivatives Phenylacetic acids | 3-Acetyl-6-methoxybenzaldehyde Tyrosol p-Hydroxyphenylacetic |
| 9 | C6-C3 | Hydroxycinnamic acids Phenylpropenes Coumarins Isocoumarins Chromones | Caffeic, ferulic Myristicin, eugenol Umbelliferone, aesculetin Bergenon Eugenin |
| 10 | C6-C4 | Naphthoquinones | Juglone, plumbagin |
| 13 | C6-C1-C6 | Xanthones | Mangiferin |
| 14 | C6-C2-C6 | Stilbenes Anthraquinones | Resveratrol Emodin |
| 15 | C6-C3-C6 | Flavonoids Isoflavonoids | Quercetin, cyanidin Genistein |
| 18 | (C6-C3)2 | Lignans Neolignans | Pinoresinol Eusiderin |
| 30 | (C6-C3-C6)2 | Biflavonoids | Amentoflavone |
| n | (C6-C3)n (C6)n (C6-C3-C6)n | Lignins Catechol melanins Flavolans (Condensed Tannins) | |

Among the phenolic acids, the most important constitutive carbon frameworks are the hydroxybenzoic (C6-C1) and hydroxycinnamic (C6-C3) structures. The hydroxybenzoic acid content of edible plants is generally very low, with the exception of certain red fruits, black radish and onions, which can have concentrations of several tens of milligrams per kilogram fresh weight. Hydroxybenzoic acids are components of complex structures such as hydrolyzable tannins (gallotannins in mangoes and ellagitannins in red fruits such as strawberries, raspberries and blackberries). The hydroxycinnamic acids are more common than are the hydroxybenzoic acids and consist chiefly of p-coumaric, caffeic, ferulic and sinapic acids. These acids are rarely found in the free form, except in processed food that has undergone freezing, sterilization or fermentation. The bound forms are glycosylated derivatives or esters of quinic acid, shikimic acid and tartaric acid. Caffeic acid and quinic acid combine to form chlorogenic acid, which is found in many types of fruit and in high concentration in coffee. Caffeic acid, both free and esterified, is generally the most abundant phenolic acid and represents between 75% and 100% of the total hydroxycinnamic acid of most fruit (MANACH C, SCALBERT A, MORAND C, REMESY C, JIMENEZ L (2004) Polyphenols: food sources and bioavailability. Am J Clin Nutr 79: 727-747).

The flavonoids consist of a large group of low-molecular weight polyphenolic substances, benzo-γ-pyrone derivatives, that are diverse in chemical structure; they represent the most common and widely distributed group of plant phenolics. The flavonoids' common structure is that of diphenylpropanes (C6-C3-C6); it consists of two aromatic rings (cycles A and B) linked through three carbons that usually form an oxygenated heterocycle (cycle C). FIG. 1 shows the basic structure and the system used for the carbon numbering of the flavonoid nucleus. Structural variations within the rings subdivide the flavonoids into several families: flavonols, flavones, flavanols, isoflavones, antocyanidins and others. These flavonoids often occur as glycosides, glycosylation rendering the molecule more water-soluble and less reactive toward free radicals. The sugar most commonly involved in glycoside formation is glucose, although galactose, rhamnose, xylose and arabinose also occur, as well as disaccharides such as rutinose. The flavonoid variants are all related by a common biosynthetic pathway, incorporating precursors from both the shikimate and the acetate-malonate pathways (CROZIER A, BURNS J, AZIZ A A, STEWART A J, RABIASZ H S, JENKINS G I, EDWARDS C A, LEAN MEJ (2000) Antioxidant flavonols from fruits, vegetables and beverages: measurements and bioavailability. Biol Res 33: 79-88). Further modifications occur at various stages, resulting in an alteration in the extent of hydroxylation, methylation, isoprenylation, dimerization and glycosylation (producing O- or C-glycosides). Phenolic compounds act as antioxidants with mechanisms involving both free radical scavenging and metal chelation. Indeed, excess levels of metal cations of iron, zinc and copper in the human body can promote the generation of free radicals and contribute to the oxidative damage of cell membranes and cellular DNA; by forming complexes with these reactive metal ions, they can reduce their absorption and reactivity. It has to be underlined that although most flavonoids chelate $Fe^{2+}$, there are large differences in the chelating activity. In particular, the dihydroflavonol taxifolin chelates more efficiently $Fe^{2+}$ than the corresponding flavonol quercetine (VAN ACKER SABE, VAN DEN BERG D J, TROMP MNJL, GRIFFIOEN DHG, VAN BENNEKOM, VAN DER VIJGH WJF, BAST A (1996) Structural aspects of antioxidant activity of flavonoids. Free Radic Biol Med 20: 331-342).

Flavonoids have ideal structural chemistry for free radical-scavenging activities (several studies have shown the flavonoids to act as scavengers of superoxide anions, singlet oxygen, hydroxyl radicals and lipid peroxyl radicals by rapid donation of a hydrogen atom). One important finding from the studies of the relationship between the structural characteristics of flavonoids and their antiradical activity is that a catechol moiety (3', 4'-dihydroxyphenol) on ring B is required for good scavenging activity. Recently, this statement was confirmed with, nevertheless, a modulation: in a study about the relationship between the structural characteristics of 29 flavonoids and their antiradical activity, it was indeed observed that the catechol structure in the B ring is not always a conditio sine qua non in achieving high free radical-scavenging activity and that highly active flavonoids possess a 3',4'-dihydroxy B ring and/or a 3-OH group (AMIC D, DAVIDOVIC-AMIC D, BESLO D, TRINAJSTIC N (2003) Structure-radical scavenging activity relationships of flavonoids. Croatica Chem Acta 76: 55-61). Flavonoids have been shown to be more effective antioxidants in vitro than vitamins E and C on a molar basis (RICE-EVANS C A, MILLER N J, PAGANGA G (1997) Antioxidant properties of phenolic compounds. Trends in Plant Science 2: 152-159). There are also reports of flavonoids inhibiting the activity of enzymes such as oxygenases.

It must be underlined that the hydrophobicity of polyphenols is intermediate between that of vitamin C (highly hydrophilic) and that of vitamin E (highly hydrophobic); polyphenols are thus expected to act at water-lipid interfaces and may be involved in oxidation regeneration pathways with vitamins C and E.

Phenolic Derivatives and their Preparation

Due to their low aqueous solubility and/or high sensitivity toward oxidation, the use of phenolics in pharmaceutical or cosmetic preparations requires adapted and specific formulations. Since these formulations must also satisfy the constraints associated with their final usage, the compromise between acceptability, concentration and stability is often difficult to reach.

More water-soluble and/or oxidation-resistant forms of phenolics such as the glycosides are not always available in nature and may demand, when they exist, complex procedures of extraction and purification from the plant material. Both chemical and biochemical (enzymatic) approaches have been attempted to increase water solubility and/or stability. As phenolic compounds have several free hydroxyl groups, attempts for chemical modifications of phenolic compounds lead to unselective reactions, generating a panel of different molecules. Further steps of purification are then required to recover the desired product(s).

As far as the biochemical approach is concerned, three ways have been investigated to date to obtain phenolic glycosides and basically flavonoid glycosides.

The first way relies on glycosyltransferases able to transfer the sugar moiety of a sugar nucleotide to an acceptor (in the case of UDP-glucose:glucosyltransferases (UGT), glucose is transferred from uridine 5'-diphosphoglucose). These enzymes, which contribute to the synthesis of secondary metabolism in plants, have broad acceptor substrate specificities (LIM E K, HIGGINS G S, BOWLES D J (2003) Regioselectivity of glucosylation of caffeic acid by UDP-glucose:glucosyltransferase is maintained in planta. Biochem J 373: 987-92; LIM E K, ASHFORD D A, HOU B, JACKSON R G, BOWLES D J (2004) *Arabidopsis* glycosyltransferases as biocatalysts in fermentation for regioselective synthesis of diverse quercetin glucosides. Biotechnol. Bioeng. 87(5): 623-31). Nevertheless, this approach is impaired by the very high cost of the sugar nucleotides and the regeneration of the sugar nucleotide substrate, which is a way to decrease the substrate cost, is difficult to master on a large scale.

The second way relies on saccharide-transferring enzymes able to transfer glucose from an α-glucosyl saccharide. Said enzymes are selected from the hydrolases α-glucosidase (EC 3.2.1.20) and α-amylase (EC 3.2.1.1), and from the transferase cyclodextrin-glucanotransferase (EC 2.4.1.19). Their substrates are amylose, dextrins, cyclodextrins, maltooligosaccharides and partial starch hydrolysates, all of them containing mainly or exclusively glucosyl residues linked to each other through an α 1→4 osidic bond. According to this approach, U.S. Pat. No. 5,565,435 states that α-glucosyl quercetin is obtained. It has to be underlined that the starch-degrading enzymes link the glucosyl residue to the flavonoid through an α-osidic bond whereas the UDP-glucose:glucosyltransferase investigated by LIM et al. links the glucosyl residue to the flavonoid through a β-osidic bond. It has also to be underlined that in the conditions described in U.S. Pat. No. 5,565,435, the quercetin molecule could be solubilized by adjusting the pH to 8.5 and by maintaining the reaction medium at 60° C. The solubilisation of phenolics in alkaline media is due to the formation of phenolates; in these pH and temperature conditions, the stability of the substrate was achieved by operating under anaerobic conditions. It thus appears that this mode of preparation is highly difficult to control and manage and that a simple mode of preparation should be valuable.

The third way involves glucosyltransferases using sucrose β-D-fructofuranosyl-α-D-glucopyranoside) as a glucosyl donor and producing glucans with the release of fructose. Several attempts have been achieved with this class of enzymes to try to get phenolic glucosides. First, the glucosyltransferase from *Streptococcus sobrinus* (referenced by the authors as strain 6715, serotype g) was proven to catalyze the synthesis of 4'-O-α-D-glucopyranosyl-(+)-catechin in a strictly aqueous medium (catechin at 1 g/L in 100 mM phosphate buffer pH 6.0 containing 2% sucrose) (NAKAHARA K, KONTANI M, ONO H, KOMADA T, TANAKA T, OOSHIMA T, HAMADA S (1995) Glucosyltransferase from *Streptococcus sobrinus* catalyzes glucosylation of catechin. Appl. Environ. Microbiol. 61(7): 2768-70). A similar enzyme, the glucosyltransferase-D from *Streptococcus mutans* GS-5, was proven to be less regioselective, as it catalyzes not only the synthesis of 4'-O-α-D-glucopyranosyl-(+)-catechin but also the synthesis of 7-O-α-D-glucopyranosyl-(+)-catechin and of the diglucosylated derivative 4',7-O-α-D-diglucopyranosyl-(+)-catechin (MEULENBELD G H, ZUILHOF H, VAN VELDHUIZEN A, VAN DEN HEUVEL RHH, HARTMANS S (1999) Enhanced (+)-catechin transglucosylating activity of *Streptococcus mutans* GS-5 glucosyltransferase-D due to fructose removal. Appl Environ Microbiol 65(9): 4141-7). Though several investigations regarding the acceptor specificity of *Streptococcus mutans* GS-5 glucosyltransferase lead the authors to infer that aromatic acceptors appear to require two adjacent aromatic hydroxyl groups (MEULENBELD G H, HARTMANS S (2000) Transglycosylation by *Streptococcus mutans* GS-5 glucosyltransferase-D: acceptor specificity and engineering reaction conditions. Biotechnol Bioeng 70(4): 363-9), this statement was counteracted by the identification of glucosylation at position 7 in catechin (MEULENBELD et al., 1999) and by the synthesis of non-pyrocatechol derivatives. Indeed, pinosylvin and resveratrol, respectively 3,5-dihydroxy-trans-stilbene and 3,4',5-tri hydroxy-trans-stilbene, were glucosylated by a crude glucosyltransferase preparation produced by *Streptococcus mutans* to form respectively 3-O-α-D-glucopyranosyl-(E)-pinosylvin and 3-O-α-D-glucopyranosyl-(E)-resveratrol (SHIM H, HONG W, AHN Y (2003) Enzymatic preparation of phenolic glucosides by *Streptococcus mutans*. Bull Korean Chem Soc 24(11): 1680-2). Very recently, it was claimed that the flavonols quercetin and myricetin and the flavone luteolin could be glucosylated by special glucansucrases, namely the *Leuconostoc mesenteroides* NRRL B-512F dextransucrase (sucrose: 1,6-α-D-glucan 6-α-D-glucosyltransferase, EC 2.4.1.5) and the *Leuconostoc mesenteroides* NRRL B-23192 alternansucrase (sucrose:1,6(1,3)-α-D-glucan 6(3)-α-D-glucosyltransferase, EC 2.4.1.140) (BERTRAND A, MOREL S, LEFOULON F, ROLLAND Y, MONSAN P, REMAUD-SIMEON M (2006) *Leuconostoc mesenteroides* glucansucrase synthesis of flavonoid glucosides by acceptor reactions in aqueous-organic solvents. Carbohydr Res 341: 855-63). Conventionally, in the presence of sucrose, the former produces a glucan (dextran) in which 95% of the glucosidic bonds are α-(1→6) (skeleton of the polysaccharide) and 5% α-(1→3) (branching points), and the latter a glucan (alternan) in which the glucosidic bonds are alternatively α-(1→6) and α-(1→3). The obtained flavonoid derivatives were: luteolin-3'-O-α-D-glucopyranoside, luteolin-4'-O-α-D-glucopyranoside, quercetin-3'-O-α-D-glucopyranoside, quercetin-4'-O-α-D-glucopyranoside, quercetin-3'-4'-O-α-D-diglucopyranoside, myricetin-3'-O-α-D-glucopyranoside and myricetin-4'-O-α-D-glucopyranoside. This work demonstrates that yields of glycoside derivative synthesis not only rely on the enzyme itself (the synthesis of luteolin-O-glycosides dropped down from 44% to 8% between dextransucrase and alternansucrase), but also on slight chemical differences between two acceptors (no conversion was observed with the dextransucrase on diosmetin and diosmin).

From the above significant (though not exhaustive) state of the art regarding the experimented ways to obtain glucosylated derivatives of polyphenols in general (and flavonoids in particular) in order to overcome the main conventional drawbacks of flavonoids (poor water solubility at physiological conditions, in particular at pH ranging from 5 to 7 and 30° C. and high sensitivity to autoxidation in these biological conditions), it clearly appears that no precise guidelines can be deduced to set up the enzymatic production of a specific phenolic glycoside. On the contrary, it shows that there is no way for a man of the art to predict which flavonoid can be glucosylated with which enzyme and in which conditions to obtain high glucoside concentrations (see summary in Table 2). Indeed, though attempts have been made to establish a relationship between the phenolic structures and the possibility of their use as glycosyl acceptors by glycosyltransferases, it still appears that the obtention of glycosylated phenolics strongly depends on the nature of the phenolic substance and on the enzyme used for the condensation reaction. This is particularly true with glucosyltransferases conventionally synthesizing α-D-glucans from sucrose (EC 2.4.1.5), for which only a very small number of polyphenolic structures have been successfully reported. Furthermore, in the case of the main glucosyltransferases studied, namely *S. mutans* GS-5 glucosyltransferase D and *L. mesenteroides* NRRL B-512F dextransucrase, it has to be mentioned that the former synthesizes a water-soluble α-glucan in a primer-stimulated and dependent manner (HAMADA N, KURAMITSU H K (1989) Isolation and characterization of the *Streptococcus mutans* gtfD gene, coding for primer-dependent soluble glucan synthesis. Infect Immun 56: 1999-2005) whereas the later does not (ROBYT J F, WALSETH T F (1978) the mechanism of acceptor reactions of *Leuconostoc mesenteroides* NRRL B-512F. Carbohydr Res 61: 433-45). These glucosyltransferases have distinct mechanisms of action and consequently molecules that are acceptors for an enzyme are not necessarily acceptors for another; in other words, as shown in the previously cited works, there is no justification to consider that the substances that act as glucosyl acceptors in the case of *S. mutans* GS-5 glucosyltransferase D act also as glucosyl acceptors in the case of *L. mesenteroides* NRRL B-512F dextransucrase and vice versa.

All the more, prior art information shows that despite the interest and abundance of phenolics, few phenolic glycosides have been obtained by enzymatic reactions.

TABLE 2

| POLYPHENOL | ENZYME ORIGIN | PRODUCT(S) AND REFERENCE |
|---|---|---|
| Enzymes and substrates: Glycosyltransferases able to transfer the sugar moiety of a sugar nucleotide (e.g. UDP-glucose) | | |
| Caffeic acid (OH in 3 and 4) | *Arabidopsis thaliana* | Caffeoyl-3-O-β-glucoside - LIM et al. 2003 |
| o- and m-coumaric acids (OH in 2 and 3, respectively) | *Arabidopsis thaliana* | 2-O- and 3-O-β-glucosides of o- and m-coumaric acids - LIM et al. 2003 |
| Isoferulic acid (OH in 3; $OCH_3$ in 4) | *Arabidopsis thaliana* | 3-O-β-glucoside - LIM et al. 2003 |
| p-coumaric acid (OH in 4), ferulic acid (OH in 4 and OCH3 in 3) and sinapic acid (OH in 4 and $OCH_3$ in 3 and 5) | *Arabidopsis thaliana* | No glucoside - LIM et al. 2003 |
| Quercetin (flavonol; OH in 3, 5, 7, 3' and 4') | *Arabidopsis thaliana* | 3-O-, 7-O-, 3'-O-, 4'-O-monoglucosides and 3,7-di-O and 7-3'-di-O-glucosides LIM et al. 2003; LIM et al. 2004 |
| Luteolin (flavone; OH in 5, 7, 3' and 4') | *Arabidopsis thaliana* | Glucosides - LIM et al. 2003 |
| Eriodictyol (flavanone; OH in 5, 7, 3' and 4') | *Arabidopsis thaliana* | No glucoside - LIM et al. 2003 |
| Catechin (flavanol; OH in 3, 5, 7, 3' and 4') and cyanidin (anthocyan; OH in 5, 7, 3', 4') | *Arabidopsis thaliana* | No glucoside - LIM et al. 2003 |
| Enzymes and substrates: Starch degrading enzymes (α-glucosidase, cyclodextrin glucanotransferase or CGTase, α-amylase) and starch and/or starch hydrolyzates | | |
| Quercetin (flavonol; OH in 5, 7, 3' and 4') | α-glucosidase: pig liver, buckwheat seed, Mucor, *Penicillium*, *Saccharomyces* CGTase: *Bacillus*, *Klebsiella* α-amylase: *Aspergillus* | a-glucosyl quercetin (U.S. Pat. No. 5,565,435) (OH glucosylated not mentioned) |
| Enzymes and substrates: Glycosyltransferases able to transfer the glucose moiety of sucrose | | |
| Catechin (flavanol; OH in 3, 5, 7, 3' and 4') | *Streptococcus sobrinus* | 4'-O-α-D-glucopyranosyl-(+)-catechin (NAKAHARA et al. 1995) |
| Resveratrol (OH in 3, 5, 4') and pinosylvin (OH in 3, 5) | *Streptococcus mutans* | 3-O-α-D-glucopyranosyl-(E)-pinosylvin and 3-O-α-D-glucopyranosyl-(E)-resveratrol (SHIM et al. 2003) |
| Catechin (flavanol; OH in 3, 5, 7, 3' and 4') | *Streptococcus mutans* GS-5 (glucosyl-transferase D) | 4'-O-α-D-glucopyranosyl-(+)-catechin, 7-O-α-D-glucopyranosyl-(+)-catechin and 4',7-O-α-D-diglucopyranosyl-(+)-catechin (MEULENBELD et al. 1999) |
| Catechol (OH in 1 and 2), 3-methoxycatechol ($OCH_3$ in 3), 3-methylcatechol ($CH_3$ in 3), 4-methylcatechol ($CH_3$ in 4) | *Streptococcus mutans* GS-5 (glucosyl-transferase D) | Glucosides (MEULENBELD and HARTMANS, 2000) |
| Phenol, 3-hydroxyphenol, benzylalcohol, 2-hydroxybenzyl alcohol, 2-methoxybenzyl alcohol, 1-phenyl-1,2-ethanediol | *Streptococcus mutans* GS-5 (glucosyl-transferase D) | No glucoside (MEULENBELD and HARTMANS, 2000) |
| Quercetin (flavonol; OH in 3, 5, 7, 3' and 4'), luteolin (flavone; OH in 5, 7, 3' and 4'), myricetin (flavonol; OH in 3, 5, 7, 3', 4' and 5') | *L. mesenteroides* NRRL B-512F *L. mesenteroides* NRRL B-23192 | Glucosides (3' and 4' with luteolin and *L. mesenteroides* NRRL B-512F) (BERTRAND et al. 2006) |
| Diosmetin (flavone; OH in 5 and 3', $OCH_3$ in 4') | *L. mesenteroides* NRRL B-512F *L. mesenteroides* NRRL B-23192 | No glucoside (BERTRAND et al. 2006) |

Another key point to consider in the enzymatic synthesis of phenolic glycosides is the possibility to create phenolic derivatives that enable recovering of the initial phenolics by a hydrolysis reaction in smooth conditions.

Indeed, for a given polyphenol, the advantageous properties that are presently known correspond to a specific structure and it has thus to be demonstrated that the valuable derivative with increased water solubility and stability properties can be converted into the saccharide part on one hand and the aglycone part on the other hand. One example of decrease of antioxidant activity due to glycolation is given by MISHRA et al. (MISHRA B, PRIYADARSINI K I, KUMAR M S, UNNIKRISHNAN M K, MOHAN H (2003) Effect of O-glycosylation on the antioxidant activity and free radical reactions of a plant flavonoid, chrysoeriol. Bioorg Med Chem 11: 2677-85). Chrysoeriol and its glycoside (chrysoeriol-6-$O_G$-acetyl-4'-β-D-glucoside) are two flavonoids extracted from the tropical plant *Coronopus didy-*

*mus*; chrysoeriol shows a better protective effect than the glycoside when tested for their ability to inhibit lipid peroxidation induced by gamma-radiation, Fe (III) and Fe (II). To date, this reversibility is only known for the α-glucosyl quercetin obtained with starch-degrading enzymes in vitro (U.S. Pat. No. 5,565,435). So, if the functionalization of phenolics as glycoside derivatives is a way (i) to facilitate their formulation in cosmetic, pharmaceutical or any other man-made preparations due to a higher water solubility than that of the aglycone and (ii) to increase the stability of these phenolics in said formulas, both of them being universal properties of the glucosylated forms of polyphenols, these glycoside derivatives must be hydrolyzable in biological conditions.

There is therefore a need to create:
new derivatives of valuable phenolic compounds with increased water solubility (in the same physico-chemical conditions (pH, salinity, temperature, etc.)) and stability; and/or
new derivatives of valuable phenolic compounds that can be readily converted into their precursor, glucose and phenolic substance, in the place where they have to exert their biological activity and not during their storage in a commercial formula; and/or
new derivatives of valuable phenolic compounds that can be obtained through a process in which the synthesis and purification steps can be carried out in a reproducible manner and at any scale dependent on the market demand.

Owing to the fact that the pyrocatechol structure (presence of two vicinal hydroxyl groups) is recognized as particularly important for the scavenging activity of polyphenols, the phenolic compounds that seem particularly efficient are those containing a catechol structure; among the phenolic compounds that are of particular interest, there are the following compounds:
protocatechuic acid (3,4-dihydroxybenzoic acid, FIG. 2) and its ester derivatives; and/or
caffeic acid (3,4-dihydroxycinnamic acid, FIG. 3) and its ester derivatives, especially rosmarinic acid (3,4-dihydroxycinnamic acid (R)-1-carboxy-2-(3,4-dihydroxyphenyl) ethyl ester), chlorogenic acid (3-O-(3,4-dihydroxycinnamoyl)-D-quinic acid), chicoric acid, echinacoside, verbascoside and caffeic acid phenethyl ester, and its reduced form, hydrocaffeic acid, and its ester derivatives; and/or
special structures not closely related to protocatechuic acid or caffeic acid and containing the pyrocatechol ring: 3,4-dihydroxymandelic acid (FIG. 4) and its related substance 3,4-dihydroxyphenylacetic acid and 3,4-dihydroxyphenylglycol with a C2-C6 skeleton, and esculetin (6,7-dihydroxycoumarin, FIG. 5) with a C6-C3 skeleton; and/or
the flavanones taxifolin (3,5,7,3',4'-pentahydroxyflavanone, FIG. 6), fustin (3, 7,3',4'-tetrahydroxyflavanone), eriodictyol (5,7,3',4'-tetrahydroxyflavanone); and/or
the flavonols fisetine (3,7,3',4'-tetrahydroxyflavone) and rhamnetin (3,5,3',4'-tetrahydroxy-7-methoxyflavone); and/or
the flavones cirsiliol and 3',4',7-trihydroxyflavone and the isoflavone 3'-hydroxydaidzein.

More detailed information on these phenolics of interest is included below.

Protocatechuic acid (also named 3,4-dihydroxybenzoic acid) is found in many edible and medicinal plants, though most of the time at concentrations lower than derivatives of cinnamic acid. Though slightly less potent than caffeic acid, protocatechuic acid showed a time-dependent and dose-dependent inhibitory effect on T47D human breast cancer cell growth. It was also demonstrated that protocatechuic acid and caffeic acid interact directly with the aryl hydrocarbon receptor, inhibit nitric oxide synthase and have a pro-apoptotic effect (KAMPA M, ALEXAKI VI, NOTAS G, NIFLI A P, NISTIKAKI A, HATZOGLOU A, BAKOGEORGOU E, KOUIMTZOGLOU E, BLEKAS G, BOSKOU D, GRAVANIS A, CASTANAS E (2004) Antiproliferative and apoptotic effects of selective phenolic acids on T47D human breast cancer cells: potential mechanisms of action. Breast Cancer Res 6: R63-R74). LIU et al. (LIU K S, TSAO S M, YIN M C (2005) In vitro antibacterial activity of roselle calyx and protocatechuic acid. Phytother Res 19(11): 942-5) demonstrated in vitro an inhibitory effect of protocatechuic acid on the growth of methicillin-resistant *Staphylococcus aureus, Klebsiella pneumoniae, Pseudomonas aeruginosa* and *Acinetobacter baumannii*. The data from inhibition zone and minimum inhibitory concentration (MIC) values showed that protocatechuic acid effectively inhibited the growth of all tested bacterial pathogens. Recent studies indicate that protocatechuic acid could be used as a protective agent against cardiovascular diseases and neoplasms (SZUMILO J. (2005), Postepy Hig Med Dosw (Online) 59: 608-15). The mechanism of its action is mostly associated with antioxidant activity, including inhibition of generation as well as scavenging of free radicals and up-regulating enzymes which participate in their neutralization.

It was also demonstrated that protocatechuic acid is a possible chemopreventive agent for colon carcinogenesis through the suppression of manifestation of intermediate biomarkers induced by azoxymethane (AOM)-induced colon carcinogenesis in rats (TANAKA T, KOJIMA T, SUZUI M, MORI H. (1993) Chemoprevention of colon carcinogenesis by the natural product of a simple phenolic compound, protocatechuic acid: suppressing effects on tumor development and biomarker expression of colon tumorigenesis. Cancer Res. September 1; 53(17): 3908-13). Protocatechuic acid is therefore also a valuable active phenolic compound, but its bioavailability should be increased through functionalization to obtain more water-soluble derivatives.

Caffeic acid (also named 3,4-dihydroxycinnamic acid), a derivative of trans-cinnamic acid (trans-3-phenylacrylic acid), contains a —CH═CH—COOH group which ensures greater H-donating ability and subsequent radical stabilization than the carboxylate group in benzoic acids (RICE-EVANS C A, MILLER N J, PAGANDA G (1996) Structure—antioxidant activity relationships of flavonoids and phenolic acids. Free Radic Biol Med 20(7): 933-56). In addition to its possible beneficial effects on human health (caffeic and 3-methoxycaffeic or ferulic acids react with nitrite in vitro and inhibit nitrosamine formation in vivo; they also inhibit tyrosine nitration mediated by peroxynitrite), caffeic acid recently proved effective in protecting human skin from UVB-induced erythema (SVOBODOVA A, PSOTOVA J, WALTEROVA D (2003) Natural phenolics in the prevention of UV-induced skin damage. A review. Biomed Papers 147: 137-145). Caffeic acid is frequently encountered in the form of derivatives, with 1-carboxy-2-(3,4-dihydroxyphenyl)-ethanol to form rosmarinic acid, quinic acid to form chlorogenic acid and phenylethanol to form caffeic acid phenethyl ester.

Rosmarinic acid (also named 3-(3,4-dihydroxyphenyl)-2-[3-(3,4-dihydroxyphenyl)prop-2-enoyloxy]propanoic acid)

is found in the *Lamiaceae* genus of plants, which includes basil, sage, mint, rosemary and *perilla* leaf (AL SEREITI M R, ABU-KAMER K M, SEN P (1999) Pharmacology of rosemary and its therapeutic potentials. Indian J. Exp Biol 37(2): 124-30). Oral supplementation with *perilla* leaves or extracts of rosmarinic acid has been shown to suppress allergic reactions in mice and, more recently, in humans (MAKINO T, FURUTA A, FUJII H, NAKAGAWA T, WAKUSHIMA H, SAITO K, KANO Y (2001) Biol Pharm Bull 24(10): 1206-9—TAKAKANO H, OSAKABE N, SANBONGI C, YANAGASIWA R, INOUE K I, YASUDA A, NATSUME M, BABA S, ICHIISHI E I, YOSHIKAWA T (2004) Extract of *Perilla frutescens* enriched for rosmarinic acid inhibits seasonal allergic rhinoconjunctivitis in humans. Exp Biol Med 229(3): 247-54). Rosmarinic acid relieves allergy symptoms by preventing the activation of immune responder cells and by inducing apoptosis, or cellular suicide, in already activated immune responder cells (HUR Y G, YUN Y, WON J (2004) Rosmarinic acid induces p56lck-dependent apoptosis in jurkat and peripheral T cells via mitochondrial pathway independent from fas/fas ligand interaction. J Immunol 172(1): 79-87). Rosmarinic acid has also been shown to kill allergy-activated T cells and neutrophils during allergic reactions without affecting the T cells or neutrophils in their resting state (SANBONGI C, TAKANO H, OSAKABE N (2003) Rosmarinic acid inhibits lung injury induced by diesel exhaust particles. Free Radic Biol Med 34(8): 1060-9).

Rosmarinic acid was first shown to reduce allergic reactions in mice using the mouse ear passive cutaneous anaphylaxis reaction (MAKINO T, FURATA Y, WAKUSHIMA H, FUJII H, SAITO K, KANO Y (2003) Anti-allergic effect of *Perilla frutescens* and its active constituents. Phytother Res 17(3): 240-3). One study showed that rosmarinic acid inhibited IL-2 promoter activation of T cells in a large-scale screening of plant extracts (WON J, HUR Y G, HUR E M, PARK S H, KANG M A, CHOI Y, PARK C, LEE K H, YUN Y (2003), Rosmarinic acid inhibits TCR-induced T cell activation and proliferation in a Lck-dependent manner. Eur J Immunol 33(4): 870-9). Another study showed that rosmarinic acid, by inhibiting both the activation and proliferation of T cells, had potent immunosuppressive effects when combined with rapamycin, an anti-rejection drug (YUN S Y, HUR Y G, KANG M A, LEE J, AHN C, WON J (2003) Synergistic immunosuppressive effects of rosmarinic acid and rapamycin in vitro and in vivo. Transplantation 75(10): 1758-60).

Chlorogenic acid (also named 1,3,4,5-Tetrahydroxycyclohexanecarboxylic acid 3-(3,4-dihydroxycinnamate)) is the major soluble phenolic in solanaceous species such as potato, tomato and eggplant. It also accumulates to substantial levels in apples, pears, plums and coffee. SAWA et al. (SAWA T, NAKAO M, AKAIKE T, ONO K, MAEDA H (1999) Alkylperoxyl radical-scavenging activity of various flavonoids and other phenolic compounds: implications for the anti-tumor prompted effect of vegetables. J Agric Food Chem 47: 397-402) observed that it removes particularly toxic reactive species by scavenging alkylperoxyl radicals and may prevent carcinogenesis by reducing the DNA damage they cause.

Caffeic phenethyl ester (CAPE) is one of the major components of honeybee propolis, the resinous dark-colored material which is collected by honeybees from the buds of living plants mixed with beeswax and salivary secretions. CAPE is a potent and a specific inhibitor of activation of members of the transcription factor NF-κB family and this may provide the molecular basis for its multiple immunomodulatory and anti-inflammatory activities (NATARAJAN K, SINGH S, BURKE T R, GRUNBERGER D, AGGARWAL B B (1996) Caffeic acid phenethyl ester is a potent and specific inhibitor of activation of nuclear transcription factor NF-κB. Proc Natl Acad Sci USA 93: 9090-5). More recently, the role of CAPE as a potent antimetastatic agent which can markedly inhibit the metastatic and invasive capacity of malignant cells was evidenced (HWANG H J, PARK H J, CHUNG H J, MIN H Y, PARK E J, HONG J Y, LEE S K (2006) Inhibitory effects of caffeic acid phenethyl ester on cancer cell metastasis mediated by the down-regulation of matrix metalloproteinase expression in human HT1080 fibrosarcoma cells. J Nutri Biochem 17: 356-62).

Esculetin (or aesculetin, also named 6,7-dihydroxycoumarin), a member of the family of the C6-C3 phenolics, has a coumarin structure derived from trans-cinnamic acid via ortho-hydroxylation (for memory, caffeic acid is 3,4-dihydroxycinnamic acid), trans-cis isomerisation of the side chain double bond and lactonisation. Whereas the trans form is stable and cannot cyclize, the cis form is very unstable and cyclization is thus favored. Glucose is a good leaving group which assists in the cis-trans transformation. A specific enzyme found in *Melilotus alba* (*Leguminosae*) specifically hydrolyses the cis-glucoside glucosidase). Some of its properties are the inhibition of Ras-mediated cell proliferation and attenuation of vascular restenosis following angioplasty in rats (PAN S L, HUANG Y W, GUH J H, CHANG Y L, PENG C Y, TENG C M (2003) Esculetin inhibits Ras-mediated cell proliferation and attenuates vascular restenosis following angioplasty in rats. Biochem Pharmacol 65: 1897-1905) and the inhibition of mushroom tyrosinase (MASAMOTO Y, ANDO H, MURATA Y, SHOMOISHI Y, TADA M, TAKAHATA K (2003) Mushroom tyrosinase inhibitory activity of esculetin isolated from seeds of *Euphorbia lathyris* L. Biosci Biotechnol Biochem 67(3): 631-4). It has to be mentioned that esculetin is frequently encountered as a glucoside, esculin (esculetin-6-β-D-glucopyranoside), with a β-glucosidic linkage at position 6. The members of the C6-C2 phenolics are basically found in the catecholamine metabolism and 3,4-dihydrophenyl related substances could have interesting properties (EISENHOFER G, KOPIN I J, GOLDSTEIN D S (2004) Catecholamine metabolism: a contemporary view with implications for physiology and medicine. Parmacol Rev 56(3): 331-49).

Taxifolin (or dihydroquercetin, or 3,5,7,3',4'-pentahydroxyflavanone, or (2R,3S)-2-(3,4-dihydroxyphenyl)-3,5,7-trihydroxy-chroman-4-one) occurs in various barks (*Larix sibirica* Lebed, *Pinus pinaster* ssp. *atlantica*) and in *Silybum marinum* seeds (used for the preparation of the silymarin complex and containing silymarin flavonolignans which are biogenetically formed by oxidative addition of coniferyl alcohol to taxifolin. It has a chiral bond between cycle B and the two other cycles. Relating to the PP-vitamin group, it possesses a wide spectrum of biological activities (MIDDLETON E, KANDASWAMI C, THEOHARIDES T C (2000) The effects of plant flavonoids on mammalian cells: implications for inflammation, heart disease and cancer. Pharmacol Rev 52(4): 673-752). It shows capillary-protecting, anti-inflammatory and gastro-protective action, decreases spasms of sleek muscles of the intestine, increases function of the liver and possesses antiradiation protective activity. Taxifolin has also been shown to have potential applications in reducing skin inflammation (BITO T, ROY S, SEN CK, SHIRAKAWA T, GOTOH A, UEDA M, ICHIHASHI M, PACKER L (2002) Flavonoids differentially regulate IFN-gamma-induced ICAM-1 expression in human keratinocytes: molecular mechanisms of action. FEBS Lett. 520(1-3): 145-52). However, Taxifolin is poorly soluble in aqueous solution (around 1 g/l), which prevents its usage for some cosmetic and therapeutic applications.

Glycosylation being recognized to render polyphenols, in vegetal cells as well as in vitro, more water-soluble and less reactive toward free radicals, if glucosides of these phenolics of particular interest exist, then they might represent polyphenol derivatives with increased water solubility and stability, and thus with increased added value.

It would also be useful to obtain derivatives from these phenolics which can be converted during their final usage in the metabolizable initial phenolic structure. This objective can be achieved by means of the present invention.

SUMMARY OF THE INVENTION

The present invention concerns a method for producing a phenolic compound O-α-glucoside comprising incubating sucrose and a glucansucrase from *Leuconostoc* species, preferably from *Leuconostoc mesenteroides* NRRL B-512F, preferably in buffered water at a pH convenient for the enzymatic activity (well-known by a skilled man) or in buffered water at a pH convenient for the enzymatic activity-cosolvent mixture, with a phenolic compound having the following formula:

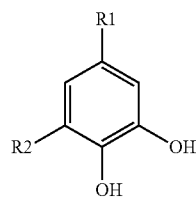
(I)

wherein
R2 is H or OH; and
R1 is selected from the group consisting of

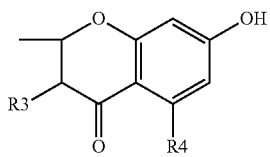

wherein R3 and R4, independently, are H or OH, with the proviso that at least one among R3 and R4 represents OH; and

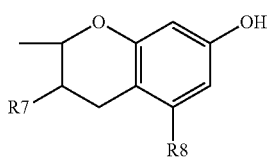

wherein R7 is selected from the group consisting of H, —OH or —OCOR and R8 is H or OH, with the proviso that at least one among R7 and R8 represents OH;

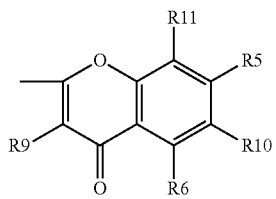

wherein R5 is OH or $OCH_3$, R6 is H or OH, R9 is H or OH, R10 is H, $OCH_3$ or $C_6H_{11}O_5$, and R11 is H, OH or $C_6H_{11}O_5$, with the proviso that R10 and R11 cannot be both H when R5 and R6 are both OH and that when R10 is $C_6H_{11}O_5$, then R11 is H;

—$(CH_2)_n$—COOR or —$(CH_2)_n$—CONHR, with n being an integer from 0 to 2;

—(CR12=CH)—COOR or —(CR12=CH)—CONHR, R12 being H or a $C_1$-$C_6$ linear, branched or cyclic alkyl or alkenyl, preferably methyl, ethyl, propyl, cyclohexyl or phenyl, more preferably methyl or phenyl;

—$(CH_2)_n$—OR or —$(CH_2)_n$—NHR with n being an integer from 0 to 2;

—$(CH_2)_n$—COR or —(CH═CH)$_n$—COR with n being an integer from 0 to 2;

H;

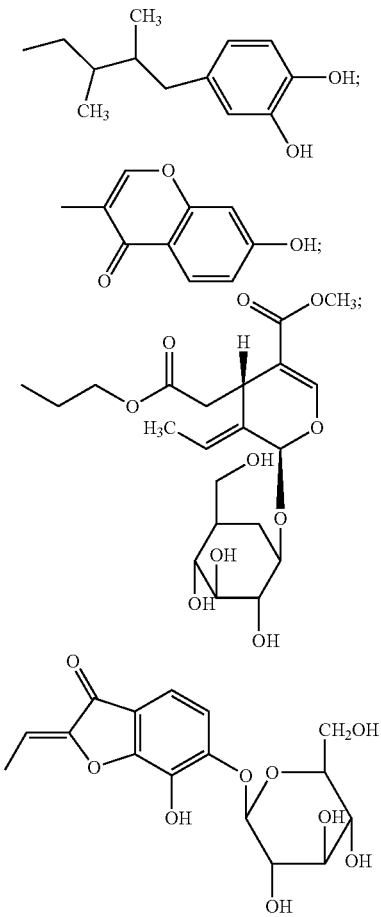

and
a $C_1$-$C_{10}$ hydrocarbon group which forms with the represented ring of formula (I) a fused ring (bi or tricyclic)

together with the ortho carbon of R1, said ring being optionally interrupted by at least one heteroatom;

wherein R is H or a linear, branched or cyclic, aromatic or not, saturated or unsaturated, $C_1$-$C_{10}$ hydrocarbon group, optionally interrupted by at least one heteroatom, wherein said hydrocarbon group comprises an alkyl, an alkenyl or an alkynyl, preferably an alkyl or an alkenyl, which can be substituted by one or several substituents selected from the group consisting of an ($C_5$-$C_9$)aryl, an ($C_4$-$C_9$)heterocycle, an ($C_1$-$C_3$)alkoxy, an ($C_2$-$C_3$)acyl, an ($C_1$-$C_3$)alcohol, a carboxylic group (—COOH), an ($C_2$-$C_3$)ester, an ($C_1$-$C_3$) amine, an amino group (—NH$_2$), an amide (—CONH$_2$), an ($C_1$-$C_3$)imine, a nitrile, a hydroxyl (—OH), an aldehyde group (—CHO), a halogen, a ($C_1$-$C_3$)halogenoalkyl, a thiol (—SH), a ($C_1$-$C_3$)thioalkyl, a ($C_1$-$C_3$)sulfone, a ($C_1$-$C_3$) sulfoxide and a combination thereof.

Preferably, the buffered water at a pH convenient for the enzymatic activity used either without a cosolvent or in a mixture with a cosolvent consists of sodium or potassium acetate buffer at a concentration ranging from 20 to 500 mM in water but any other buffering substance without any negative effect on the enzymatic activity can be used. Preferably, the buffered water at a pH convenient for the enzymatic activity-cosolvent mixture consists of a mixture of water, preferably buffered water as previously described, and dimethyl sulfoxide (DMSO) with a ratio of less than 35% of DMSO (volume/volume), preferably between 15-25%, more preferably about 15%.

In a first embodiment, R1 of the phenolic compound is

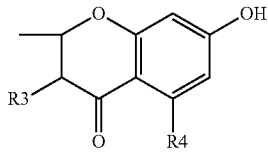

wherein R3 and R4, independently, are H or OH, with the proviso that at least one among R3 and R4 represents OH. In particular, the phenolic compound can be selected from the group consisting of the taxifolin, the eriodictyol, the dihydrorobinetin and the fustin.

In a second embodiment, R1 of the phenolic compound is

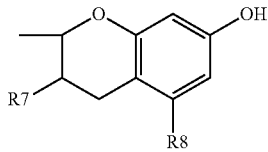

wherein R7 is selected from the group consisting of H, —OH or —OCOR and R8 is H or OH, with the proviso that at least one among R7 and R8 represents OH. In particular, the phenolic compound can be selected from the group consisting of the catechin, the epicatechin, the catechin gallate, the epicatechin gallate, the gallocatechin, the epigallocatechin, the gallocatechin gallate and the epigallocatechin gallate.

In a third embodiment, R1 of the phenolic compound is

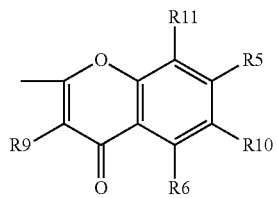

wherein R5 is OH or OCH$_3$, R6 is H or OH, R9 is H or OH, R10 is H, OCH$_3$ or $C_6H_{11}O_5$, and R11 is H, OH or $C_6H_{11}O_5$, with the proviso that R10 and R11 cannot be both H when R5 and R6 are both OH and that when R10 is $C_6H_{11}O_5C_6H_{11}O_5$, then R11 is H. In particular, the phenolic compound can be selected from the group consisting of the rhamnetin, the fisetin, the robinetin, the gossypetin, the orientin, the homoorientin and the cirsiliol.

In a fourth embodiment, R1 of the phenolic compound is —(CH$_2$)$_n$—COOR or —(CH$_2$)$_n$—CONHR with n being an integer from 0 to 2. In particular, the phenolic compound can be selected from the group consisting of the homoprotocatechuic acid, the dihydrocaffeic acid, the protocatechuic acid ethyl ester, the propyl gallate, the gallic acid, the hamamelitannin (2',5-di-O-galloyl-hamamelose) and the protocatechuic acid.

In a fifth embodiment, R1 of the phenolic compound is —(CR12=CH)—COOR or —(CR12=CH)—CONHR, R12 being H or a $C_1$-$C_6$ linear or cyclic alkyl or alkenyl, preferably methyl, ethyl, propyl, cyclohexyl or phenyl. In particular, the phenolic compound can be selected from the group consisting of the caffeic acid, the rosmarinic acid, the esculetin, the 4-methylesculetin, the nordalbergin (6,7-dihydroxyphenylcoumarin), the chlorogenic acid, the caffeic acid phenethyl ester, the chicoric acid (dicaffeoyl tartaric acid), the echinacoside (2-(3,4-dihydroxyphenyl)ethyl O-6-deoxy-alpha-L-mannopyranosyl-(1→3)-O-(beta-D-glucopyranosyl-(1→6))-, 4-(3-(3,4-dihydroxyphenyl)-2-propenoate), beta-D-glucopyranoside) and the verbascoside.

In a sixth embodiment, R1 of the phenolic compound is —(CH$_2$)$_n$—OR or —(CH$_2$)$_n$—NHR with n being an integer from 0 to 2; for instance, the phenolic compound is the hydroxytyrosol.

In a seventh embodiment, R1 of the phenolic compound is —(CH$_2$)$_n$—COR or —(CH=CH)$_n$—COR with n being an integer from 0 to 2. In particular, the phenolic compound can be selected from the group consisting of the maclurine, the 3,4-dihydroxybenzaldehyde, the 3,4-dihydroxybenzophenone, the butein (2',3,4,4'-tetrahydroxychalcone), the 3,4-dihydroxyacetophenone, the marein (2',3,3',4,4'-pentahydroxy-4'-glucosylchalcone), and the eriodictyolchalcone (2',4',6',3,4-pentahydroxychalcone).

In an eighth embodiment, R1 of the phenolic compound is selected from the group consisting of

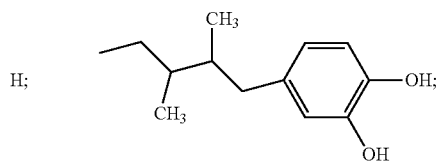

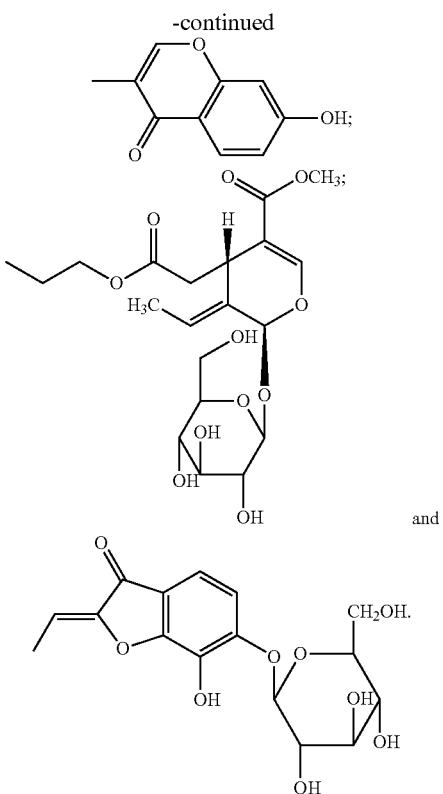

In particular, the phenolic compound can be selected from the group consisting of the pyrocatechol, the nordihydroguaiaretic acid, the 3-hydroxydaidzein, the oleuropein and the maritimein (3',4',6,7-tetrahydroxy-6-O-glucosylaurone), respectively.

In a ninth embodiment, R1 of the phenolic compound is a $C_1$-$C_{10}$ hydrocarbon group which forms with the represented ring of formula (I) a fused ring (bi or tricyclic) together with the ortho carbon of R1, said ring being optionally interrupted by at least one heteroatom.

In particular, the phenolic compound can be selected from the group consisting of

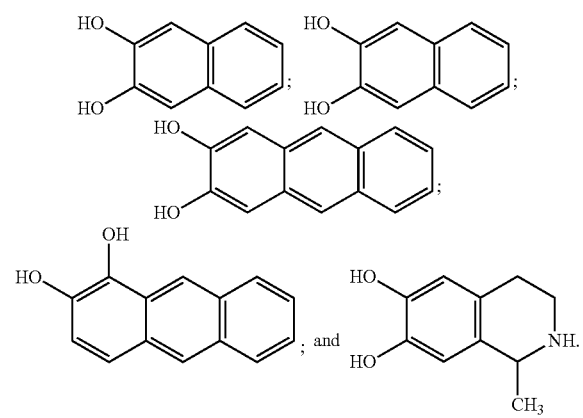

Preferably, the phenolic compound can be selected from the group consisting of the anthrarobin and the salsolinol (1-methyl-6,7-dihydroxy-1,2,3,4-tetrahydroisoquinoline).

The present invention also concerns the phenolic compounds O-α-glucosides obtainable by the method of the invention. Consequently, the present invention concerns a phenolic compound O-α-glucoside having the following formula:

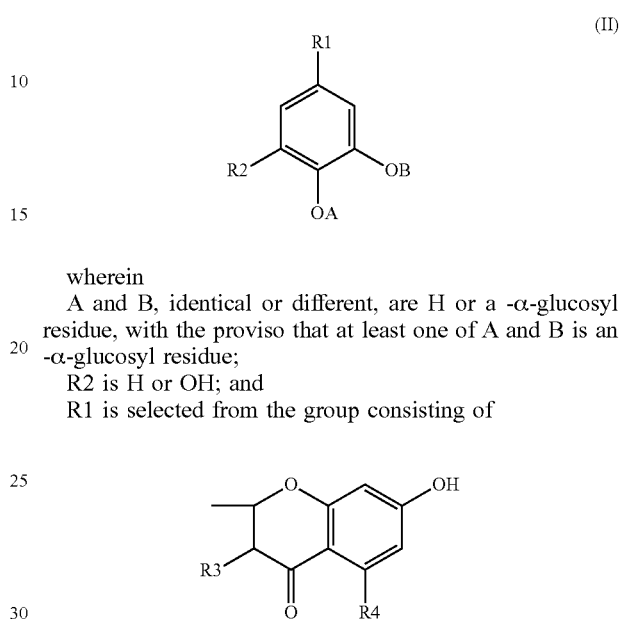

wherein
A and B, identical or different, are H or a -α-glucosyl residue, with the proviso that at least one of A and B is an -α-glucosyl residue;
R2 is H or OH; and
R1 is selected from the group consisting of

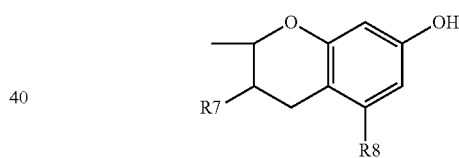

wherein R3 and R4, independently, are H or OH, with the proviso that at least one among R3 and R4 represents OH; and

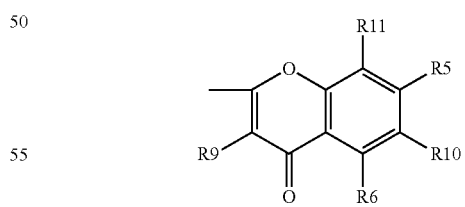

wherein R7 is selected from the group consisting of H, —OH or —OCOR and R8 is H or OH, with the proviso that, when R2 is H, R7 and R8 are not both OH, and at least one among R7 and R8 is OH;

wherein R5 is OH or $OCH_3$, R6 is H or OH, R9 is H or OH, R10 is H, $OCH_3$ or $C_6H_{11}O_5$, and R11 is H, OH or $C_6H_{11}O_5$, with the proviso that R10 and R11 cannot be both H when R5 and R6 are both OH and that when R10 is $C_6H_{11}O_5$, then R11 is H;
—$(CH_2)_n$—COOR or —$(CH_2)_n$—CONHR, with n being an integer from 0 to 2;
—(CR12=CH)—COOR or —(CR12=CH)—CONHR, R12 being H or a $C_1$-$C_6$ linear, branched or cyclic alkyl or alkenyl, preferably methyl, ethyl, propyl, cyclohexyl or phenyl, more preferably methyl or phenyl;

—$(CH_2)_n$—OR or —$(CH_2)_n$—NHR with n being an integer from 0 to 2;

—$(CH_2)_n$—COR or —$(CH=CH)_n$—COR with n being an integer from 0 to 2;

H;

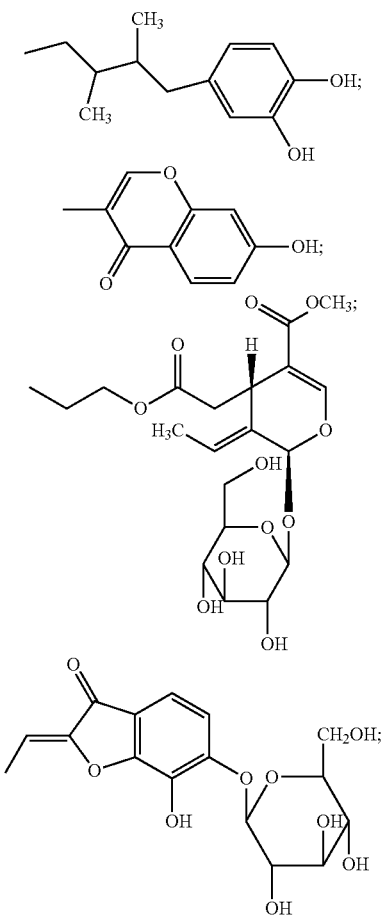

and a $C_1$-$C_{10}$ hydrocarbon group which forms with the represented ring of formula (I) a fused ring (bi or tricyclic) together with the ortho carbon of R1, said ring being optionally interrupted by at least one heteroatom;

wherein R is H or a linear, branched or cyclic, aromatic or not, saturated or unsaturated, $C_1$-$C_{10}$ hydrocarbon group, optionally interrupted by at least one heteroatom, wherein said hydrocarbon group comprises an alkyl, an alkenyl, or an alkynyl, preferably an alkyl or an alkenyl, which can be substituted by one or several substituents selected from the group consisting of an ($C_5$-$C_9$)aryl, an ($C_3$-$C_9$)heterocycle, an ($C_1$-$C_3$)alkoxy, an ($C_2$-$C_3$)acyl, an ($C_1$-$C_3$)alcohol, a carboxylic group (—COOH), an ($C_2$-$C_3$)ester, an ($C_1$-$C_3$) amine, an amino group (—$NH_2$), an amide (—$CONH_2$), an ($C_1$-$C_3$)imine, a nitrile, an hydroxyl (—OH), an aldehyde group (—CHO), a halogen, a ($C_1$-$C_3$)halogenoalkyl, a thiol (—SH), a ($C_1$-$C_3$)thioalkyl, a ($C_1$-$C_3$)sulfone, a ($C_1$-$C_3$) sulfoxide and a combination thereof.

A first preferred phenolic compound O-α-glucoside of formula (II) has R1 which is

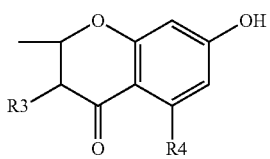

and preferably the phenolic compound O-α-glucoside is selected from the group consisting of the taxifolin O-α-glucoside, the eriodictyol O-α-glucoside, the dihydrorobinetin O-α-glucoside and the fustin O-α-glucoside.

A second preferred phenolic compound O-α-glucoside of formula (II) has R1 which is

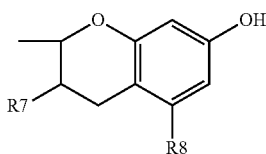

and preferably the phenolic compound O-α-glucoside is selected from the group consisting of the catechin gallate O-α-glucoside, the epicatechin gallate O-α-glucoside, the gallocatechin O-α-glucoside, the epigallocatechin O-α-glucoside, the gallocatechin gallate O-α-glucoside and the epigallocatechin gallate O-α-glucoside.

A third preferred phenolic compound O-α-glucoside of formula (II) has R1 which is

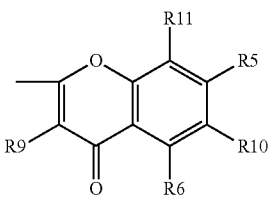

and preferably the phenolic compound O-α-glucoside is selected from the group consisting of the rhamnetin O-α-glucoside, the fisetin O-α-glucoside, the robinetin O-α-glucoside, the gossypetin O-α-glucoside, the orientin O-α-glucoside, the homoorientin O-α-glucoside and the cirsiliol O-α-glucoside.

A fourth preferred phenolic compound O-α-glucoside of formula (II) has R1 which is —$(CH_2)_n$—COOR or —$(CH_2)_n$—CONHR with n being an integer from 0 to 2, and preferably the phenolic compound O-α-glucoside is selected from the group consisting of the homoprotocatechuic acid O-α-glucoside, the dihydrocaffeic acid O-α-glucoside, the protocatechuic acid ethyl ester O-α-glucoside, the propyl gallate O-α-glucoside, the gallic acid O-α-glucoside, the hamamelitannin O-α-glucoside and the protocatechuic acid O-α-glucoside.

In a fifth preferred phenolic compound O-α-glucoside of formula (II) has R1 which is —(CR12=CH)—COOR or —(CR12=CH)—CONHR, R12 being H or a $C_1$-$C_6$ linear or cyclic alkyl or alkenyl, preferably methyl, ethyl, propyl, cyclohexyl or phenyl and preferably the phenolic compound O-α-glucoside is selected from the group consisting of the caffeic acid O-α-glucoside, the rosmarinic acid O-α-glucoside, the esculetin O-α-glucoside, the 4-methylesculetin O-α-glucoside, the nordalbergin (6,7-dihydroxyphenylcoumarin) O-α-glucoside, the chlorogenic acid O-α-glucoside, the caffeic acid phenethyl ester O-α-glucoside, the chicoric acid (dicaffeoyl tartaric acid) O-α-glucoside, the echinacoside (2-(3,4-dihydroxyphenyl)ethyl O-6-deoxy-alpha-L-mannopyranosyl-(1→3)-O-(beta-D-glucopyranosyl-(1→6))-, 4-(3-(3,4-dihydroxyphenyl)-2-propenoate) O-α-glucoside, beta-D-glucopyranoside O-α-glucoside and the verbascoside O-α-glucoside.

A sixth preferred phenolic compound O-α-glucoside of formula (II) has R1 which is —(CH$_2$)$_n$—OR or —(CH$_2$)$_n$—NHR with n being an integer from 0 to 2, and preferably the phenolic compound O-α-glucoside is the hydroxytyrosol O-α-glucoside.

A seventh preferred phenolic compound O-α-glucoside of formula (II) has R1 which is —(CH$_2$)$_n$—COR or —(CH=CH)$_n$—COR with n being an integer from 0 to 2, and preferably the phenolic compound O-α-glucoside is selected from the group consisting of the maclurine O-α-glucoside, the 3,4-dihydroxybenzaldehyde O-α-glucoside, the 3,4-dihydroxybenzophenone O-α-glucoside, the butein (2',3,4,4'-tetrahydroxychalcone) O-α-glucoside, the 3,4-dihydroxyacetophenone O-α-glucoside, the marein (2',3,3',4,4'-pentahydroxy-4'-glucosylchalcone) O-α-glucoside and the eriodictyolchalcone (2',4',6',3,4-pentahydroxychalcone) O-α-glucoside.

An eighth preferred phenolic compound O-α-glucoside of formula (II) has R1 which is selected from the group consisting of

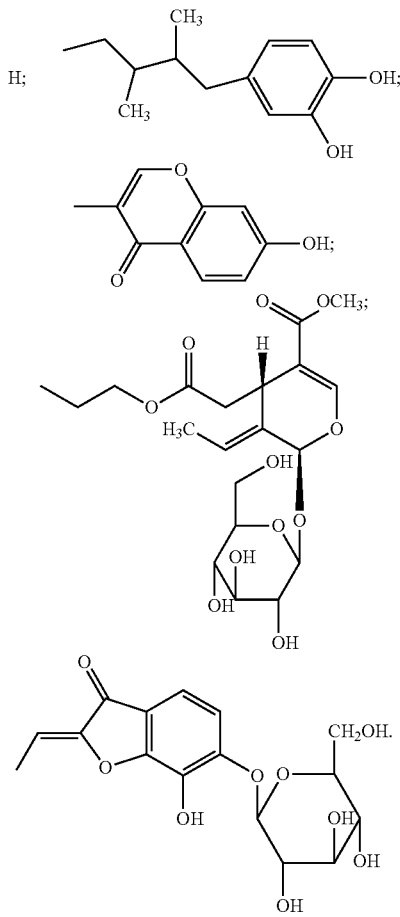

The phenolic compound O-α-glucoside is preferably selected from the group consisting of the pyrocatechol O-α-glucoside, the nordihydroguaiaretic acid O-α-glucoside, the 3-hydroxydaidzein O-α-glucoside, the oleuropein O-α-glucoside and maritimein (3',4',6,7-tetrahydroxy-6-O-glucosylaurone) O-α-glucoside.

In a ninth preferred phenolic compound O-α-glucoside of formula (II) has R1 which is a C$_1$-C$_{10}$ hydrocarbon group which forms with the represented ring of formula (I) a fused ring (bi or tricyclic) together with the ortho carbon of R1, said ring being optionally interrupted by at least one heteroatom. Preferably the phenolic compound O-α-glucoside is selected from the group consisting of the anthrarobin O-α-glucoside and the salsolinol (1-methyl-6,7-dihydroxy-1,2,3,4-tetrahydroisoquinoline) O-α-glucoside.

In a preferred embodiment, the phenolic compound O-α-glucoside of the present invention has an -α-glucosyl residue which is a glucose monomer, dimer, trimer or tetramer, preferably a monoglucoside.

Preferably, the phenolic compound O-α-glucosides of the present invention have a 20-fold higher solubility than the corresponding aglycone in the same physiological conditions.

The phenolic compound O-α-glucosides of the present invention can be cleaved by an enzyme to release the corresponding aglycones. Said enzyme is an O-α-glucosidase. Preferably, said enzyme is issued from human-associated microorganisms, in particular human microorganisms associated with the skin, mouth, intestinal tract, upper respiratory system or female genital tract, even more preferably skin-associated microorganisms.

The present invention further concerns phenolic compound O-α-glucosides of the present invention as medicaments.

The present invention also concerns a pharmaceutical or cosmetic composition comprising a phenolic compound O-α-glucoside of the present invention.

The present invention also concerns the use of a phenolic compound O-α-glucoside of the present invention for preparing a pharmaceutical or cosmetic composition to be administered topically, orally, rectally, nasally or vaginally, wherein enzymes issued from microorganisms associated with the skin, mouth, intestinal tract, upper respiratory system or female genital tract release the corresponding aglycone.

The present invention also concerns the use of a phenolic compound O-α-glucoside of the present invention for preparing a pharmaceutical or cosmetic composition for treating or preventing a cancer, a cardiovascular disease, a bacterial infection, a UVB-induced erythema, an allergy, or an inflammatory or immune disorder.

BRIEF DESCRIPTION OF THE DRAWINGS

FIGS. 4—3,4-dihydroxymandelic acid.

DETAILED DESCRIPTION OF THE INVENTION

Definitions

Figure 1:
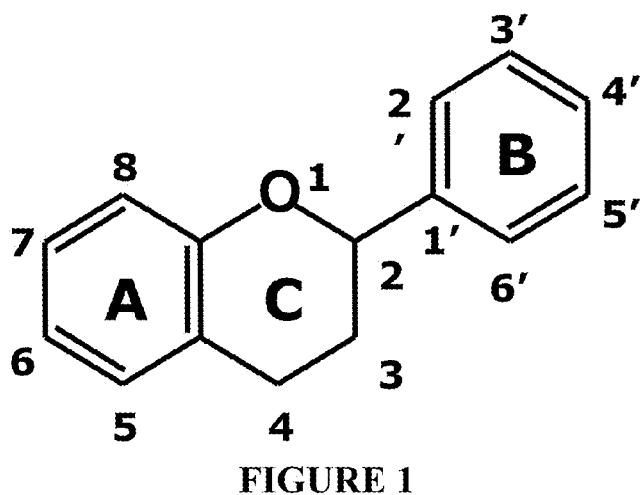
FIG. 1—Flavonoids: basic structure and numbering of carbon atoms.
Figure 2:
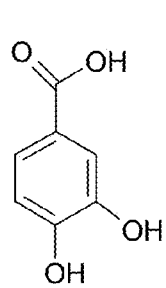
FIG. 2—Protocatechuic acid.
Figure 3:
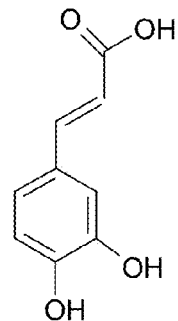
FIG. 3—Caffeic acid (3,4-dihydroxycinnamic acid).
Figure 4:
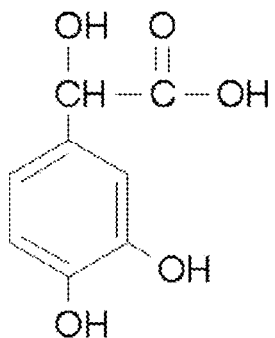
Figure 5:
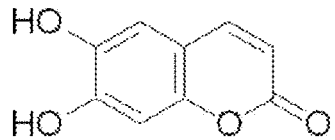
FIG. 5—Esculetin (6,7-dihydroxycoumarin).
Figure 6:
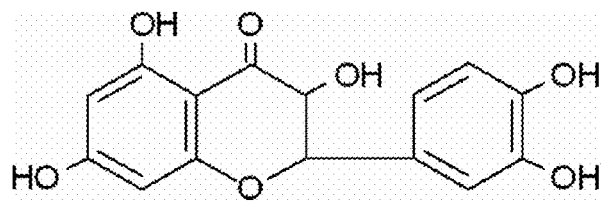
FIG. 6—Taxifolin.

Phenolic compounds or Phenolics: compounds that possess an aromatic ring bearing one or more hydroxyl substituents.

Flavonoids: polyphenolic compounds possessing 15 carbon atoms, two benzene rings joined by a linear three-carbon chain giving a system C6-C3-C6. The first benzene ring (ring A) forms with an oxygen atom and the three carbon atoms joining the two benzene rings a chromane skeleton (rings A and C). The chromane skeleton bears the second aromatic ring B in position 2, 3 or 4. In a few cases, the six-membered heterocyclic ring C occurs in an isomeric open form or is replaced by a five-membered ring. Both the oxidation state of the heterocyclic ring C and the position of ring B are important in the classification of flavonoids:

anthocyanins: ring C is a pyran which participates in a 3-hydroxychromane skeleton substituted in 2, catechic substances (flavanols): ring C is a hydrogenated tetrahydropyran which participates in a 3-hydroxy or a 3,4-dihydroxychromane skeleton substituted in 2 (catechin, epicatechin, gallocatechin and epigallocatechin forming the condensable tannins), flavones: ring C is a pyrone substituted in 2, flavonols: ring C is a pyrone hydroxylated in 3 and substituted in 2, flavanones: ring C is a dihydropyrone substituted in 2, dihydroflavonols: ring C is a dihydropyrone hydroxylated in 3 and substituted in 2, isoflavones: flavones with the substitution in 3 instead of 2, chalcones and dihydrochalcones: ring C is open and with a C2-C3 double bond (chalcones) or not (dihydrochalcones), and aurones: ring C is a five-membered ring.

Enzyme: protein molecule that catalyses chemical reactions on molecules (named substrates) to obtain other molecules (named products). A recommended name, a systematic name which stresses the type of reaction and an Enzyme Commission (EC) code number are assigned to each enzyme. These code numbers, prefixed by EC, contain four elements separated by points. The first number shows to which of the six main divisions (classes) the enzyme belongs: oxidoreductases (EC 1), transferases (EC 2), hydrolases (EC3), lyases (EC4), isomerases (EC5) and ligases (EC6). The second number indicates the subclass, the third the sub-subclass and the fourth is the serial number of the enzyme in its sub-subclass.

Bioavailability: the degree to which or rate at which a molecule or other substance is absorbed or becomes available at the site of physiological activity after administration or application.

Glucansucrases: common name of glucosyltransferases with the EC number 2.4.1.5 (see KRALJ S, VAN GEELSCHUTTEN G H, DONDORFF MMG, KIRSANOVS S, VAN DER MAAREL MJEC, DIJKHUIZEN L (2004) Glucan synthesis in the genus *Lactobacillus*: isolation and characterization of glucansucrase genes, enzymes and glucan products from six different strains. Microbiology 150: 3681-90).

Glycosyltransferase: enzyme that catalyzes the transfer of glycosyl group(s) from one compound (donor) to another (acceptor). Glycosyltransferases are classified as transferases, with the EC number EC 2.4. Transferases that transfer hexoses (carbohydrate molecules that have six carbon atoms per molecule) are included in the sub-subclass EC 2.4.1. Transferases that transfer the glucose moiety of sucrose to an acceptor are EC 2.4.1.4 (sucrose: 1,4-α-D-glucan 4-α-D-glucosyltransferase; recommended name: amylosucrase), EC 2.4.1.5 (sucrose: 1,6-α-D-glucan 6-α-D-glucosyltransferase; recommended name: dextransucrase) and EC 2.4.1.7 (sucrose: orthophosphate α-D-glucosyltransferase; recommended name: sucrose phosphorylase).

Glycone: chemical part of a glycosidic derivative which belongs to the carbohydrate family. If the glycone group is glucose, then the molecule is a glucoside; if it is fructose, then the molecule is a fructoside; if it is glucuronic acid, then the molecule is a glucuronide.

Glycosidic bond: chemical linkage between a glycone and another glycone or an aglycone. Depending on whether the glycosidic bond lies "below" or "above" the plane of the cyclic carbohydrate molecule when considering the HAWORTH projection, glycosides are classified as α-glycosides or β-glycosides.

Aglycone: Chemical part of a glycosidic derivative which is not the glycone one.

Where "comprising" is used, this can preferably be replaced by "consisting essentially of", more preferably by "consisting of".

In the context of the present invention, the term "alkyl" more specifically means a group such as methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl and the other isomeric forms thereof. $(C_1-C_6)$alkyl more specifically means methyl, ethyl, propyl, isopropyl, butyl, isobutyl, tert-butyl, pentyl, hexyl and the other isomeric forms thereof. $(C_1-C_3)$alkyl more specifically means methyl, ethyl, propyl or isopropyl.

The term "alkenyl" refers to an alkyl group defined hereinabove having at least one unsaturated ethylene bond and the term "alkynyl" refers to an alkyl group defined hereinabove having at least one unsaturated acetylene bond. $(C_2-C_3)$alkenyl includes an ethenyl and a propenyl (1-propenyl or 2-propenyl).

The "aryl" groups are mono-, bi- or tri-cyclic aromatic hydrocarbons having from 5 to 9 carbon atoms. Examples include a phenyl.

"Heterocycle" groups are groups containing 1 to 3 rings comprising one or more heteroatoms, preferably 1 to 5 endocyclic heteroatoms. They may be mono-, bi- or tri-cyclic. They may be aromatic or not. Examples of aromatic heterocycles include pyridine, pyridazine, pyrimidine, pyrazine, furan, thiophene, pyrrole, oxazole, thiazole, isothiazole, imidazole, pyrazole, oxadiazole, triazole, thiadiazole and triazine groups. Examples of bicycles include quinoline, isoquinoline and quinazoline groups (for two 6-membered rings) and indole, benzimidazole, benzoxazole, benzothiazole and indazole (for a 6-membered ring and a 5-membered ring). Nonaromatic heterocycles comprise piperazine, piperidine, etc.

($C_1$-$C_3$)alkoxy includes methoxy, ethoxy, propyloxy, and isopropyloxy.

($C_2$-$C_3$)acyl includes acetyl, propylacyl and isopropylacyl.

($C_1$-$C_3$)alcohol includes methanol, ethanol, propanol and isopropanol.

($C_2$-$C_3$)ester includes methylester and ethylester.

($C_1$-$C_3$)amine includes methylamine, ethylamine and propylamine.

($C_1$-$C_3$)imine includes methylimine, ethylimine and propylimine.

The halogen can be Cl, Br, I or F.

($C_1$-$C_3$)halogenoalkyl includes halogenomethyl, halogenoethyl and halogenopropyl.

($C_1$-$C_3$)thioalkyl includes thiomethyl, thioethyl and thiopropyl.

($C_1$-$C_3$)sulfone includes methylsulfone, ethylsulfone and propylsulfone.

($C_1$-$C_3$)sulfoxide includes methylsulfoxide, ethylsulfoxide, propylsulfoxide and isopropylsulfoxide.

"Heteroatom" denotes N, S or O.

This invention also relates to a process for preparing O-α-glucosides of phenolic compounds containing a catechol structure and, for instance, selected from protocatechuic acid and its ester derivatives, caffeic acid and its esters derivatives, especially rosmarinic acid, chlorogenic acid and caffeic acid phenethyl ester and hydrocaffeic acid or 3,4-dihydroxyhydrocinnamic acid, 3,4-dihydroxyphenylglycol, esculetin, taxifolin, fustin, eriodictyol, fisetin and rhamnetin. In particular, the phenolic compounds containing a catechol structure can be selected from the group consisting of the epicatechin gallate, the eriodictyol, the esculetin, the epicatechin, the fisetin, the fustin, the homoprotocatechuic acid, the protocatechuic acid, the protocatechuic acid ethyl ester, the hydroxytyrosol, the maclurine, the nordihydroguaiaretic acid, the oleuropein, the pyrocatechol, the rhamnetin, the rosmarinic acid, the taxifolin, the 3-hydroxydaidzein, the 3,4-dihydroxybenzophenone, the caffeic acid, the dihydrocaffeic acid, the caffeic acid phenethyl ester, the catechin, the cirsiliol, the chlorogenic acid, the gossypetin, the orientin, the homoorientin, the 3,4-dihydroxybenzaldehyde, the butein, the 3,4-dihydroxyacetophenone, the marein, the maritimein, the eriodictyolchalcone, the 4-methylesculetin, the nordalbergin, the salsolinol, the chicoric acid, the echinacoside, the verbascoside, the anthrarobin, the epigallocatechin, the dihydrorobinetin, the gallocatechin, the gallic acid, the propyl gallate, the epigallocatechin gallate, the hamamelitannin and the robinetin. The process for preparing O-α-glucosides of phenolic compounds containing a catechol structure can also be performed with cirsiliol, 3',4',7-trihydroxyflavone and 3'-hydroxydaidzein (flavones and isoflavone).

For this purpose, an enzymatic reaction is achieved using sucrose, an abundant and rather cheap substance used in the food and feed fields. This reaction consists of the transfer of the glucose part of sucrose on a hydroxyl group of the catechol ring by a glycosyltransferase (EC 2.4.1) or, once a first glucosyl residue has been attached to a hydroxyl group of the catechol ring, the transfer of the glucose part of sucrose to a hydroxyl group of the fixed glucose; the position of this hydroxyl group depends on the enzyme specificity. As each phenolic compound cited above bears two hydroxyl groups on said ring, two derivatives can be obtained by this enzymatic reaction. When a population of glycoside derivatives results from the synthesis reaction ("population" means the compounds for which the catechol ring has one of its hydroxyl group substituted or both of its hydroxyl group substituted by one glucosyl residue or an oligosaccharide), the entire population is said to be the product and corresponds to the invention.

The present invention concerns a method for producing a phenolic compound O-α-glucoside comprising incubating sucrose and a glucansucrase from *Leuconostoc* species, preferably from *Leuconostoc mesenteroides* NRRL B-512F, in buffered water at pH convenient for the enzymatic activity (well-known by a skilled man) or in a buffered water at a pH convenient for the enzymatic activity-cosolvent mixture with a phenolic compound having the following formula:

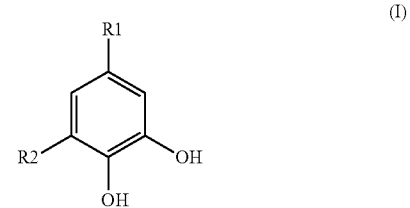

(I)

wherein
R2 is H or OH; and
R1 is selected from the group consisting of

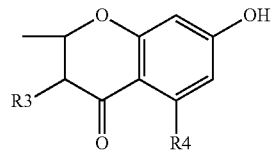

wherein R3 and R4, independently, are H or OH, with the proviso that at least one among R3 and R4 represents OH;

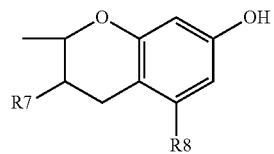

wherein R7 is selected from the group consisting of H, —OH or —OCOR and R8 is H or OH, with the proviso that at least one among R7 and R8 represents OH;

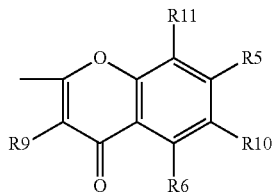

wherein R5 is OH or $OCH_3$, R6 is H or OH, R9 is H or OH, R10 is H, $OCH_3$ or $C_6H_{11}O_5$, and R11 is H, OH or $C_6H_{11}O_5$, with the proviso that R10 and R11 cannot be both H when R5 and R6 are both OH and that when R10 is $C_6H_{11}O_5$, then R11 is H;

—$(CH_2)_n$—COOR or —$(CH_2)_n$—CONHR, with n being an integer from 0 to 2;

—(CR12=CH)—COOR or —(CR12=CH)—CONHR, R12 being H or a $C_1$-$C_6$ linear, branched or cyclic alkyl or alkenyl, preferably methyl, ethyl, propyl, cyclohexyl or phenyl, more preferably methyl or phenyl;

—$(CH_2)_n$—OR or —$(CH_2)_n$—NHR with n being an integer from 0 to 2;

—$(CH_2)_n$—COR or —$(CH=CH)_n$—COR with n being an integer from 0 to 2;

—H;

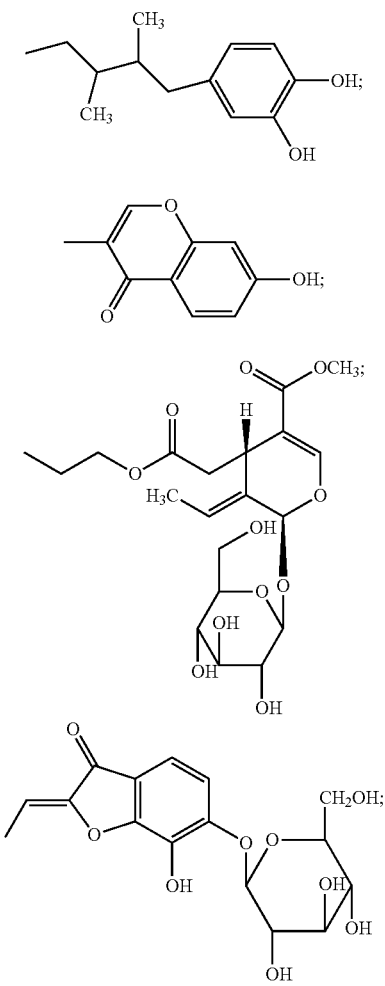

and
a $C_1$-$C_{10}$ hydrocarbon group which forms with the represented ring of formula (I) a fused aromatic ring (bi- or tri-cyclic) together with the ortho carbon of R1;

wherein R is H or a linear, branched or cyclic, aromatic or not, saturated or unsaturated, $C_1$-$C_{10}$ hydrocarbon group, optionally interrupted by at least one heteroatom, wherein said hydrocarbon group comprises an alkyl, an alkenyl or an alkynyl, preferably an alkyl or an alkenyl, which can be substituted by one or several substituents selected from the group consisting of: an ($C_5$-$C_9$)aryl, an ($C_4$-$C_9$)heterocycle, an ($C_1$-$C_3$)alkoxy, an ($C_2$-$C_3$)acyl, an ($C_1$-$C_3$)alcohol, a carboxylic group (—COOH), an ($C_2$-$C_3$)ester, an ($C_1$-$C_3$) amine, an amino group (—$NH_2$), an amide (—$CONH_2$), an ($C_1$-$C_3$)imine, a nitrile, a hydroxyl (—OH), an aldehyde group (—CHO), a halogen, a ($C_1$-$C_3$)halogenoalkyl, a thiol (—SH), a ($C_1$-$C_3$)thioalkyl, a ($C_1$-$C_3$)sulfone, a ($C_1$-$C_3$) sulfoxide and a combination thereof.

In a first embodiment, R2 is H. In this embodiment, the phenolic compound can be, for example, the epicatechin gallate, the eriodictyol, the esculetin, the epicatechin, the fisetin, the fustin, the homoprotocatechuic acid, the protocatechuic acid, the protocatechuic acid ethyl ester, the hydroxytyrosol, the maclurine, the nordihydroguaiaretic acid, the oleuropein, the pyrocatechol, the rhamnetin, the rosmarinic acid, the taxifolin, the 3-hydroxydaidzein, the 3,4-dihydroxybenzophenone, the caffeic acid, the dihydrocaffeic acid, the caffeic acid phenethyl ester, the catechin, the cirsiliol, the chlorogenic acid, the gossypetin, the orientin, the homoorientin, the 3,4-dihydroxybenzaldehyde, the butein, the 3,4-dihydroxyacetophenone, the marein, the maritimein, the eriodictyolchalcone, the 4-methylesculetin, the nordalbergin, the salsolinol, the chicoric acid, the echinacoside, the verbascoside and the anthrarobin.

In an alternative embodiment, R2 is OH. In this embodiment, the phenolic compound can be, for example, the epigallocatechin, the dihydrorobinetin, the gallocatechin, the gallic acid, the propyl gallate, the epigallocatechin gallate, the hamamelitannin and the robinetin.

In a particular embodiment of the method according to the present invention, the phenolic compound has the following formula:

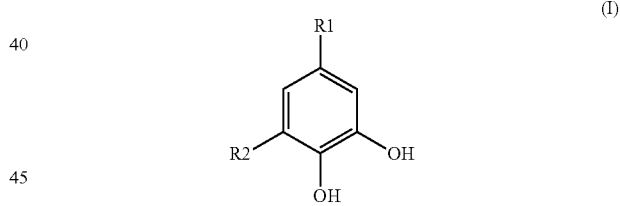

(I)

wherein
R2 is H or OH; and
R1 is

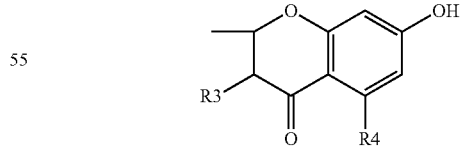

wherein R3 and R4, independently, are H or OH, with the proviso that at least one among R3 and R4 represents OH.

In a preferred embodiment, R3 and R4 are OH. In another preferred embodiment, R3 is H and R4 is OH. In a further preferred embodiment, R3 is OH and R4 is H. In a particularly preferred embodiment, R2 is H and R3/R4 are selected from the following combinations: OH/OH; H/OH; and OH/H. In another preferred embodiment, R2 is OH and R3/R4 are selected from the following combinations: OH/OH; H/OH; and OH/H. Preferably, the phenolic compound is selected from the group consisting of the taxifolin, the eriodictyol, the dihydrorobinetin and the fustin.

In another particular embodiment of the method according to the present invention, the phenolic compound has the following formula:

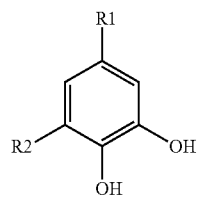

wherein
R2 is H or OH; and
R1 is

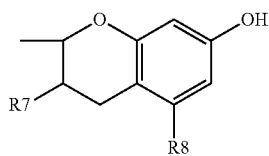

wherein R7 is selected from the group consisting of H, —OH or —OCOR and R8 is H or OH, with the proviso that at least one among R7 and R8 represents OH. In a preferred embodiment, R8 is OH and R7 is OH or OCOR. In a more preferred embodiment, R7 and R8 are both OH. In another preferred embodiment, R7 is —OCOR and R8 is OH. In a particular preferred embodiment, R2 is H and R3/R4 are selected from the following combinations: H/OH, OH/H, OH/OH and OCOR/OH. In another particular preferred embodiment, R2 is OH and R3/R4 are selected from the following combinations: H/OH, OH/H, OH/OH and OCOR/OH. More preferably, R is

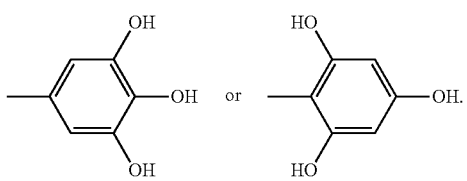

Preferably, the phenolic compound is selected from the group consisting of the catechin, the epicatechin, the catechin gallate, the epicatechin gallate, the gallocatechin, the epigallocatechin, the gallocatechin gallate and the epigallocatechin gallate.

In a further particular embodiment of the method according to the present invention, the phenolic compound has the following formula:

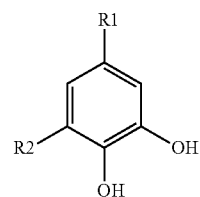

wherein
R2 is H or OH; and
R1 is

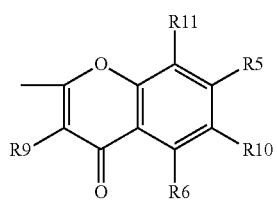

wherein R5 is OH or OCH$_3$, R6 is H or OH, R9 is H or OH, R10 is H, OCH$_3$ or C$_6$H$_{11}$O$_5$, and R11 is H, OH or C$_6$H$_{11}$O$_5$, with the proviso that R10 and R11 cannot be both H when R5 and R6 are both OH and that when R10 is C$_6$H$_{11}$O$_5$, then R11 is H. In particular, R6, R5 and R11 can be selected from the following combinations:
a) R6 is OH and R5 is OCH$_3$ and R11 is H;
b) R6 is OH and R5 is OH and R11 is OH;
c) R6 is OH and R5 is OH and R11 is C$_6$H$_{11}$O$_5$; and
d) R6 is H and R5 is OH and R11 is H; and
R9 is H or OH, and R10 is H or OCH$_3$ or C$_6$H$_{11}$O$_5$, with the proviso that when R10 is C$_6$H$_{11}$O$_5$, R11 is H.

In a preferred embodiment, R9 is OH, R10 is H and R11 is H, whereas R6 is OH and R5 is OCH$_3$ or R6 is H and R5 is OH. Preferably, R2 is H. Alternatively, R2 is OH.

In another preferred embodiment, R9 is H and R10 is OCH$_3$ or C$_6$H$_{11}$O$_5$. In a particular aspect of this embodiment, R9 and R11 are H, R10 and R5 are OCH$_3$ and R6 is OH.

In an additional preferred embodiment, R5 and R6 are both OH, R9 is H or OH, R10 is OH or C$_6$H$_{11}$O$_5$ and R11 is H, OH or C$_6$H$_{11}$O$_5$, with the proviso that when R10 is C$_6$H$_{11}$O$_5$, then R11 is H. In another preferred embodiment, R5 and R6 are both OH, R9 is H or OH, R10 is H and R11 is OH or C$_6$H$_{11}$O$_5$.

In another preferred embodiment, R9 is H and R10 is H. In a further preferred embodiment, R9 is H, R10 and R5 are OCH$_3$ and R6 is OH.

In a particular embodiment, R2, R5, R6, R9, R10 and R11 can be selected from the above-mentioned combinations.

| R2 | R5 | R6 | R9 | R10 | R11 |
|---|---|---|---|---|---|
| H | OCH$_3$ | OH | H | H | H |
| H | OCH$_3$ | OH | H | OCH$_3$ | H |
| H | OCH$_3$ | OH | H | C$_6$H$_{11}$O$_5$ | H |
| H | OCH$_3$ | OH | OH | H | H |
| H | OCH$_3$ | OH | OH | OCH$_3$ | H |
| H | OCH$_3$ | OH | OH | C$_6$H$_{11}$O$_5$ | H |
| H | OH | OH | H | H | OH |
| H | OH | OH | H | OCH$_3$ | OH |
| H | OH | OH | H | C$_6$H$_{11}$O$_5$ | H |
| H | OH | OH | OH | H | OH |

-continued

| R2 | R5 | R6 | R9 | R10 | R11 |
|---|---|---|---|---|---|
| H | OH | OH | OH | OCH$_3$ | OH |
| H | OH | OH | OH | C$_6$H$_{11}$O$_5$ | H |
| H | OH | OH | H | H | C$_6$H$_{11}$O$_5$ |
| H | OH | OH | H | OCH$_3$ | C$_6$H$_{11}$O$_5$ |
| H | OH | OH | H | C$_6$H$_{11}$O$_5$ | H |
| H | OH | OH | OH | H | C$_6$H$_{11}$O$_5$ |
| H | OH | OH | OH | OCH$_3$ | C$_6$H$_{11}$O$_5$ |
| H | OH | OH | OH | C$_6$H$_{11}$O$_5$ | H |
| H | OH | H | H | H | H |
| H | OH | H | H | OCH$_3$ | H |
| H | OH | H | H | C$_6$H$_{11}$O$_5$ | H |
| H | OH | H | OH | H | H |
| H | OH | H | OH | OCH$_3$ | H |
| H | OH | H | OH | C$_6$H$_{11}$O$_5$ | H |
| OH | OCH3 | OH | H | H | H |
| OH | OCH3 | OH | H | OCH$_3$ | H |
| OH | OCH3 | OH | H | C$_6$H$_{11}$O$_5$ | H |
| OH | OCH3 | OH | OH | H | H |
| OH | OCH3 | OH | OH | OCH$_3$ | H |
| OH | OCH3 | OH | OH | C$_6$H$_{11}$O$_5$ | H |
| OH | OH | OH | H | H | OH |
| OH | OH | OH | H | OCH$_3$ | OH |
| OH | OH | OH | H | C$_6$H$_{11}$O$_5$ | H |
| OH | OH | OH | OH | H | OH |
| OH | OH | OH | OH | OCH$_3$ | OH |
| OH | OH | OH | OH | C$_6$H$_{11}$O$_5$ | H |
| OH | OH | OH | H | H | C$_6$H$_{11}$O$_5$ |
| OH | OH | OH | H | OCH$_3$ | C$_6$H$_{11}$O$_5$ |
| OH | OH | OH | H | C$_6$H$_{11}$O$_5$ | H |
| OH | OH | OH | OH | H | C$_6$H$_{11}$O$_5$ |
| OH | OH | OH | OH | OCH$_3$ | C$_6$H$_{11}$O$_5$ |
| OH | OH | OH | OH | C$_6$H$_{11}$O$_5$ | H |
| OH | OH | H | H | H | H |
| OH | OH | H | H | OCH$_3$ | H |
| OH | OH | H | H | C$_6$H$_{11}$O$_5$ | H |
| OH | OH | H | OH | H | H |
| OH | OH | H | OH | OCH$_3$ | H |
| OH | OH | H | OH | C$_6$H$_{11}$O$_5$ | H |

Preferably, the phenolic compound is selected from the group consisting of the rhamnetin, the fisetin, the robinetin, the gossypetin, the orientin, the homoorientin and the cirsiliol.

In a further particular embodiment of the method according to the present invention, the phenolic compound has the following formula:

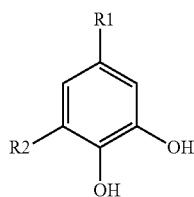
(I)

wherein

R2 is H or OH, and R1 is —(CH$_2$)$_n$—COOR or —(CH$_2$)$_n$—CONHR with n being an integer from 0 to 2. In a preferred embodiment, R2 is H. Alternatively, R2 is OH. Preferably, R is selected from the group consisting of H, a C$_1$-C$_3$ alkyl, preferably methyl, ethyl or propyl, and

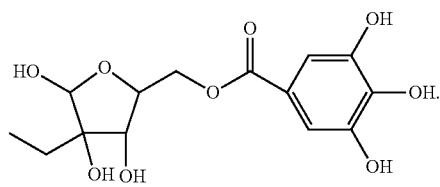 [SMILES: CCC1(O)C(O)OC(COC(=O)c2cc(O)c(O)c(O)c2)C1O]

In a first more preferred embodiment, n is 0 and R is preferably H. In a second more preferred embodiment, n is 1 and R is preferably H. In a third more preferred embodiment, n is 2 and R is preferably H. In another preferred embodiment, n is 0 and R is a C$_1$-C$_3$ alkyl, preferably methyl, ethyl, propyl or

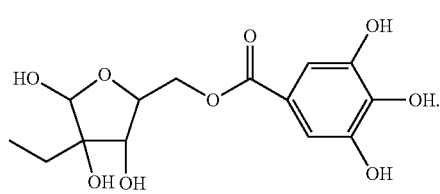 [SMILES: CCC1(O)C(O)OC(COC(=O)c2cc(O)c(O)c(O)c2)C1O]

In a preferred embodiment, R1 is —(CH$_2$)$_n$—COOR. In a preferred embodiment, R is H.

Preferably, the phenolic compound is selected from the group consisting of the homoprotocatchuic acid, the dihydrocaffeic acid, the protocatechuic acid ethyl ester, the propyl gallate, the gallic acid, the hamamelitannin (2',5-di-O-galloyl-hamamelose) and the protocatechuic acid.

In an additional particular embodiment of the method according to the present invention, the phenolic compound has the following formula:

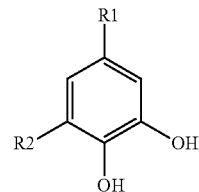
(I)

wherein

R2 is H or OH, and R1 is —(CR12=CH)—COOR or —(CR12=CH)—CONHR, R12 being H or a C$_1$-C$_6$ linear or cyclic alkyl or alkenyl, preferably methyl, ethyl, propyl, cyclohexyl or phenyl, more preferably methyl or phenyl. Preferably R1 is —(CH=CH)—COOR or —(CH=CH)—CONHR. In a preferred embodiment, R2 is H. Alternatively, R2 is OH. In a preferred embodiment, R1 is —(CH=CH)—COOR. In a preferred embodiment, R is selected from the group consisting of H;

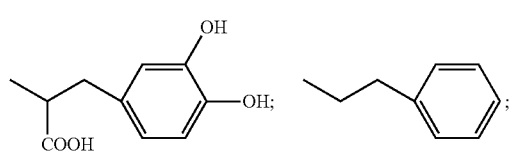

-continued

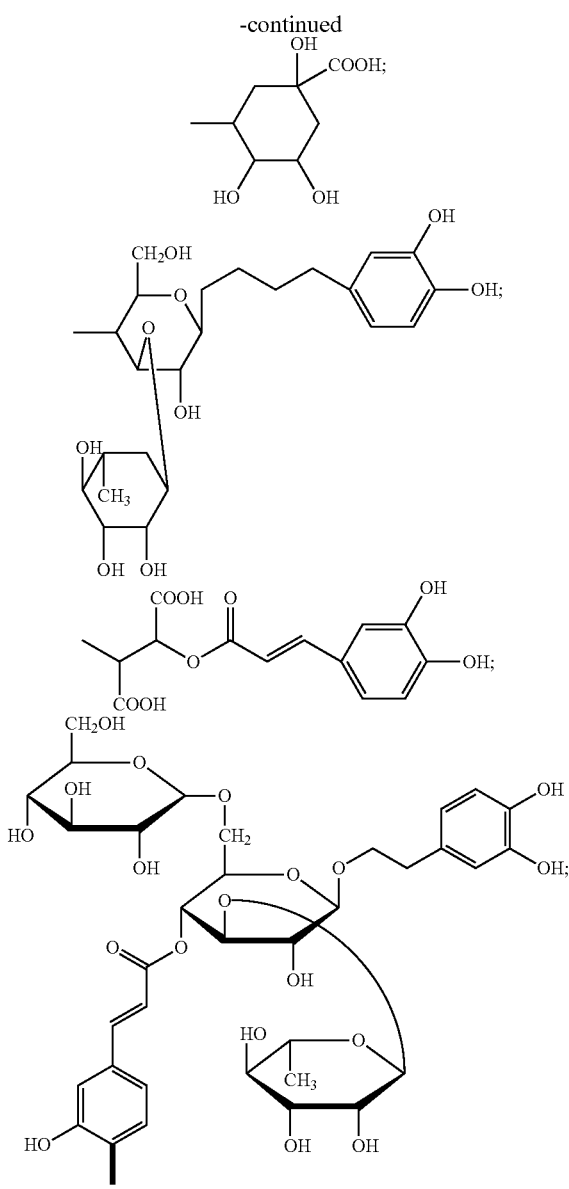

and a bond attached to the phenyl group of formula (I) at the carbon in ortho of R1.

When R is a bond attached to the phenyl group of formula (I) at the carbon in ortho of R1, R12 can be in particular selected from the group consisting of H, methyl and phenyl. Then, the phenolic compound can have the following formula:

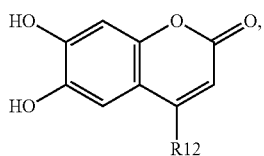

R12 being H or a $C_1$-$C_6$ linear or cyclic alkyl or alkenyl, preferably methyl, ethyl, propyl, cyclohexyl or phenyl, more preferably methyl or phenyl.

Preferably, the phenolic compound is selected from the group consisting of the caffeic acid, the rosmarinic acid, the esculetin, the 4-methylesculetin, the nordalbergin (6,7-dihydroxyphenylcoumarin), the chlorogenic acid, the caffeic acid phenethyl ester, the chicoric acid (dicaffeoyl tartaric acid), the echinacoside (2-(3,4-dihydroxyphenyl)ethyl O-6-deoxy-alpha-L-mannopyranosyl-(1→3)-O-(beta-D-glucopyranosyl-(1→6))-, 4-(3-(3,4-dihydroxyphenyl)-2-propenoate), beta-D-glucopyranoside) and the verbascoside.

In an additional particular embodiment of the method according to the present invention, the phenolic compound has the following formula:

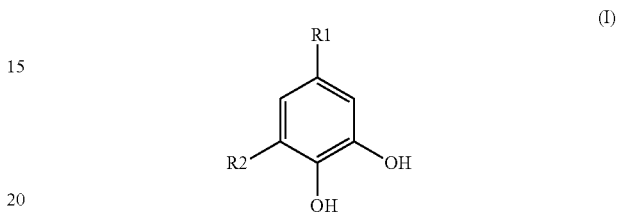

wherein
R2 is H or OH, and R1 is —$(CH_2)_n$—OR with n being an integer from 0 to 2. In a preferred embodiment n is 2. Preferably, the phenolic compound is the hydroxytyrosol.

In an additional particular embodiment of the method according to the present invention, the phenolic compound has the following formula:

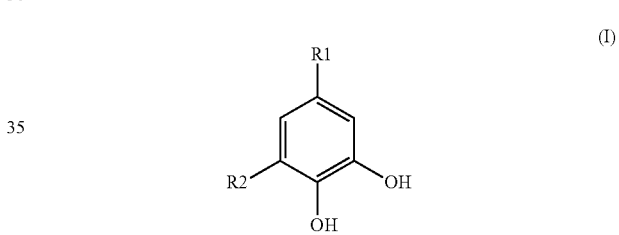

wherein
R2 is H or OH, and R1 is —$(CH_2)_n$—COR or —$(CH=CH)_n$—COR, with n being an integer from 0 to 2.
In a preferred embodiment, n is 0 or 1 and R is selected from the group consisting of H; a $C_1$-$C_3$ alkyl, preferably methyl, ethyl or propyl, more preferably methyl;

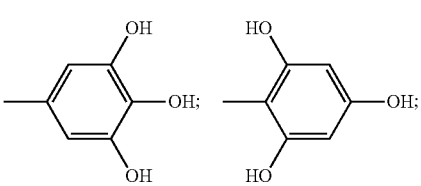

phenyl;

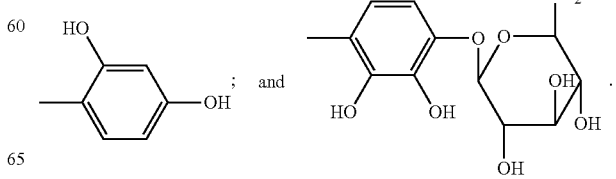

Preferably, n is 0. Alternatively, n is 1.

Preferably, the phenolic compound is selected from the group consisting of the maclurine, the 3,4-dihydroxybenzaldehyde, the 3,4-dihydroxybenzophenone, the butein (2',3,4,4'-tetrahydroxychalcone), the 3,4-dihydroxyacetophenone, the marein (2',3,3',4,4'-pentahydroxy-4'-glucosylchalcone) and the eriodictyolchalcone (2',4',6',3,4-pentahydroxychalcone).

In an additional particular embodiment of the method according to the present invention, the phenolic compound has the following formula:

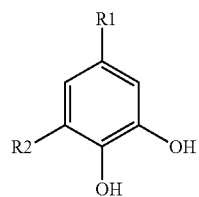

wherein
R2 is H or OH, and R1 is selected from the group consisting of H;

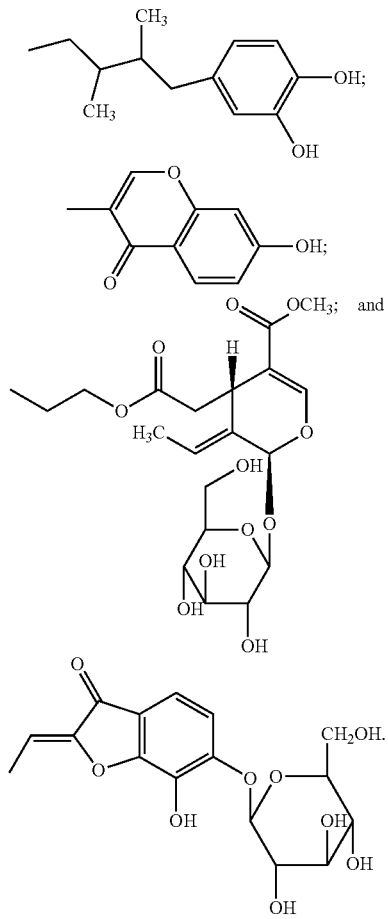

Preferably, the phenolic compound is selected from the group consisting of the pyrocatechol, the nordihydroguaiaretic acid, the 3-hydroxydaidzein, the oleuropein and the maritimein (3',4',6,7-tetrahydroxy-6-O-glucosylaurone).

In this embodiment, R1 of the phenolic compound is a $C_1$-$C_{10}$ hydrocarbon group which forms with the represented ring of formula (I) a fused aromatic ring (bi- or tri-cyclic) together with the ortho carbon of R1. In particular, the phenolic compound can be selected from the group consisting of

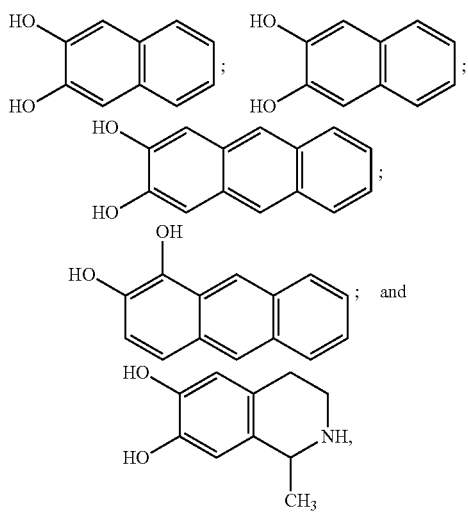

said fused ring can be optionally interrupted by at least one heteroatom and can be substituted by one or several substituents selected from the group consisting of an ($C_1$-$C_3$)alkoxy, an ($C_2$-$C_3$)acyl, an ($C_1$-$C_3$)alcohol, a carboxylic group (—COOH), an ($C_2$-$C_3$)ester, an ($C_1$-$C_3$)amine, an amino group (—NH$_2$), an amide (—CONH$_2$), an ($C_1$-$C_3$) imine, a nitrile, a hydroxyl (—OH), an aldehyde group (—CHO), a halogen, a ($C_1$-$C_3$)halogenoalkyl, a thiol (—SH), a ($C_1$-$C_3$)thioalkyl, a ($C_1$-$C_3$)sulfone, a ($C_1$-$C_3$) sulfoxide and a combination thereof. In a particular preferred embodiment, the phenolic compound is

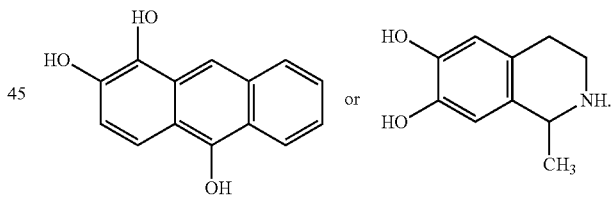

Nature and Source of the Enzyme

The enzymes that can be used for this condensation reaction are glycosyltransferases, more preferably hexosyltransferases (EC 2.4.1), and in a preferred manner glucansucrases (EC 2.4.1.5).

In a preferred embodiment, the enzyme used for the desired condensation of these phenolic compounds with glucose is a glucansucrase from a bacterial species, more precisely from a *Leuconostoc* species and more preferably from *Leuconostoc mesenteroides* NRRL B-512F.

Alternative sources of enzyme may be the glucansucrase(s) from *Leuconostoc mesenteroides* NRRL B-742, *Leuconostoc mesenteroides* NRRL B-1299, *Leuconostoc mesenteroides* NRRL B-1355 or *Leuconostoc mesenteroides* NRRL B-23192.

Such enzymes can be obtained by a natural fermentation of the producing strains followed by cell treatments and enzyme recovery and purification. Since glucansucrases are mainly extracellular large enzymes in solution in the associated culture broth or cells, the techniques that can be used for the recovery of the enzyme include but are not limited to centrifugation and tangential microfiltration and, if it is a cell associated enzyme, the techniques aiming at cell disruption include, but are not limited to, French press homogenization, glass beads, sonication or any equivalent method. The techniques aiming at enzyme concentration include, but are not limited to, ultrafiltration with a molecular weight cut-off ranging from 10 kDa to 300 kDa and the techniques that can be used for enzyme purification include, but are not limited to, phase partition with polyethylene glycol and gel permeation chromatography. An alternative solution consists of the recombinant expression of said enzymes in well-known expression hosts such as E. coli, S. cerevisiae, Baculovirus, Y. lipolytica, Bacillus sp., Pseudomonas sp., H. polymorpha or mammalian cells (see as one reference "Production of Recombinant Proteins: Novel Microbial and Eukaryotic Expression Systems," Wiley 2004—Gerd Gellissen ed.), optionally followed by (a) purification step(s) using well-known methods in the art.

The enzyme can also be obtained through methods well-known from the art: random mutagenesis, directed mutagenesis or directed evolution methods (MIYAZAKI K, ARNOLD F H, (2004), In vitro DNA recombination. In Phage Display: A practical approach. Clarkson T and Lowman H, editors. New York: Oxford University Press Inc., 43-60). These technologies could enable obtaining enzymes with higher specific activity, lower products inhibition, dedicated region, chemo- and stereoselectivity, better stability, or any combination thereof.

The process of the invention can thus be carried out with either whole cells or with natural or recombinant crude or purified enzyme. The enzyme can be used in its "free" form or as an immobilized catalyst. Such immobilisation procedures include but are not limited to gel encapsulation (calcium alginate), resin adsorption, glutaraldehyde reticulation, spray drying in the presence eventually of an adequate adjuvant to obtain an insoluble form of the enzyme, membrane reaction or any combination thereof and are well-known in the art. The choice of one immobilisation approach relies on its economic cost and on the final yield of the process involving said immobilized enzyme.

The amount of enzymatic activity of an enzyme preparation can be estimated using the hydrolysis of sucrose and the measurement of the released reducing sugar (fructose) by means of colorimetric methods (such as the one involving 3,5-dinitro-salycilic acid; SUMNER J B, HOWELL S F (1935) A method for determination of invertase activity. J Biol Chem 108: 51-4). This enzymatic activity is expressed in units, wherein one unit (U) corresponds to the amount of enzyme that releases 1 μmole of fructose per minute at 30° C., pH 5.2 (sucrose: 100 g/L; sodium acetate buffer: 50 mM; calcium chloride dihydrate: 10 mg/L).

Reaction Conditions

The reaction can be achieved in buffered water or in a buffered water/cosolvent(s) mixture. Indeed, the inventors surprisingly observed that the enzyme is able to glucosylate in absence of cosolvents.

Preferably, the buffered water at a pH convenient for the enzymatic activity used either without cosolvent or in a mixture with a cosolvent consists of sodium or potassium acetate buffer at a concentration ranging from 20 to 500 mM in water but any other buffering substance without any negative effect on the enzymatic activity can be used. Preferably, the buffered water at a pH convenient for the enzymatic activity-cosolvent mixture consists of a mixture of water, preferably buffered water as previously described, and dimethyl sulfoxide (DMSO) with a ratio of less than 35% of DMSO (volume/volume), preferably between 15-25%, more preferably about 15%.

The reaction can be achieved in a water/cosolvent(s) mixture that enables both a proper activity of the enzyme and a good level of solubility of the phenolic compounds and of the glucose donor, i.e. sucrose. Such cosolvents can be the following water-miscible organic solvents: dimethyl sulfoxide, dioxane, dimethyl formamide, ethanol, n-propanol, isopropanol, ethylene glycol, glycerol, 1,2-propanediol, sulfolane, tetramethylurea, ethyl-lactate, diethyl ether of diethylene glycol and dimethyl ether of triethylene glycol used at different weight/volume ratios. In addition to these simple organic solvents, ionic liquids (imidazolium, pyridinium, phosphonium and ammonium salts) can also be envisaged. The cosolvents can also be the following water-immiscible organic solvents: ethyl acetate, methyl ethyl ketone, methyl-2 butanol-2 and a combination of water-miscible organic solvent(s) with water-immiscible organic solvent(s).

In a preferred embodiment, the mixture is made of water and dimethyl sulfoxide (DMSO), with DMSO concentrations ranging from 5 to 70% (volume/volume). In a preferred embodiment, DMSO concentrations are between 5 and 50% (volume/volume). In a most preferred embodiment, DMSO concentration is between 10 and 35% (volume/volume). Indeed, the inventors surprisingly found that the reaction is much more efficient when proceeding at a ratio of DMSO lower than 40%. The highest rate of product has been registered for a ratio of 15%. Therefore, a preferred ratio of the method according to the present invention is comprised between 15 and 25%, preferably about 15% (+/−3%).

Each phenolic compound is incubated in this reaction mixture with sucrose and the enzyme in pH and temperature conditions that allow the enzyme to be active and to synthesize the maximum possible amount of desired glucoside. Preferably, the reaction medium contains, in addition, calcium cations in the form of calcium chloride (or in the form of any water-soluble salt of calcium) to improve the stability of the enzyme. The condensation reaction can be performed at a pH ranging from 4 to 8, and preferably from 5 to 7, by introducing a low amount of acetate buffer in the reaction medium. The temperature of the synthesis medium is maintained at a value ranging from 10 to 40 degrees Celsius, and preferably approximately 25 to 33 degrees Celsius.

Typical reaction conditions with the glucansucrase from Leuconostoc mesenteroides NRRL B-512F consist of a mixture of acetate buffer at 10 mM to 100 mM, DMSO at 10 to 35% (volume/volume), sucrose at 100 mM to 900 mM, phenolic compound at 2 to 200 mM, calcium salts at 0.5 mg to 1 g/l and the enzyme for a final concentration of 0.5 to 5 U/ml. This reaction is incubated at 30° C. for several hours (e.g., 10 to 48 hours) and the synthesis of the phenolic compound derivative, as well as the disappearance of said phenolic compound over time, is followed by HPLC analysis. A better characterization of the products can be achieved by high-performance liquid chromatography coupled with a photodiode array detector coupled with a mass spectrometer to directly estimate the number of glucose moieties attached to the phenolic compound and thus have a good analytical characterization of the synthesized derivatives.

In one embodiment of the present invention, such conditions allowing the analytical characterization of the synthesized derivatives can be as follows:

The synthesis media can be analyzed by high-performance liquid chromatography coupled with a photodiode array detector (PDA Waters® 996) and a mass spectrometer (Micromass ZQ 2000, Waters®).

i) Operating Conditions for Chromatography:
Column: KROMASIL C18 5μ, 250 mm×4.6 mm (reference: K2185; A.I.T. Chromato, 117 rue de Stalingrad, 78800 Houilles)
Elution (method 1):
solvent A: deionized water containing 1% v/v acetic acid
solvent B: HPLC-grade methanol containing 1% v/v acetic acid
0 to 10 minutes: 90% to 80% A (linear); 10% to 20% B (linear); 1 ml/minute
10 to 25 minutes: 80% to 50% A (linear); 20% to 50% B (linear); 1 ml/minute
25 to 30 minutes: 50% A; 50% B; 1 ml/minute
30 to 35 minutes: 50% to 90% A (linear); 50% to 10% B (linear); 1 ml/minute
45 minutes: next injection
Column temperature: 30° C.
Injection volume: 10 μL
ii) Photodiode Array Detector
Start wavelength: 210 nm
End wavelength: 400 nm
Resolution: 1.2 nm
Sampling rate: 1 spectra/second
iii) LC Mass Spectrometer (Single Quadripole)
Ionisation: electrospray in negative mode
Spray voltage: 3.0 kV
Source temperature: 150° C.
Cone tension: 20 or 40 V
Extractor: 3.0 V
Desolvation temperature: 300° C.
Cone gas flow: 30 L/hour
Desolvation gas flow: 600 L/hour
Full scan mass spectra: m/z from 100 to 2000
Purification After synthesis, phenolic compound O-α-glucosides can be either used directly or purified to reach a desired purity in terms of residues of non-transformed phenolic compound, sugars, enzyme and cosolvents.

For example, the phenolic compound O-α-glucosides can be adsorbed on a synthetic macroporous adsorbent resin by taking advantage of the difference of absorbing ability of substances. Due to the presence of residual substances in the interstitial volume, the resin with the adsorbed phenolic substances is washed with water in order to completely flush out the enzyme, the sugars, the polysaccharide and the co-solvent. Then the resin can undergo an elution step with an appropriate solvent to recover the synthesized product. The appropriate solvent is pure methanol, ethanol, n-propanol, 2-propanol, acetone or a mixture of them, or a mixture of them with water with no more than 20% volume/volume water. The solution containing the synthesized product(s) can be concentrated by evaporation under vacuum at a moderate temperature (not higher than 50° C.) or with compatible membrane equipment for further purification, or directly used for further purification. Further purification steps such as liquid/liquid extraction, preparative HPLC or other rounds of resin purification can be used to attain the required level of purity for the final application. Organic solvents that can be used for liquid-liquid extraction are ethyl acetate, butyl acetate, and methyl ethyl ketone, depending on the solubility difference of the phenolic compound and phenolic compound glucoside.

Finally, a syrup containing the desired substance(s) can be obtained by removing the solvent (water or organic solvent) by evaporation under vacuum at a moderate temperature (not higher than 50° C.) or with compatible membrane equipment and concentrating the resulting solution to give a prescribed concentration. This syrup can be dried (freeze drying, spray drying or any other way of drying that will preserve the integrity of the molecules) to obtain a powder.

The synthetic macroporous adsorbent resin can be used either in a tank (a sieve with a convenient mesh depending on the resin granulometry will be used to recover the resin) or located in a column fed with a pump. "Synthetic macroporous adsorbent resin" is understood to mean non-ionic and porous synthetic resins which have a relatively large surface area, such as those containing styrene-divinyl benzene copolymer, phenol-formaldehyde polymers, acrylic polymer and methacrylic polymer. Examples of such resins are Amberlite of the XAD type (Rohm and Haas Company, USA) and Diaion of the HP family (Mitsubishi Chemical Industries, Japan).

The invention relates to O-α-glucosides of phenolic compounds containing a catechol structure and for instance selected from protocatechuic acid and its ester derivatives, caffeic acid and its ester derivatives, especially rosmarinic acid, chlorogenic acid, caffeic acid phenethyl ester and hydrocaffeic acid or 3,4-dihydroxyhydrocinnamic acid, 3,4-dihydroxyphenylacetic acid and 3,4-dihydroxyphenylglycol, esculetin, taxifolin, fustin, eriodictyol, fisetin and rhamnetin. In particular, the invention relates to O-α-glucosides of phenolic compounds containing a catechol structure and selected from the group consisting of the epicatechin gallate, the eriodictyol, the esculetin, the fisetin O-α-glucoside, the fustin, the homoprotocatechuic acid, the protocatechuic acid, the protocatechuic acid ethyl ester, the hydroxytyrosol, the maclurine, the nordihydroguaiaretic acid, the oleuropein, the pyrocatechol, the rhamnetin, the rosmarinic acid, the taxifolin, the 3-hydroxydaidzein, the 3,4-dihydroxybenzophenone, the caffeic acid, the dihydrocaffeic acid, the caffeic acid phenethyl ester, the cirsiliol, the chlorogenic acid coside, the anthrarobin, the epigallocatechin, the dihydrorobinetin, the gallocatechin, the gallic acid, the propyl gallate and the robinetin. These new phenolic compound derivatives have better bioavailability through improved solubility in water and/or on in situ release of the aglycones during their usage through their hydrolysis by human natural microbiotes and more specifically human skin microorganisms, or by a selected α-glucosidase such as the α-glucosidase produced by the yeast *Saccharomyces cerevisiae*.

In particular, the present invention concerns a phenolic compound O-α-glucoside having the following formula:

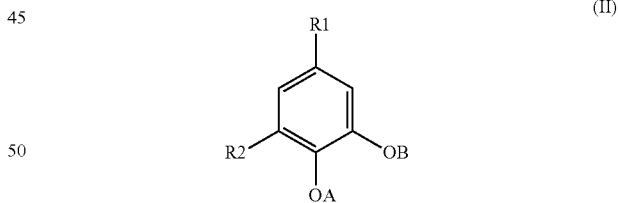

(II)

wherein
A and B, identical or different, are H or an -α-glucosyl residue, with the proviso that at least one of A and B is an -α-glucosyl residue;
R2 is H or OH; and
R1 is selected from the group consisting of

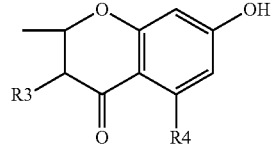

wherein R3 and R4, independently, are H or OH, with the proviso that at least one among R3 and R4 represents OH;

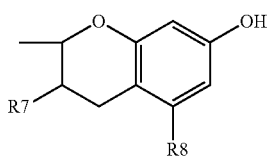

wherein R7 is selected from the group consisting of H, —OH or —OCOR and R8 is H or OH, with the proviso that, when R2 is H, R7 and R8 are not both OH and at least one among R7 and R8 is OH;

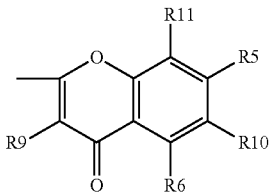

wherein R5 is OH or OCH$_3$, R6 is H or OH, R9 is H or OH, R10 is H, OCH$_3$ or C$_6$H$_{11}$O$_5$ and R11 is H, OH or C$_6$H$_{11}$O$_5$, with the proviso that R10 and R11 cannot be both H when R5 and R6 are both OH and that when R10 is C$_6$H$_{11}$O$_5$, then R11 is H;
- —(CH$_2$)$_n$—COOR or —(CH$_2$)$_n$—CONHR, with n being an integer from 0 to 2;
- —(CR12=CH)—COOR or —(CR12=CH)—CONHR, R12 being H or a C$_1$-C$_6$ linear, branched or cyclic alkyl or alkenyl, preferably methyl, ethyl, propyl, cyclohexyl or phenyl, more preferably methyl or phenyl;
- —(CH$_2$)$_n$—OR or —(CH$_2$)$_n$—NHR with n being an integer from 0 to 2;
- —(CH$_2$)$_n$—COR or —(CH=CH)$_n$—COR with n being an integer from 0 to 2;
- H;

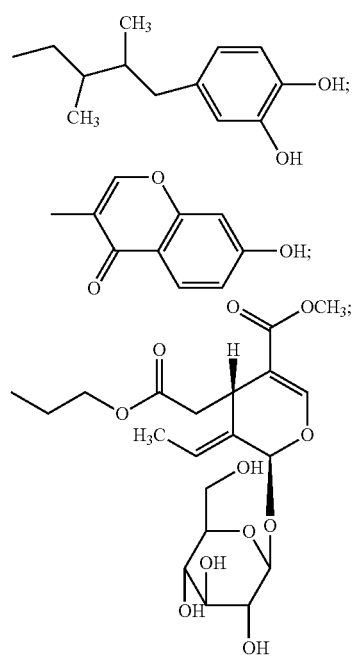

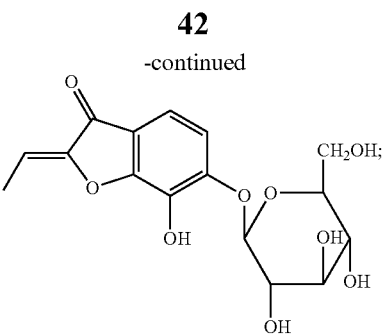

and
a C$_1$-C$_{10}$ hydrocarbon group which forms with the represented ring of formula (I) a fused ring (bi- or tricyclic) together with the ortho carbon of R1, said ring being optionally interrupted by at least one heteroatom;
wherein R is H or a linear, branched or cyclic, aromatic or not, saturated or unsaturated, C$_1$-C$_{10}$ hydrocarbon group, optionally interrupted by at least one heteroatom, wherein said hydrocarbon group comprises an alkyl, an alkenyl or an alkynyl, preferably an alkyl or an alkenyl, which can be substituted by one or several substituents selected from the group consisting of: an (C$_5$-C$_9$)aryl, an (C$_4$-C$_9$)heterocycle, an (C$_1$-C$_3$)alkoxy, an (C$_2$-C$_3$)acyl, an (C$_1$-C$_3$)alcohol, a carboxylic group (—COOH), an (C$_2$-C$_3$)ester, an (C$_1$-C$_3$) amine, an amino group (—NH$_2$), an amide (—CONH$_2$), an (C$_1$-C$_3$)imine, a nitrile, a hydroxyl (—OH), an aldehyde group (—CHO), a halogen, a (C$_1$-C$_3$)halogenoalkyl, a thiol (—SH), a (C$_1$-C$_3$)thioalkyl, a (C$_1$-C$_3$)sulfone, a (C$_1$-C$_3$) sulfoxide and a combination thereof.

In a first embodiment, R2 is H. In this embodiment, the phenolic compound O-α-glucoside can be, for example, the epicatechin gallate O-α-glucoside, the eriodictyol O-α-glucoside, the esculetin O-α-glucoside, the fisetin O-α-glucoside, the fustin O-α-glucoside, the homoprotocatechuic acid O-α-glucoside, the protocatechuic acid O-α-glucoside, the protocatechuic acid ethyl ester O-α-glucoside, the hydroxytyrosol O-α-glucoside, the maclurine O-α-glucoside, the nordihydroguaiaretic acid O-α-glucoside, the oleuropein O-α-glucoside, the pyrocatechol O-α-glucoside, the rhamnetin O-α-glucoside, the rosmarinic acid O-α-glucoside, the taxifolin O-α-glucoside, the 3-hydroxydaidzein O-α-glucoside, the 3,4-dihydroxybenzophenone O-α-glucoside, the caffeic acid O-α-glucoside, the dihydrocaffeic acid O-α-glucoside, the caffeic acid phenethyl ester O-α-glucoside, the cirsiliol O-α-glucoside, the chlorogenic acid O-α-glucoside and the anthrarobin O-α-glucoside.

In an alternative embodiment, R2 is OH. In this embodiment, the phenolic compound O-α-glucoside can be, for example, the epigallocatechin O-α-glucoside, the dihydrorobinetin O-α-glucoside, the gallocatechin O-α-glucoside, the gallic acid O-α-glucoside, the propyl gallate O-α-glucoside and the robinetin O-α-glucoside.

In a particular embodiment of the present invention, the phenolic compound O-α-glucoside has the following formula:

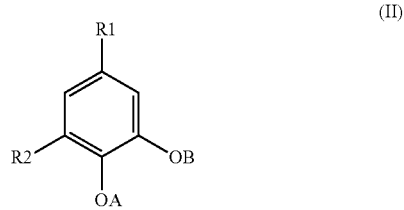

(II)

wherein

A and B, identical or different, are H or a -α-glucosyl residue, with the proviso that at least one of A and B is a -α-glucosyl residue;

R2 is H or OH; and

R1 is

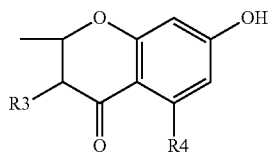

wherein R3 and R4, independently, are H or OH, with the proviso that at least one among R3 and R4 represents OH.

In a particular embodiment, R2 is H. In another embodiment, R2 is OH.

In a preferred embodiment, R3 and R4 are OH. In another preferred embodiment, R3 is H and R4 is OH. In a further preferred embodiment, R3 is OH and R4 is H. In a particularly preferred embodiment, R2 is H and R3/R4 are selected from the following combinations: OH/OH; H/OH; and OH/H. In another preferred embodiment, R2 is OH and R3/R4 are selected from the following combinations: OH/OH; H/OH; and OH/H.

In particular, R2 is H, R3 is H and R4 is OH (resulting in eriodictyol O-α-glucoside). Alternatively, R2 is H, R3 is OH and R4 is H (resulting in fustin O-α-glucoside). In a preferred embodiment, R2 is H and both R3 and R4 are OH (resulting in taxofolin O-α-glucoside).

Preferably, the phenolic compound O-α-glucoside is selected from the group consisting of the taxifolin O-α-glucoside, the eriodictyol O-α-glucoside, the dihydrorobinetin O-α-glucoside and the fustin O-α-glucoside.

In another particular embodiment of the present invention, the phenolic compound O-α-glucose has the following formula:

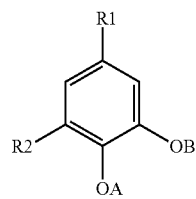

wherein

A and B, identical or different, are H or a -α-glucosyl residue, with the proviso that at least one of A and B is an -α-glucosyl residue;

R2 is H or OH; and

R1 is

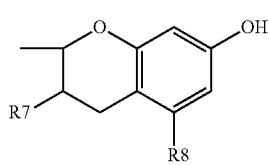

wherein R7 is selected from the group consisting of H, —OH or —OCOR and R8 is H or OH, with the proviso that, when R2 is H, R7 and R8 are not both OH and at least one among R7 and R8 represents OH.

In a particular embodiment, R2 is H. In another embodiment, R2 is OH.

In a preferred embodiment, R2 is OH, R8 is OH and R7 is OH or OCOR. In a more preferred embodiment, R7 and R8 are both OH. In another preferred embodiment, R2 is H, R8 is OH and R7 is OCOR. In a further preferred embodiment, R2 is H or OH, R7 is —OCOR and R8 is OH. More preferably, R is

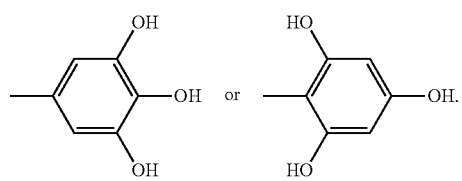

Preferably, the phenolic compound O-α-glucose is selected from the group consisting of the epigallocatechin O-α-glucose, the gallocatechin O-α-glucose and the epicatechin gallate O-α-glucose.

In a further particular embodiment of the present invention, the phenolic compound O-α-glucose has the following formula:

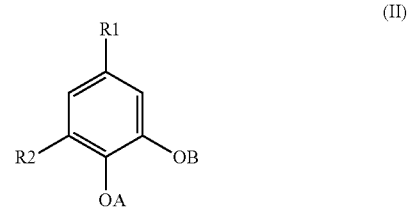

wherein

A and B, identical or different, are H or a -α-glucosyl residue, with the proviso that at least one of A and B is a -α-glucosyl residue;

R2 is H or OH; and

R1 is

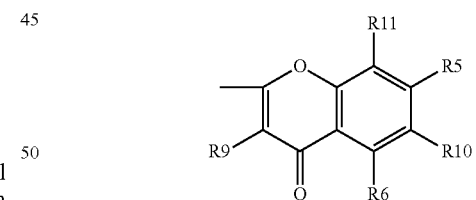

wherein R5 is OH or OCH$_3$, R6 is H or OH, R9 is H or OH, R10 is H, OCH$_3$ or C$_6$H$_{11}$O$_5$ and R11 is H, OH or C$_6$H$_{11}$O$_5$, with the proviso that R10 and R11 cannot be both H when R5 and R6 are both OH and that when R10 is C$_6$H$_{11}$O$_5$, then R11 is H. In particular, R6, R5 and R11 can be selected from the following combinations:

a) R6 is OH and R5 is OCH$_3$ and R11 is H;
b) R6 is OH and R5 is OH and R11 is OH;
c) R6 is OH and R5 is OH and R11 is C$_6$H$_{11}$O$_5$; and
d) R6 is H and R5 is OH and R11 is H; and R9 is H or OH, and R10 is H or OCH$_3$ or C$_6$H$_{11}$O$_5$, with the proviso that when R10 is C$_6$H$_{11}$O$_5$, R11 is H.

In a particular embodiment, R2 is H. In another embodiment, R2 is OH.

In a preferred embodiment, R9 is OH, R10 is H and R11 is H, whereas R6 is OH and R5 is OCH$_3$ or R6 is H and R5 is OH. Preferably, R2 is H. Alternatively, R2 is OH.

In another preferred embodiment, R9 is H and R10 is OCH$_3$ or C$_6$H$_{11}$O$_5$. In a particular aspect of this embodiment, R9 and R11 are H, R10 and R5 are OCH$_3$ and R6 is OH.

In an additional preferred embodiment, R5 and R6 are both OH, R9 is H or OH, R10 is OH or C$_6$H$_{11}$O$_5$ and R11 is H, OH or C$_6$H$_{11}$O$_5$, with the proviso that when R10 is C$_6$H$_{11}$O$_5$ then R11 is H. In another preferred embodiment, R5 and R6 are both OH, R9 is H or OH, R10 is H and R11 is OH or C$_6$H$_{11}$O$_5$.

In another preferred embodiment, R9 is H and R10 is H. In a further preferred embodiment, R9 is H, R10 and R5 are OCH$_3$ and R6 is OH.

In a particular embodiment, R2, R5, R6, R9, R10 and R11 can be selected from the above-mentioned combinations.

| R2 | R5 | R6 | R9 | R10 | R11 |
|----|----|----|----|-----|-----|
| H | OCH$_3$ | OH | H | H | H |
| H | OCH$_3$ | OH | H | OCH$_3$ | H |
| H | OCH$_3$ | OH | H | C$_6$H$_{11}$O$_5$ | H |
| H | OCH$_3$ | OH | OH | H | H |
| H | OCH$_3$ | OH | OH | OCH$_3$ | H |
| H | OCH$_3$ | OH | OH | C$_6$H$_{11}$O$_5$ | H |
| H | OH | OH | H | H | OH |
| H | OH | OH | H | OCH$_3$ | OH |
| H | OH | OH | H | C$_6$H$_{11}$O$_5$ | H |
| H | OH | OH | OH | H | OH |
| H | OH | OH | OH | OCH$_3$ | OH |
| H | OH | OH | OH | C$_6$H$_{11}$O$_5$ | H |
| H | OH | OH | H | H | C$_6$H$_{11}$O$_5$ |
| H | OH | OH | H | OCH$_3$ | C$_6$H$_{11}$O$_5$ |
| H | OH | OH | H | C$_6$H$_{11}$O$_5$ | H |
| H | OH | OH | OH | H | C$_6$H$_{11}$O$_5$ |
| H | OH | OH | OH | OCH$_3$ | C$_6$H$_{11}$O$_5$ |
| H | OH | OH | OH | C$_6$H$_{11}$O$_5$ | H |
| H | OH | H | H | H | H |
| H | OH | H | H | OCH$_3$ | H |
| H | OH | H | H | C$_6$H$_{11}$O$_5$ | H |
| H | OH | H | OH | H | H |
| H | OH | H | OH | OCH$_3$ | H |
| H | OH | H | OH | C$_6$H$_{11}$O$_5$ | H |
| OH | OCH3 | OH | H | H | H |
| OH | OCH3 | OH | H | OCH$_3$ | H |
| OH | OCH3 | OH | H | C$_6$H$_{11}$O$_5$ | H |
| OH | OCH3 | OH | OH | H | H |
| OH | OCH3 | OH | OH | OCH$_3$ | H |
| OH | OCH3 | OH | OH | C$_6$H$_{11}$O$_5$ | H |
| OH | OH | OH | H | H | OH |
| OH | OH | OH | H | OCH$_3$ | OH |
| OH | OH | OH | H | C$_6$H$_{11}$O$_5$ | H |
| OH | OH | OH | OH | H | OH |
| OH | OH | OH | OH | OCH$_3$ | OH |
| OH | OH | OH | OH | C$_6$H$_{11}$O$_5$ | H |
| OH | OH | OH | H | H | C$_6$H$_{11}$O$_5$ |
| OH | OH | OH | H | OCH$_3$ | C$_6$H$_{11}$O$_5$ |
| OH | OH | OH | H | C$_6$H$_{11}$O$_5$ | H |
| OH | OH | OH | OH | H | C$_6$H$_{11}$O$_5$ |
| OH | OH | OH | OH | OCH$_3$ | C$_6$H$_{11}$O$_5$ |
| OH | OH | OH | OH | C$_6$H$_{11}$O$_5$ | H |
| OH | OH | H | H | H | H |
| OH | OH | H | H | OCH$_3$ | H |
| OH | OH | H | H | C$_6$H$_{11}$O$_5$ | H |
| OH | OH | H | OH | H | H |
| OH | OH | H | OH | OCH$_3$ | H |
| OH | OH | H | OH | C$_6$H$_{11}$O$_5$ | H |

In a particular embodiment, R2 is H and R1 is

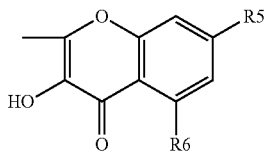

wherein either R6 is OH and R5 is OCH3 (resulting in rhamnetin O-α-glucoside) or R6 is H and R5 is OH (resulting in fisetin O-α-glucoside).

Preferably, the phenolic compound O-α-glucose is selected from the group consisting of the rhamnetin O-α-glucose, the fisetin O-α-glucose, the robinetin O-α-glucose, the gossypetin O-α-glucose, the orientin O-α-glucose, the homoorientin O-α-glucose and the cirsiliol O-α-glucose.

In a further particular embodiment of the present invention, the phenolic compound O-α-glucose has the following formula:

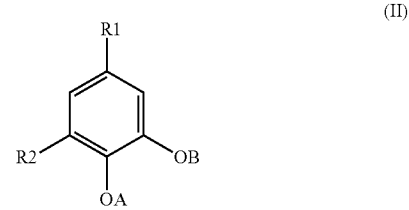

(II)

wherein

A and B, identical or different, are H or a α-glucosyl residue, with the proviso that at least one of A and B is a α-glucosyl residue;

R2 is H or OH; and

R1 is —(CH$_2$)$_n$—COOR or —(CH$_2$)$_n$—CONHR, with n being an integer from 0 to 2.

In a particular embodiment, R2 is H. In another embodiment, R2 is OH.

Preferably, R is selected from the group consisting of H, a C$_1$-C$_3$ alkyl, preferably methyl, ethyl or propyl, and

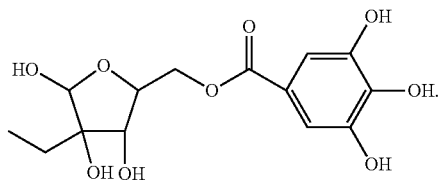 [SMILES: CCC1(O)C(O)OC(COC(=O)c2cc(O)c(O)c(O)c2)C1O]

In a first more preferred embodiment, n is 0 and R is preferably H. In a second more preferred embodiment, n is 1 and R is preferably H. In a third more preferred embodiment, n is 2 and R is preferably H. In another preferred embodiment, n is 0 and R is a C$_1$-C$_3$ alkyl, preferably methyl, ethyl or propyl or

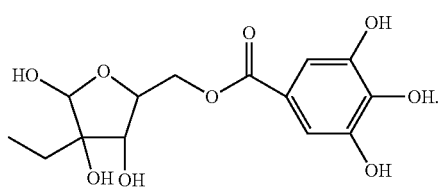 [SMILES: CCC1(O)C(O)OC(COC(=O)c2cc(O)c(O)c(O)c2)C1O]

In a preferred embodiment, R1 is —(CH$_2$)$_n$—COOR. In a preferred embodiment, R is H.

Preferably, the phenolic compound is selected from the group consisting of the homoprotocatechuic acid, the dihydrocaffeic acid, the protocatechuic acid ethyl ester, the propyl gallate, the gallic acid, the hamamelitannin (2',5-di-O-galloyl-hamamelose) and the protocatechuic acid.

In a particular embodiment, R2 is H and R1 is —COOH (resulting in protocatechuic acid O-α-glucoside). In another particular embodiment, R2 is H and R1 is —(CH$_2$)$_2$—COOH (resulting in hydrocaffeic acid O-α-glucoside).

The present invention contemplates the ester thereof and the pharmaceutically acceptable salts thereof.

Preferably, the phenolic compound is selected from the group consisting of the homoprotocatechuic acid O-α-glucoside, the dihydrocaffeic acid O-α-glucoside, the protocatechuic acid ethyl ester O-α-glucoside, the propyl gallate O-α-glucoside, the gallic acid O-α-glucoside, the hamamelitannin (2',5-di-O-galloyl-hamamelose) O-α-glucoside and the protocatechuic acid O-α-glucoside.

In an additional particular embodiment of the present invention, the phenolic compound O-α-glucose has the following formula:

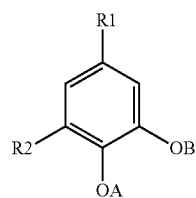

(II)

wherein

A and B, identical or different, are H or a α-glucosyl residue, with the proviso that at least one of A and B is a α-glucosyl residue;

R2 is H or OH; and

R1 —(CR12=CH)—COOR or —(CR12=CH)—CONHR, R12 being H or a C$_1$-C$_6$ linear or cyclic alkyl or alkenyl, preferably methyl, ethyl, propyl, cyclohexyl or phenyl, more preferably methyl or phenyl. Preferably R1 is —(CH=CH)—COOR or —(CH=CH)—CONHR. In a preferred embodiment, R2 is H. Alternatively, R2 is OH. In a preferred embodiment, R1 is —(CH=CH)—COOR. In a preferred embodiment, R is selected from the group consisting of H;

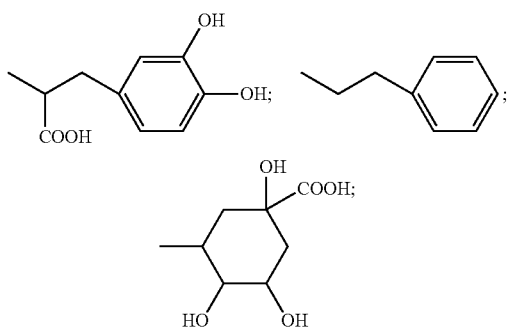

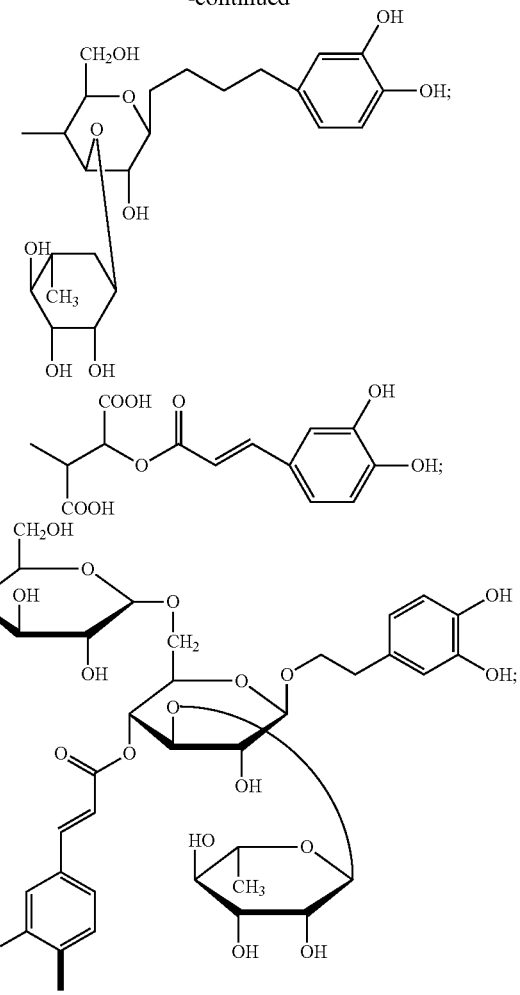

and a bond attached to the phenyl group of formula (I) at the carbon in ortho of R1.

In a particular embodiment, R2 is H and R1 is —(CH=CH)—COOH (resulting in caffeic acid O-α-glucoside). The present invention contemplates the ester thereof and the pharmaceutically acceptable salts thereof. In particular, when R1 is —(CH=CH)—COOR, R is selected from 1,3,4,5-tetrahydroxycyclohexanecarboxylic acid and being attached at position 3 (resulting in chlorogenic acid O-α-glucoside), (R)-1-carboxy-2-(3,4-dihydroxyphenyl)ethyl (resulting in rosmarinic acid O-α-glucoside) and phenethyl (resulting in caffeic acid phenethyl ester O-α-glucoside). In particular, when R1 is —(CR12=CH)—COOR, R is a bond attached to the phenyl group of formula (II) by the carbon in meta of OB, giving the following formula:

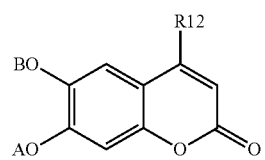

(i.e., when R12 is H, then esculetin O-α-glucoside, when R12 is methyl, then 4-methylesculetin O-α-glucoside and when R12 is phenyl, then nordalbergin O-α-glucoside). In a particular embodiment, R12 is H.

Preferably, the phenolic compound O-α-glucose is selected from the group consisting of the caffeic acid O-α-glucoside, the rosmarinic acid O-α-glucoside, the esculetin O-α-glucoside, the 4-methylesculetin O-α-glucoside, the nordalbergin (6,7-dihydroxyphenylcoumarin) O-α-glucoside, the chlorogenic acid O-α-glucoside, the caffeic acid phenethyl ester O-α-glucoside, the chicoric acid (dicaffeoyl tartaric acid) O-α-glucoside, the echinacoside (2-(3,4-dihydroxyphenyl)ethyl O-6-deoxy-alpha-L-mannopyranosyl-(1→3)-O-(beta-D-glucopyranosyl-(1→6))-, 4-(3-(3,4-dihydroxyphenyl)-2-propenoate) O-α-glucoside, beta-D-glucopyranoside O-α-glucoside and the verbascoside O-α-glucoside.

In an additional particular embodiment of the present invention, the phenolic compound O-α-glucose has the following formula:

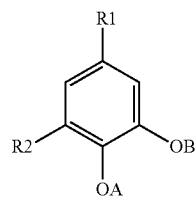
(II)

wherein

A and B, identical or different, are H or a α-glucosyl residue, with the proviso that at least one of A and B is a α-glucosyl residue;
R2 is H or OH; and
R1 is —(CH$_2$)$_n$—OR, with n being an integer from 0 to 2.

In a particular embodiment, R2 is H. In another embodiment, R2 is OH.

In a preferred embodiment n is 2. Preferably, the phenolic compound O-α-glucoside is the hydroxytyrosol O-α-glucoside.

In an additional particular embodiment of the present invention, the phenolic compound O-α-glucoside has the following formula:

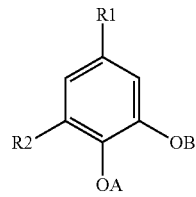
(II)

wherein

A and B, identical or different, are H or a α-glucosyl residue, with the proviso that at least one of A and B is a α-glucosyl residue;
R2 is H or OH; and
R1 is —(CH$_2$)$_n$—COR or —(CH=CH)$_n$—COR, with n being an integer from 0 to 2.

In a particular embodiment, R2 is H. In another embodiment, R2 is OH.

In a preferred embodiment, n is 0 or 1 and R is selected from the group consisting of H; a C$_1$-C$_3$ alkyl, preferably methyl, ethyl or propyl, more preferably a methyl;

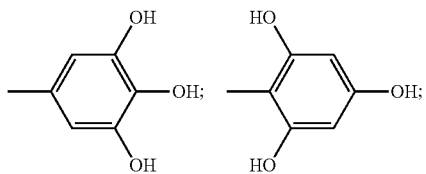
phenyl;

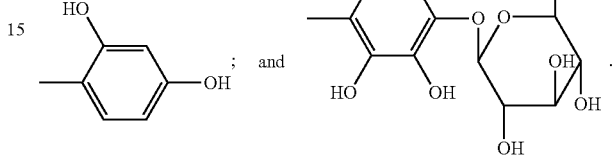
; and

Preferably, n is 0. Alternatively, n is 1.

Preferably, the phenolic compound O-α-glucoside is selected from the group consisting of the maclurine O-α-glucoside, the 3,4-dihydroxybenzaldehyde O-α-glucoside, the 3,4-dihydroxybenzophenone O-α-glucoside, the butein (2',3,4,4'-tetrahydroxychalcone) O-α-glucoside, the 3,4-dihydroxyacetophenone O-α-glucoside, the marein (2',3,3',4, 4'-pentahydroxy-4'-glucosylchalcone) O-α-glucoside and the eriodictyolchalcone (2',4',6',3,4-pentahydroxychalcone) O-α-glucoside.

In an additional particular embodiment of the present invention, the phenolic compound O-α-glucoside has the following formula:

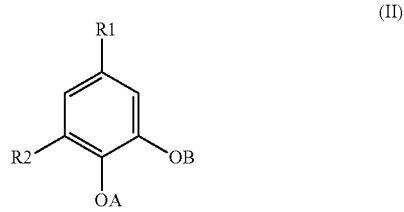
(II)

wherein

A and B, identical or different, are H or a α-glucosyl residue, with the proviso that at least one of A and B is a α-glucosyl residue;
R2 is H or OH; and
R1 is selected from the group consisting of H;

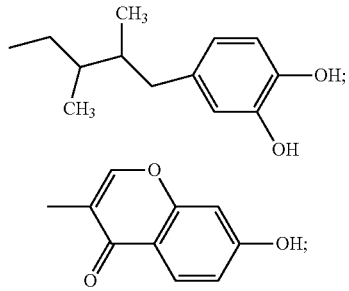

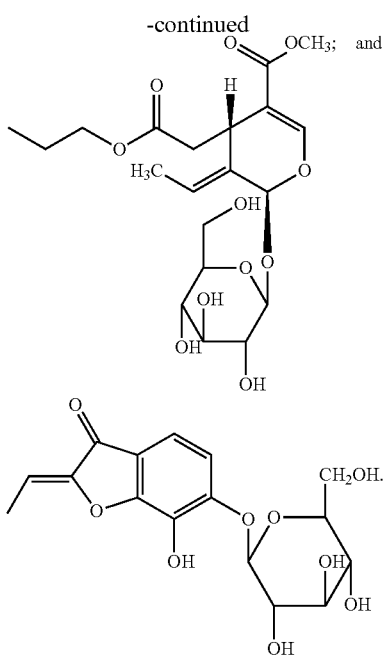

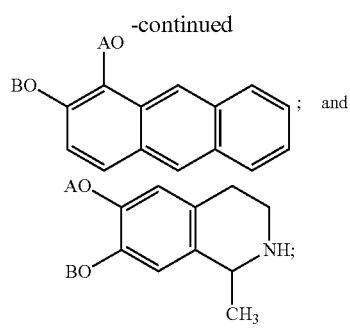

Preferably, the phenolic compound O-α-glucoside is selected from the group consisting of the oleuropein O-α-glucoside, the nordihydroguaiaretic acid O-α-glucoside, the pyrocatechol O-α-glucoside, the 3-hydroxydaidzein O-α-glucoside and the maritimein (3',4',6,7-tetrahydroxy-6-O-glucosylaurone) O-α-glucoside.

In an additional particular embodiment of the present invention, the phenolic compound O-α-glucoside has the following formula:

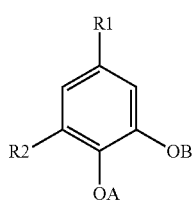

(II)

wherein

A and B, identical or different, are H or a α-glucosyl residue, with the proviso that at least one of A and B is a α-glucosyl residue;

R2 is H or OH; and

R1 is a $C_1$-$C_{10}$ hydrocarbon group which forms with the represented ring of formula (I) a fused aromatic ring (bi- or tri-cyclic) together with the ortho carbon of R1. In particular, the phenolic compound O-α-glucoside can be selected from the group consisting of

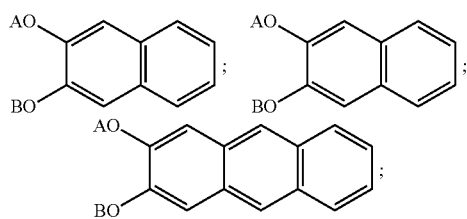

said fused ring can be optionally interrupted by at least one heteroatom and can be substituted by one or several substituents selected from the group consisting of: an ($C_1$-$C_3$)alkoxy, an ($C_2$-$C_3$)acyl, an ($C_1$-$C_3$)alcohol, a carboxylic group (—COOH), an ($C_2$-$C_3$)ester, an ($C_1$-$C_3$)amine, an amino group (—NH$_2$), an amide (—CONH$_2$), an ($C_1$-$C_3$) imine, a nitrile, a hydroxyl (—OH), an aldehyde group (—CHO), a halogen, a ($C_1$-$C_3$)halogenoalkyl, a thiol (—SH), a ($C_1$-$C_3$)thioalkyl, a ($C_1$-$C_3$)sulfone, a ($C_1$-$C_3$) sulfoxide and a combination thereof. In a particular preferred embodiment, the phenolic compound O-α-glucoside is

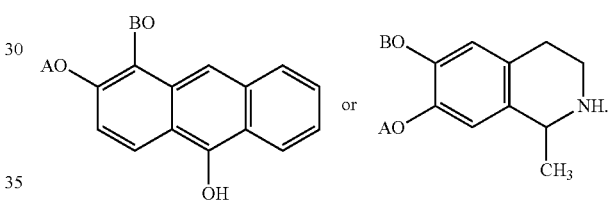

The O-α-glucosyl residue refers herein to a glucose monomer, dimer, trimer, tetramer, pentamer or more. Preferably, the O-α-glucosyl residue is a glucose monomer, dimer or trimer, namely glucosyl, diglucosyl or triglucosyl. Still preferably, the O-α-glucosyl residue is a glucose monomer. In a particular embodiment the O-α-glucosyl residue is attached to the phenolic compound by the carbon in position 1. In a preferred embodiment, OA is OH and OB is a O-α-glucosyl residue. In another preferred embodiment, OB is OH and OA is an O-α-glucosyl residue.

In a particular embodiment, R can be a monosaccharide. In another particular embodiment, R is a ($C_1$-$C_6$)alkyl or a ($C_1$-$C_3$)alkyl.

Such salts include pharmaceutically acceptable acid addition salts, pharmaceutically acceptable base addition salts, pharmaceutically acceptable metal salts and ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, perchloric and the like. Representative examples of suitable organic acids include formic, acetic, trichloroacetic, trifluoroacetic, propionic, benzoic, cinnamic, citric, fumaric and the like. Further examples of pharmaceutically acceptable inorganic or organic acid addition salts include the pharmaceutically acceptable salts listed in J. Pharm. Sci. 1977, 66, 2, and in Handbook of Pharmaceutical Salts: Properties, Selection, and Use edited by P. Heinrich Stahl and Camille G. Wermuth, 2002. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamineoline and the like.

In Situ Release of the Aglycones

Surprisingly, the inventors found that the phenolic compound O-α-glucosides of the present invention can be cleaved by α-glucosidases leading to in situ releasing of the phenolic compounds.

All the phenolic compound O-α-glucosides of the present invention have at least one O-α-glucoside bond. This bond can be specifically hydrolyzed by enzymes, such α-glucosidases (EC 3.2.1.20), to release the glucosyl residue and the aglycone part. When achieved in situ, this liberation has several advantages:

- it enables the release of the poorly soluble aglycones (which may be more active than the glycoside derivative) after their administration/injection/application under a soluble glycoside form, and/or
- the in situ release can be time-dependent (if achieved by enzymes expressed by microorganisms, the amount of releasing enzyme will be correlated to the number of microorganisms: the more dense the bacterial population will be, the more aglycones release will occur), and/or
- the in situ release can be controlled by an in situ administration/injection/application of an α-glucosidase or of a microorganism expressing such enzymatic activity.

These advantages are important in the formulation of phenolics in cosmetic or dermocosmetic preparations. In a preferred embodiment of the present invention, said phenolic compound O-α-glucosides can be activated in situ by enzyme(s) expressed by human-associated microorganisms, and more preferentially by human skin-associated microorganisms. Known and non-exhaustive examples of such human commensal or non-commensal microorganisms include *Streptococcus* species, *Staphylococcus* species, *Enterococcus* species, *Escherichia coli*, Bacilli, *Corynebacterium* species and *Propionibacterium* species. When applied on skin, the phenolic compound O-α-glucosides of the present invention are converted by skin associated microorganisms into the aglycone part and the glucosyl residue. Such bacteria can be found in human beings in the mouth, intestinal tract, genital tract and upper respiratory system.

In another preferred embodiment of the present invention, said phenolic compound O-α-glucosides can be activated in situ by an α-glucosidase (EC 3.2.1.20), such as the α-glucosidase from *Saccharomyces cerevisiae*.

So phenolic compound O-α-glucosides of the present invention have a pro-drug status as the active part of the molecule (the aglycones) can be released in situ.

Therefore, the present invention concerns a pharmaceutical or cosmetic composition comprising a phenolic compound O-α-glucoside of the present invention or a pharmaceutically acceptable salt thereof. The present invention also concerns a phenolic compound O-α-glucoside of the present invention or a pharmaceutically acceptable salt thereof as a medicament. The medicament can be therapeutic or prophylactic. Phenolic compound O-α-glucosides of the present invention have several activities among which are antiviral, antibacterial, immune-stimulating, antiallergic, antihypertensive, anti-ischemic, antiarrhythmic, antithrombotic, hypocholesterolemic, antilipoperoxidant, hepatoprotective, anti-inflammatory, anticarcinogenic antimutagenic, antineoplastic, anti-thrombotic and vasodilatory actions.

In a particular embodiment, the composition can further comprise an O-α-glucosidase (EC 3.2.1.20) or a microorganism expressing O-α-glucosidase activity. Preferably, the O-α-glucosidase is from *Saccharomyces cerevisiae*. In particular, the O-α-glucosidase (EC 3.2.1.20) or a microorganism expressing O-α-glucosidase activity is present in the composition in an inactivated form and the O-α-glucosidase is activated just at the moment of administration. For instance, the composition can be formulated in dried form, the absence of water leading to the inactivation of O-α-glucosidase; after water addition, the enzyme will become active and will then be able to hydrolyze the glucosidic bond. The enzyme and the phenolic compound O-α-glucosides can be put in two different liquid preparations that will be mixed just at the moment of administration. If the enzyme and the phenolic compound O-α-glucosides are put into the same solution, it is possible to use an enzyme reversible inhibitor that will be diluted after administration, thus allowing the enzyme to recover its ability to hydrolyze the phenolic compound O-α-glucosides. Phenolic compound O-α-glucosides of the present invention and the O-α-glucosidase or a microorganism expressing O-α-glucosidase activity can also be physically separated (e.g., microcapsule).

The present invention concerns the use of a phenolic compound O-α-glucoside of the present invention or a pharmaceutically acceptable salt thereof for preparing a pharmaceutical or cosmetic composition for treating or preventing a cancer, a cardiovascular disease, a bacterial infection, a UVB-induced erythema, an allergy, or an inflammatory or immune disorder. In particular, the cancer is a solid tumor, for example a breast or colon cancer. In particular, the allergy can be allergic rhinoconjunctivitis. Therefore, the present invention also concerns a method for treating or preventing a cancer, a cardiovascular disease, a bacterial infection, a UVB-induced erythema, an allergy, or an inflammatory or immune disorder comprising administering a phenolic compound O-α-glucoside of the present invention or a pharmaceutically acceptable salt thereof. In addition, the method can further comprise the step of administering sequentially or simultaneously an O-α-glucosidase (EC 3.2.1.20) or a microorganism expressing O-α-glucosidase activity. Preferably, the O-α-glucosidase (EC 3.2.1.20) or microorganism expressing O-α-glucosidase activity is administered by the same route.

In a particular embodiment, the present invention concerns the use of a phenolic compound O-α-glucoside of the present invention for preparing a pharmaceutical or cosmetic composition to be administered topically (i.e., on the skin), wherein enzymes issued from skin-associated microorganisms release the corresponding aglycone. In addition, the present invention concerns the use of a phenolic compound O-α-glucoside of the present invention for preparing a pharmaceutical or cosmetic composition to be administered orally, wherein enzymes issued from mouth- and intestinal tract-associated microorganisms release the corresponding aglycone. The present invention also concerns the use of a phenolic compound O-α-glucoside of the present invention for preparing a pharmaceutical or cosmetic composition to be administered rectally, wherein enzymes issued from intestinal tract-associated microorganisms release the corresponding aglycone. The present invention further concerns the use of a phenolic compound O-α-glucoside of the present invention for preparing a pharmaceutical or cosmetic composition to be administered nasally, wherein enzymes issued from upper respiratory system-associated microorganisms release the corresponding aglycone. The present invention further concerns the use of a phenolic compound O-α-glucoside of present invention for preparing a pharmaceutical or cosmetic composition to be administered vaginally, wherein enzymes issued from female genital tract-associated microorganisms release the corresponding aglycone.

The present invention also concerns a combination of a phenolic compound O-α-glucoside of the present invention or a pharmaceutically acceptable salt thereof with an O-α-glucosidase (EC 3.2.1.20) or a microorganism expressing O-α-glucosidase activity for simultaneous or sequential administration. When simultaneous administration is performed, the phenolic compound O-α-glucoside of the present invention or a pharmaceutically acceptable salt thereof and the O-α-glucosidase (EC 3.2.1.20) or a microorganism expressing O-α-glucosidase activity can be administered in the same or different compositions.

Such a composition can comprise pharmaceutically acceptable carriers, stabilizers or excipients.

Use of Phenolic Compounds as Key Intermediates for the Development of Other Derivatives Phenolic compound O-α-glucosides of the present invention can be directly used as active ingredients in cosmetics or as active substances alone or in combination with other products, including other active molecules with synergistic or complementary activities or with stabilizers or excipients. These phenolic compound derivatives can also be used as starting materials for additional chemical, physical or enzymatic modification(s) in order to produce second-generation derivatives. As the enzymatic reaction used in the present invention concerns specific hydroxyl positions on the catechol ring of the phenolic compound, the other hydroxyl groups can for example be used in a chemical reaction to create ester bonds, acyl bonds, sulphate or phosphate bonds. Such modifications can improve already existing properties of the phenolic compound O-α-glucosides of the present invention or provide new properties for specific applications (higher therapeutic efficiency, lower cytotoxicity, higher stability after release of the glycone part by microorganisms, etc.).

Formulation of Said Derivatives for Cosmetic or Therapeutic Applications

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intrasynovial, intrasternal, intrathecal, intrahepatic, intralesional and intracranial injection or infusion techniques. Preferably, the compositions of the present invention are administered orally, by inhalation spray, topically, rectally, nasally, buccally or vaginally. In a preferred embodiment, the pharmaceutical or cosmetic composition is administered topically.

New types of cosmetic products are constantly being developed and new raw materials are adding to the cosmetic chemist's selection of personal care ingredients. The phenolic compound O-α-glucosides described in the present invention can easily be incorporated in a large panel of cosmetic products. Such preparations are well known in the art: they can be creams, sticks, shampoos, shower gels, lotions, soaps, emulsions, or gels. These formulations can include other ingredients, such as but not limited to deionized water, magnesium, aluminium silicate, xanthan gum, nylon-12, sodium PCA, propylene glycol, red iron oxides, talc, yellow iron oxides, black iron oxides, titanium dioxide, glyceryl stearate, stearic acid, DEA-cetyl phosphate, methylparaben, butylparaben, ethylparaben, propylparaben, isotearyl neopentanoate, isopropyl palmitate, ethylene/propylene/styrene copolymer, butylene/ethylene/styrene copolymer, isopropyl palmitate, phenoxyethanol tocopheryl acetate, glycerin, triethanolamine, stearic acid, propylene glycol stearate, mineral oil, buthylene/ethylene/styrene copolymer, diazolidinyl urea, hydrogenated polyisobutene, octyl palmitate, tridecyl neopentanoate, isostearyl isostearate, isopropylparaben, isobutyparaben, octyldodecyl neopentanoate, tocopheryl acetate, fragrance, octyl methoxycinnamate, benzophenone, octyl salicylate, isopropyl isostearate, propylene glycol isoceteth-3 acetate or any combinations thereof.

For their use in therapeutic applications, phenolic compound O-α-glucosides of the present invention can be incorporated in different galenic preparations such as pills, tablets, syrups, creams, lotions, or gels, using for example packing, standardisation, blending/homogenisation, sterile and nonsterile micronization, granulation/compacting, sieving or any combination thereof. Preparations of said phenolic compound O-α-glucosides can include some excipients of the following non-exhaustive list: talc, lactose, magnesium stearate, glycerol monostearate, colloidal silicon dioxide, precipitated silicon dioxide, crosslinked polyvinyl pyrrolidone, dibasic calcium phosphate dihydrate, micro crystalline cellulose, corn starch, povidone, sodium carboxy-methyl cellulose, polysorbate 80, lactic acid, carbomer, cethyl alcohol, isopropyl myristate, isopropyl palmitate, glucose, dextrose, triethanolamine, glycerine, fructose, sucrose, polymers and nanostructures.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycol.

The compositions of this invention may also be administered topically, especially when the target of treatment includes areas or organs readily accessible by topical application, including diseases of the eye, the skin or the lower intestinal tract. Suitable topical formulations are readily prepared for each of these areas or organs.

For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compounds, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the compositions may be formulated as micronized suspensions in isotonic, pH-adjusted sterile saline or, preferably, as solutions in isotonic, pH-adjusted sterile saline, either with or without a preservative such as benzylalkonium chloride. Alternatively, for ophthalmic uses, the compositions may be formulated in an ointment such as petrolatum.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives, are useful in the preparation of injectables, as are natural pharmaceutically-acceptable oils such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid or other dosage forms may also be used for the purposes of formulation.

Advantages of the Present Invention

The advantages of the method of the present invention over pre-existing methods appear clearly from the previous descriptions and embodiments. A non-exhaustive list of other advantages of the present invention are described below.

The present invention describes new original phenolic compound O-α-glucosides of
  protocatechuic acid and its ester derivatives,
  caffeic acid and its ester derivatives, especially rosmarinic acid, chlorogenic acid and caffeic acid phenethyl ester and hydrocaffeic acid or 3,4-dihydroxyhydrocinnamic acid, 3,4-dihydroxyphenylacetic acid and 3,4-dihydroxyphenylglycol,
  esculetin,
  taxifolin,
  fustin,
  eriodictyol,
  fisetin, and
  rhamnetin.

Preferably, the new original phenolic compound O-α-glucosides of the present invention are selected from the group consisting of the epicatechin gallate O-α-glucoside, the eriodictyol O-α-glucoside, the esculetin O-α-glucoside, the fisetin O-α-glucoside, the fustin O-α-glucoside, the homoprotocatechuic acid O-α-glucoside, the protocatechuic acid O-α-glucoside, the protocatechuic acid ethyl ester O-α-glucoside, the hydroxytyrosol O-α-glucoside, the maclurine O-α-glucoside, the nordihydroguaiaretic acid O-α-glucoside, the oleuropein O-α-glucoside, the pyrocatechol O-α-glucoside, the rhamnetin O-α-glucoside, the rosmarinic acid O-α-glucoside, the taxifolin O-α-glucoside, the 3-hydroxydaidzein O-α-glucoside, the 3,4-dihydroxybenzophenone O-α-glucoside, the caffeic acid O-α-glucoside, the dihydrocaffeic acid O-α-glucoside, the caffeic acid phenethyl ester O-α-glucoside, the cirsiliol O-α-glucoside, the chlorogenic acid O-α-glucoside, the anthrarobin O-α-glucoside, the epigallocatechin O-α-glucoside, the dihydrorobinetin O-α-glucoside, the gallocatechin O-α-glucoside, the gallic acid O-α-glucoside, the propyl gallate O-α-glucoside and the robinetin O-α-glucoside.

These phenolic compound O-α-glucosides, of high interest in the fields of cosmetics and therapy, show improved water solubility. Indeed, an increase by at least 20, 30 or 50-fold of the solubility has been observed in comparison with the corresponding aglycone in the same physiological conditions.

These phenolic compound O-α-glucosides have increased bioavailability. These phenolic compound O-α-glucosides can be activated in situ through their hydrolysis into the initial phenolic structure by human commensal microorganisms, giving them a prodrug status of high interest for both cosmetic and therapy applications. They can also be activated with an α-glucosidase, such as the α-glucosidase produced by the yeast *Saccharomyces cerevisiae*.

These new phenolic compound O-α-glucosides are obtained through a proven, reliable, low-cost, "green chemistry" enzymatic process that ensures the high quality of these products (due to the specificity and selectivity of the enzyme used).

EXAMPLES

Any other embodiments and advantages of the present invention will appear from the following examples that are illustrative of embodiments of the invention and are not meant to limit the scope of the invention as encompassed by the claims.

Example 1

Synthesis of Glucosylated Taxifolin; Solubility in Water of Highly Purified Glucosylated Taxifolin and Stability of the Glucosylated Derivative Molecule at Temperatures Ranging from 4° C. to 45° C.

The conditions that were carried out for the synthesis of glucosylated Taxifolin are as follows (amounts for 1 liter of reaction medium):

| Ingredient | Origin | Amount | Concentration |
|---|---|---|---|
| Solution of Taxifolin at 90 g/L in pure DMSO | Taxifolin: SIGMA T 4512 | 100 ml | Taxifolin: 9 g/L |
| DMSO | Riedel de Haën 60153 | 250 ml | Total DMSO: 350 ml/L |
| Sodium acetate buffer 500 mM pH 5.2 | Acetic acid: Prolabo 20104.298 Sodium hydroxide: Riedel de Haën 6203 | 40 ml | Sodium acetate: 20 mM |
| Sucrose at 500 g/L (1.462M) | Prolabo 27478.296 | 300 ml | 150 g/L 0.439M |
| Water | Deionized | Qsp 1.00 L | # |
| Calcium chloride, dihydrate | Merck 1.02382.0500 (can also be introduced in the reaction medium in the form of a solution at 2 g/L; the dose is then 5 ml/L) | 10 mg | 10 mg/L |
| Dextransucrase preparation (18 U/ml) | Purified from *L. mesenteroides* NRRL B-512F culture broth | 170 ml | 3.1 U/ml |

The reaction medium without the enzyme was first obtained by mixing the various solutions in the order reported in the table. The mixture was incubated at 30° C. during a period of time sufficient to attain the desired temperature of 30° C. (plus or minus 0.2° C.). Then the reaction was started by introducing the enzyme preparation. The reaction medium may be moderately agitated.

The enzyme preparation has been obtained as follows: the culture broth of *Leuconostoc mesenteroides* NRRL B512-F titrating an enzyme activity ranging from 4 to 6 U/ml is centrifuged in order to completely separate the microbial cells from the liquid containing the enzyme. The centrifugation supernatant was then concentrated 4 to 10 times by tangential ultrafiltration (molecular weight cut off of 100 kDa). The retentate was then diluted 4 times with 20 mM acetate buffer pH 5.2 containing calcium chloride dihydrate at 10 mg/L and then concentrated 4 times in order to extensively remove the residual low-molecular-weight components of the cell culture medium containing the enzyme. The purified enzyme preparation has then been stored in a frozen form (−20° C.) or freeze-dried up to several months without loss of activity. As a general procedure, the activity of the enzyme preparation is adjusted by intensifying the concentration of the retentate in order that the volume of the enzyme preparation will not be higher than 20% of the final volume of the synthesis reaction medium.

The reaction medium was incubated at 30° C. (plus or minus 0.2° C.) during 22 hours. An aliquot of the reaction medium was taken off from the reaction medium and diluted 50 times with a solution containing methanol and water in the proportions of 40/60. The methanolic solution was then analyzed by HPLC.

The analysis conditions were those as previously described except that the profile of the methanol concentration was as follows (Method 2):
 solvent A: deionized water containing 1% v/v acetic acid
 solvent B: HPLC grade methanol containing 1% v/v acetic acid
 0 to 10 minutes: 60% A; 40% B; 1 ml/minute
 10 to 12 minutes: 60% to 20% A (linear); 40% to 80% B (linear); 1 ml/minute
 12 to 14 minutes: 20% A; 80% B; 1 ml/minute
 14 to 16 minutes: 20% to 60% A (linear); 80% to 40% B (linear); 1 ml/minute
 16 to 25 minutes: 60% A; 40% B; 1 ml/minute
 25 minutes: next injection.

Figure 7:
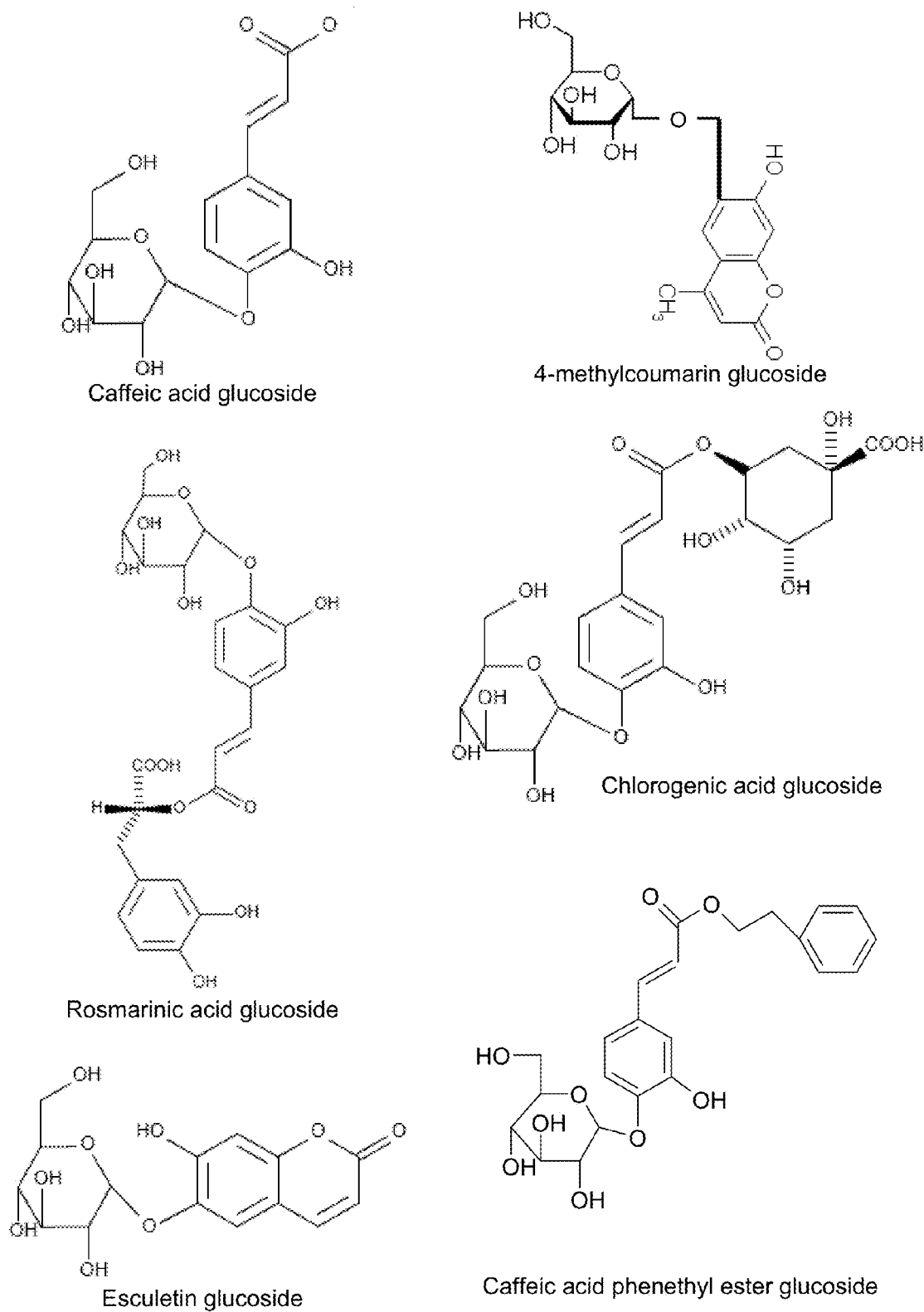
FIG. 7—Glucoside of caffeic acid derivatives.
Figure 7:
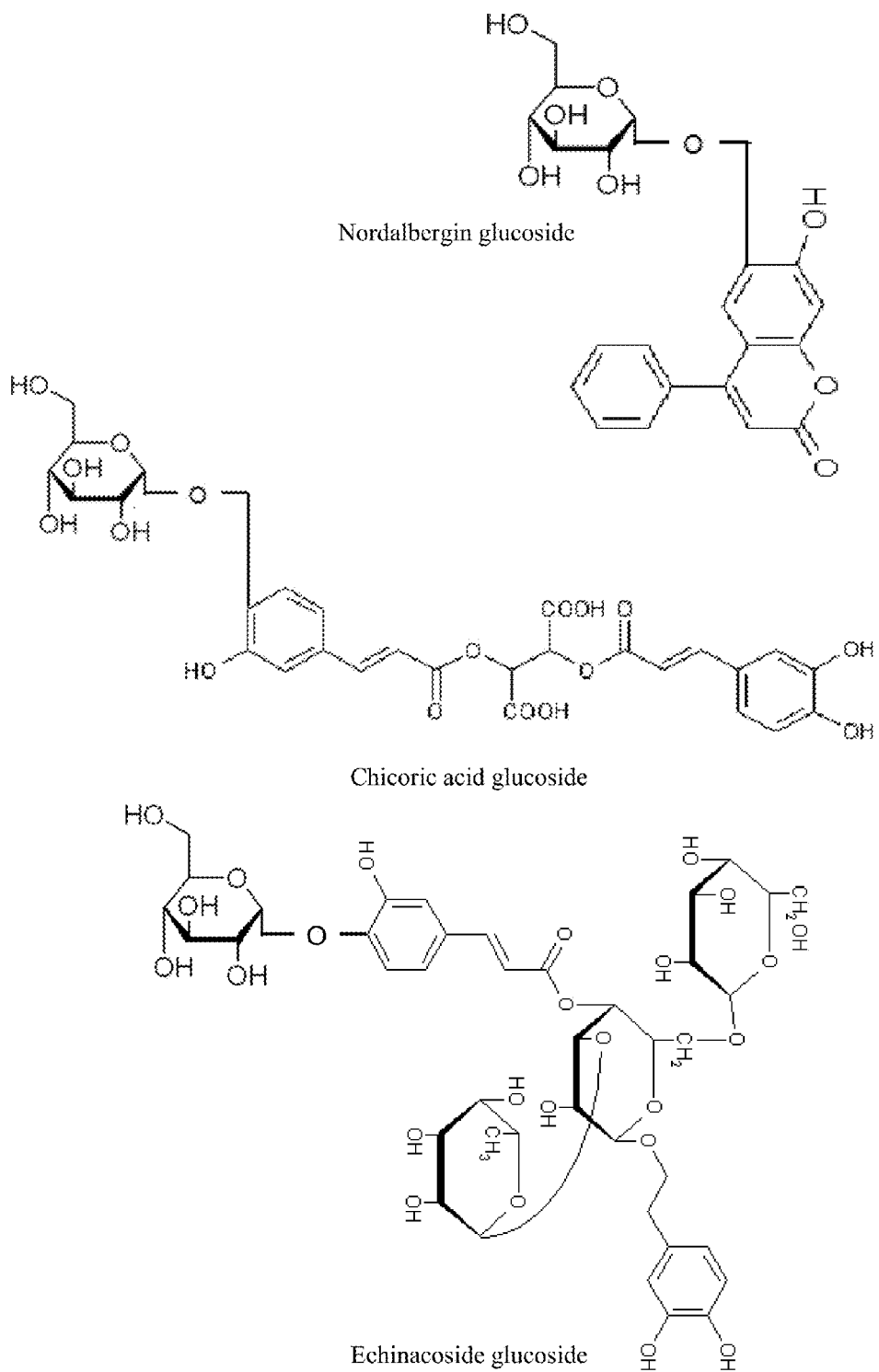
Figure 7:
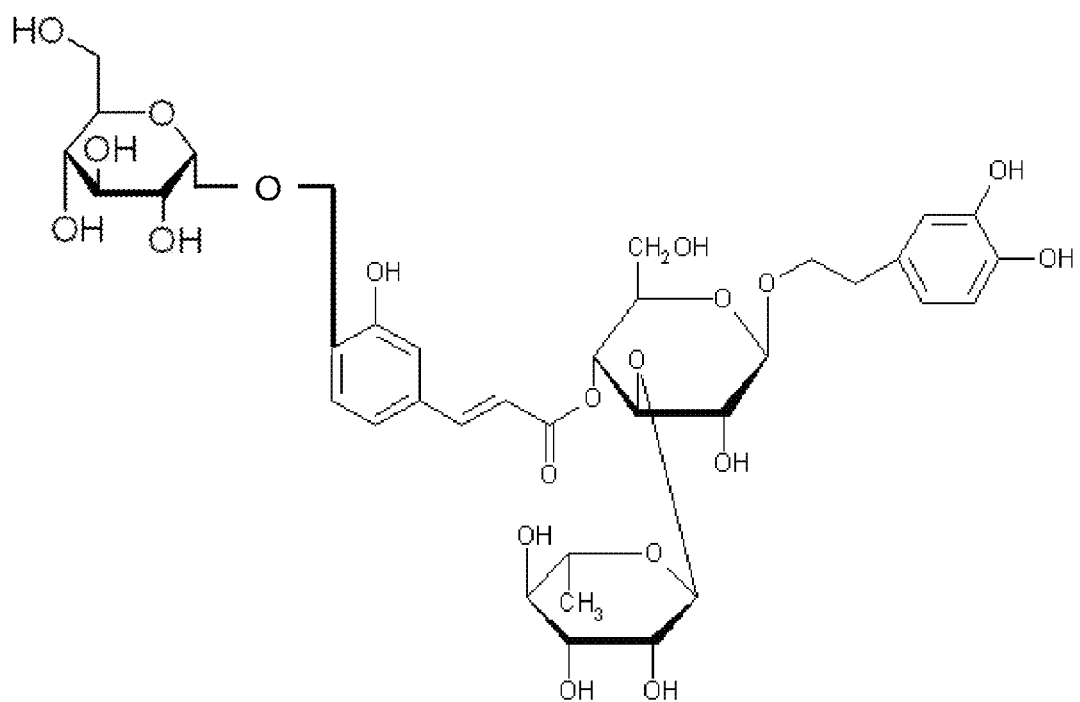

FIG. 7 shows the HPLC chromatogram of the reaction medium containing Taxifolin as glucoside acceptor (289 nm) at just the beginning of the incubation. The major pic at 8.15 minutes corresponds to Taxifolin.

Figure 8:
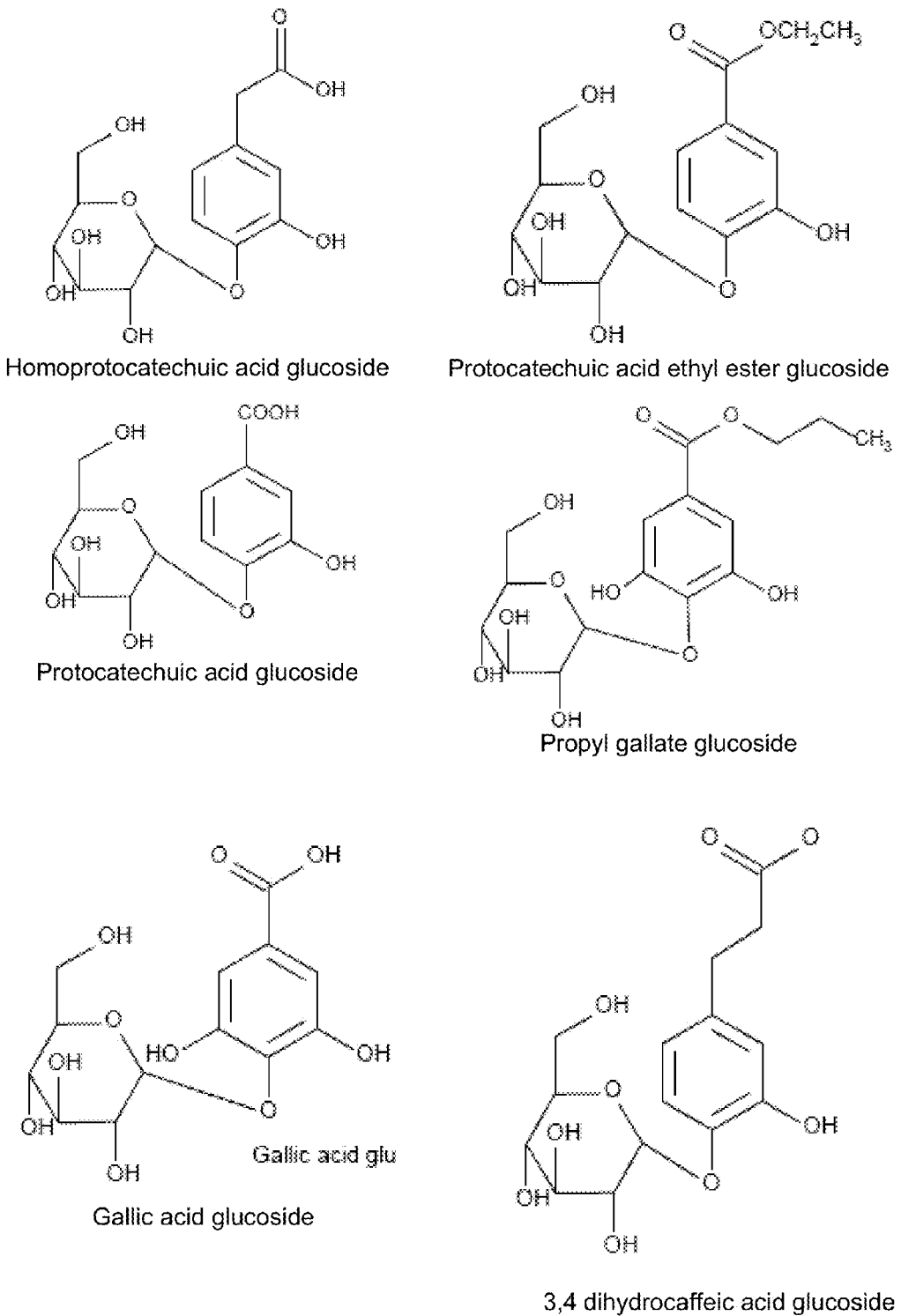
FIG. 8—Glucoside of 3,4 dihydroxybenzoic acid and other phenolic acids.
Figure 8:
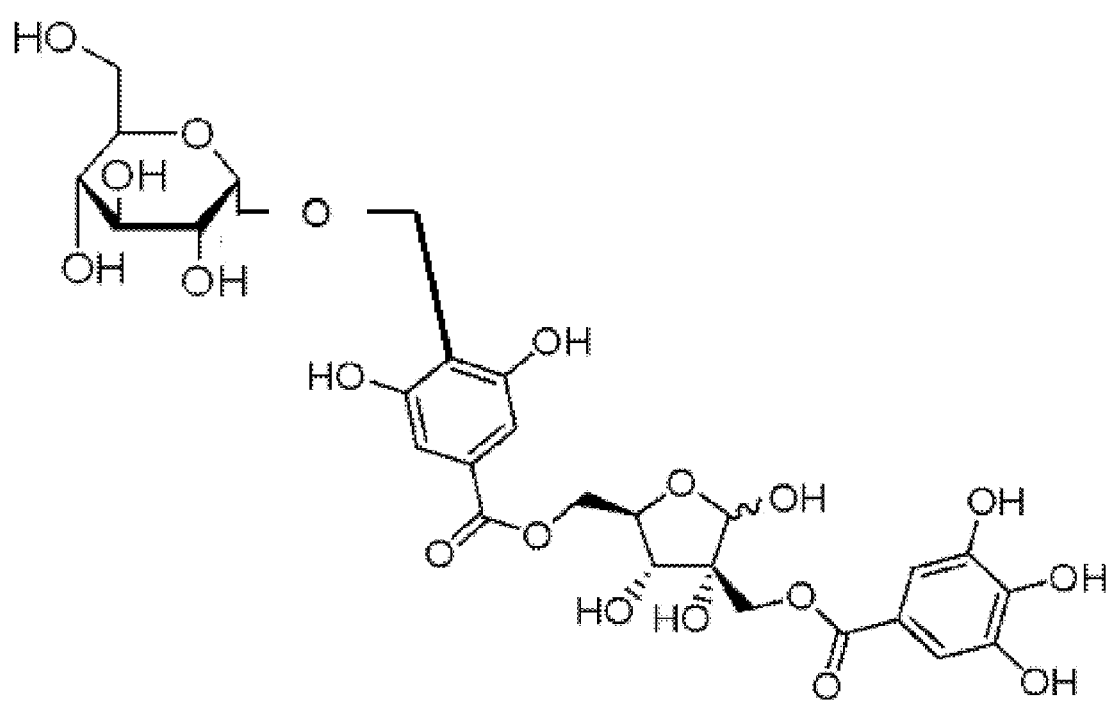

FIG. 8 shows the HPLC chromatogram of the reaction medium containing Taxifolin as glucoside acceptor (289 nm) after 22 hours of incubation. A pic with a retention time of 6.15 minutes is observed.

Figure 9:
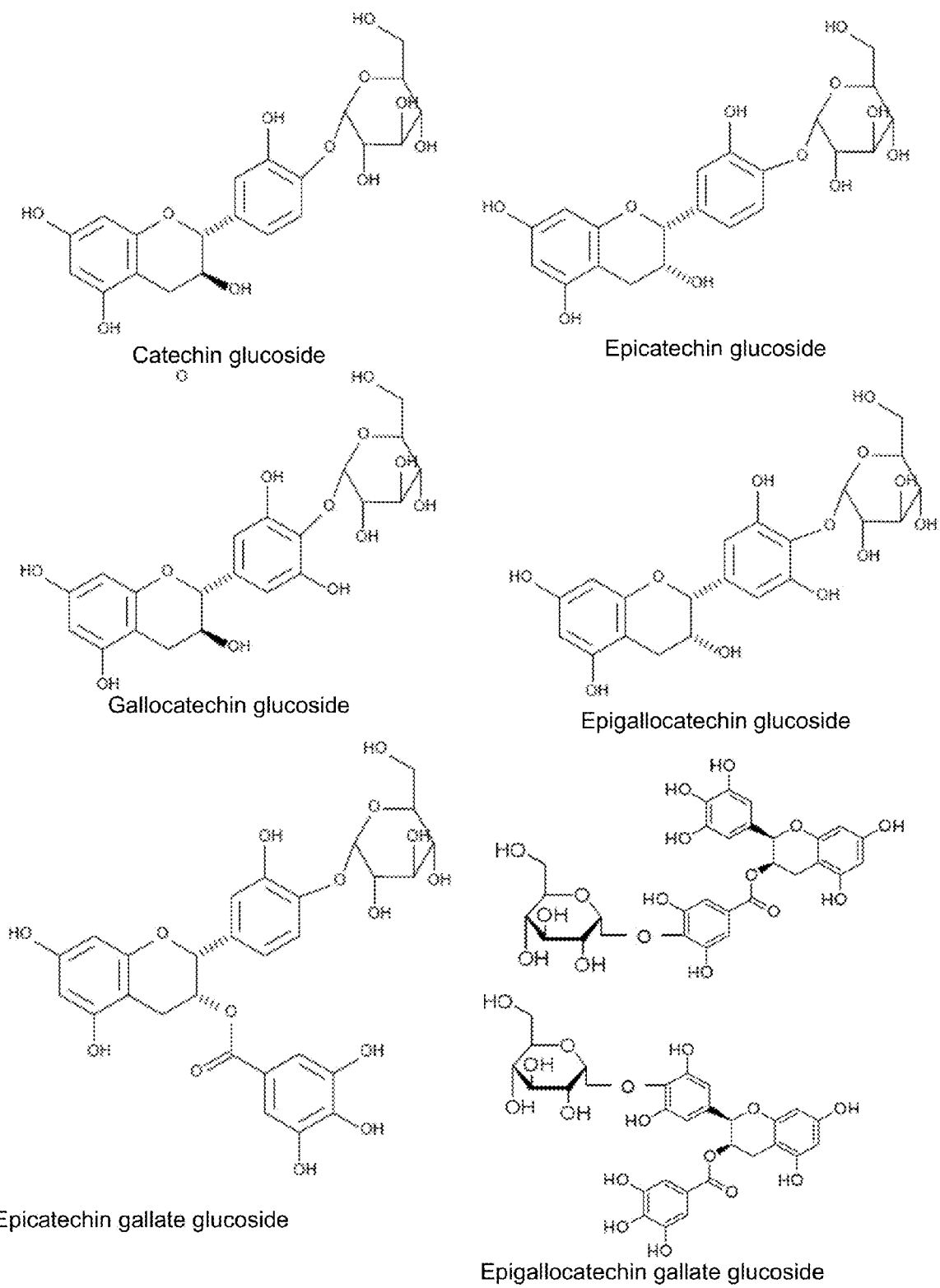
FIG. 9—Glucoside of flavanol.
Figure 10:
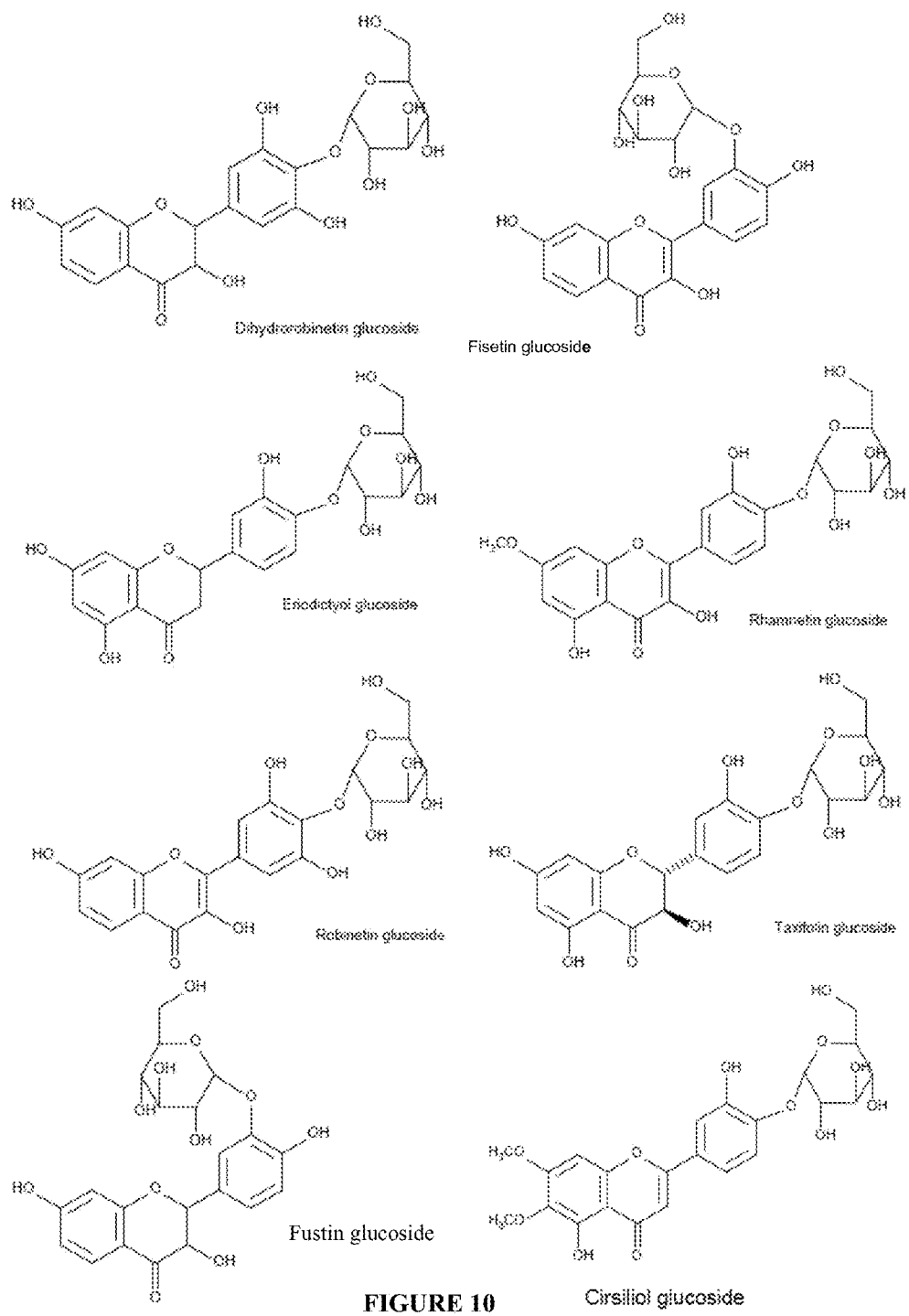
FIG. 10—Glucoside of flavonol, isoflavone, flavone and dihydroflavonol.
Figure 10:
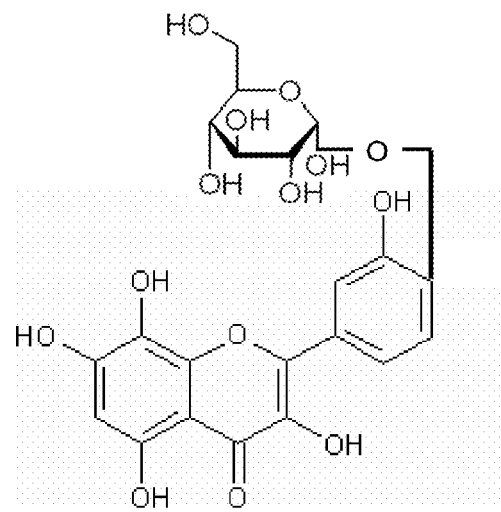
Figure 10:
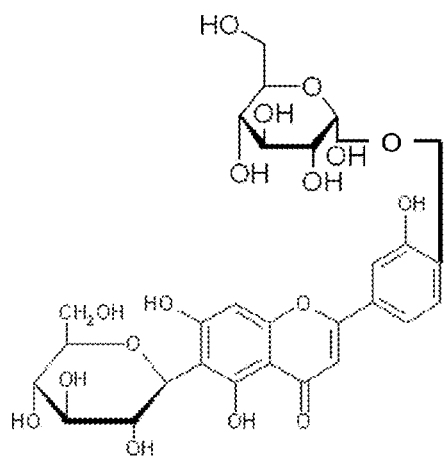
Figure 10:
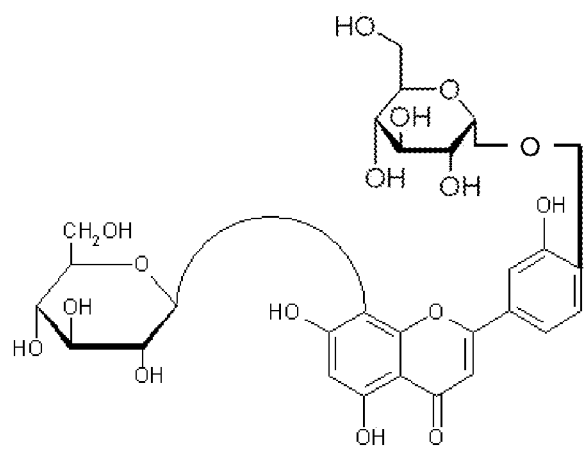

FIG. 9 shows the mass spectrum and FIG. 10 the UV spectrum of the pic eluted at around 8.15 minutes: the substance is Taxifolin (m/z [M-H]: 302.96 and m/z [M-H—H$_2$O]: 284.96) which molecular weight is 304.

Figure 11:
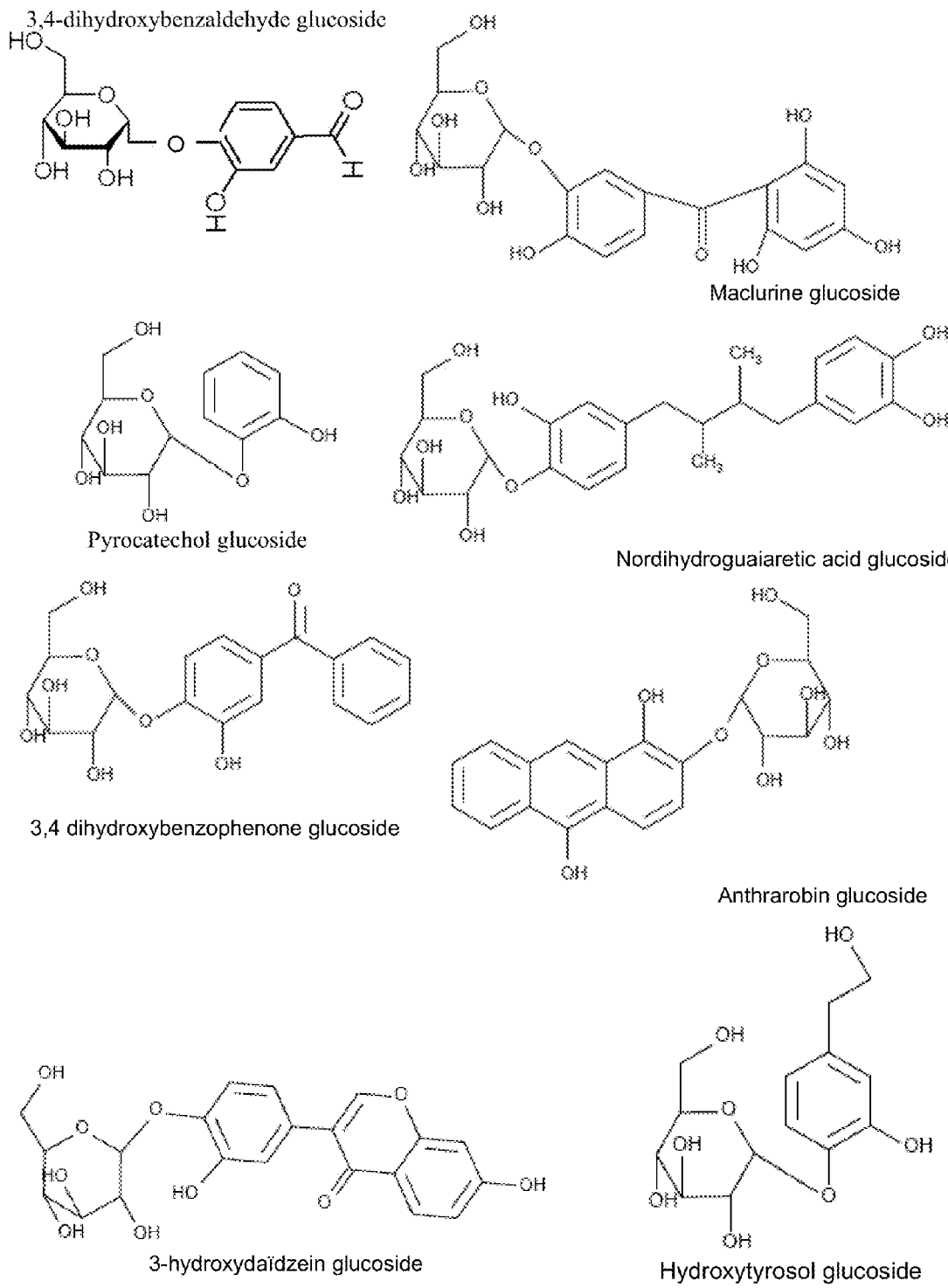
FIG. 11—Glucoside of neutral polyphenol.
Figure 11:
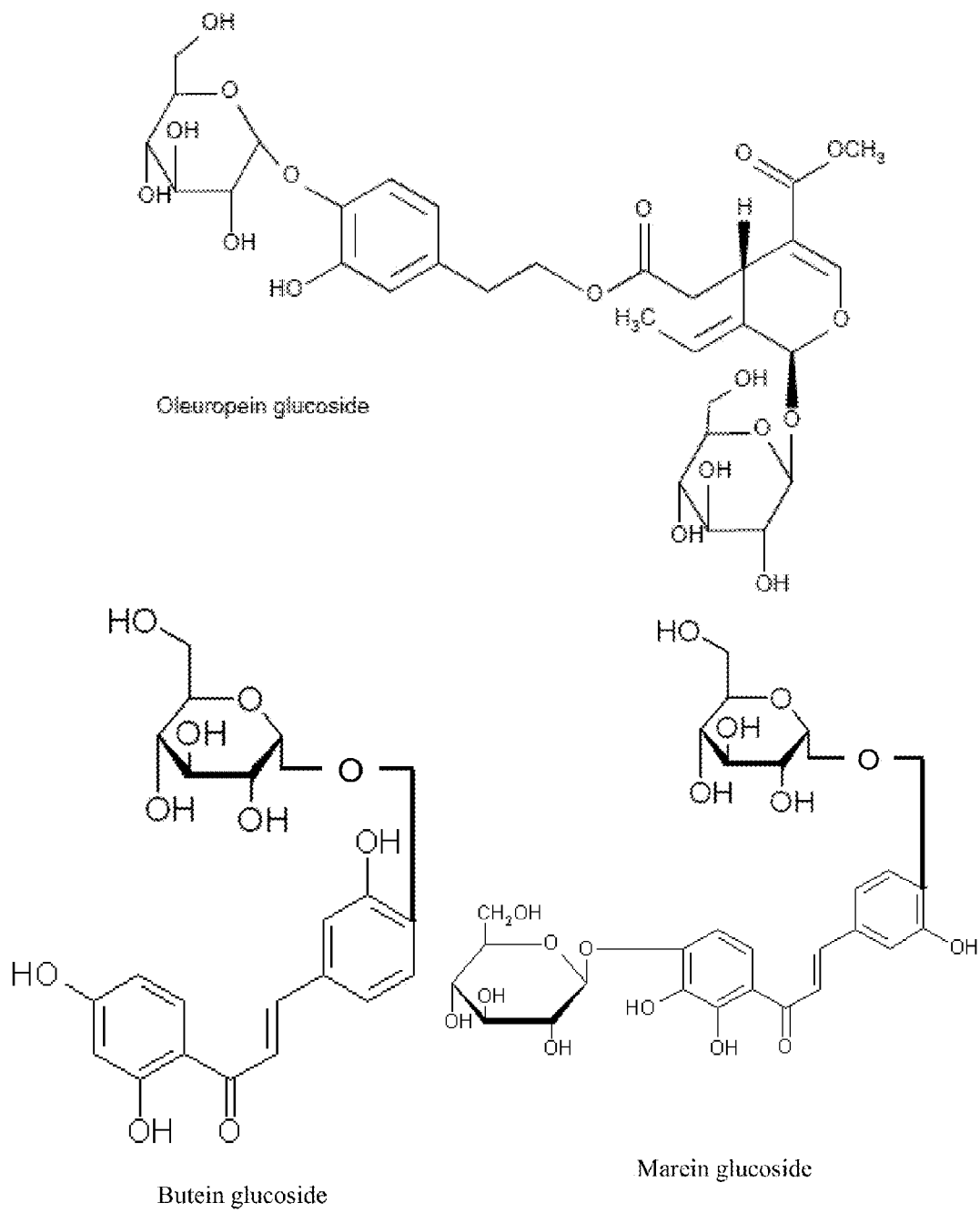
Figure 11:
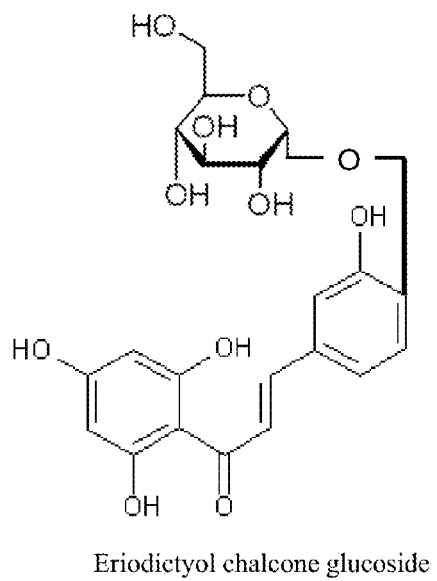
Figure 11:
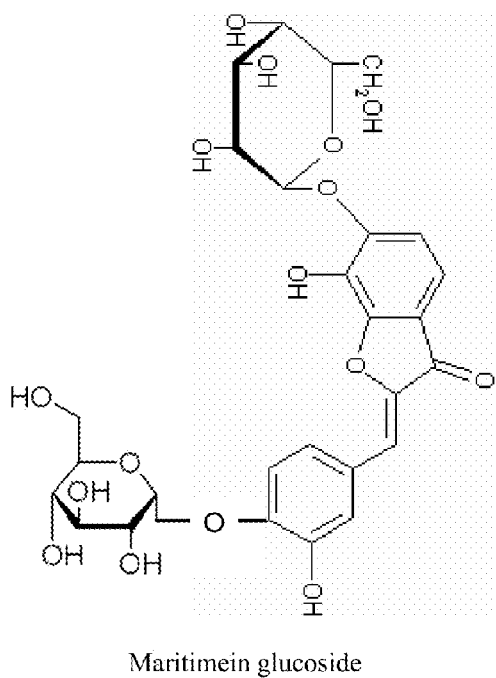
Figure 11:
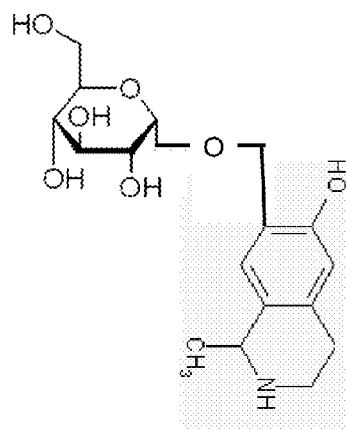
Figure 11:
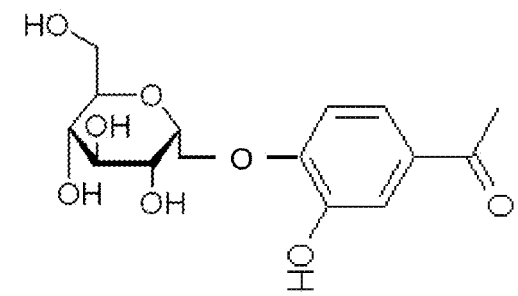
Figure 12:
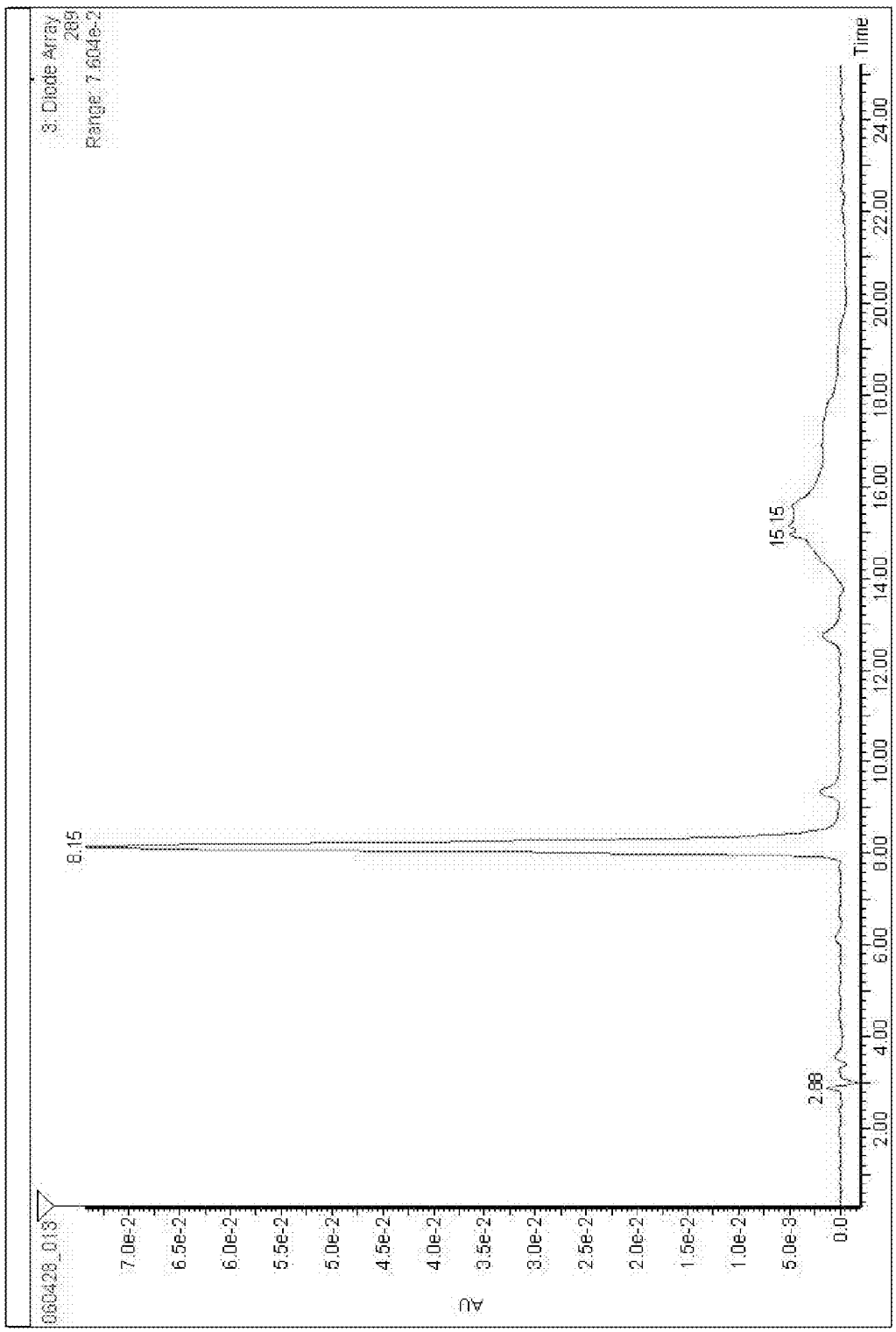
FIG. 12—HPLC chromatogram of the reaction medium containing Taxifolin as glucoside acceptor (289 nm). Incubation duration: 0.

FIG. 11 shows the mass spectrum and FIG. 12 the UV spectrum of the pic eluted at around 6.15 minutes: the corresponding substance is Taxifolin glucoside (m/z [M-H]: 464.98) since its molecular weight is 466.

The substances eluted at 9.33 and 12.75 minutes are polyphenolic substances found in the Taxifolin preparation.

Figure 13:
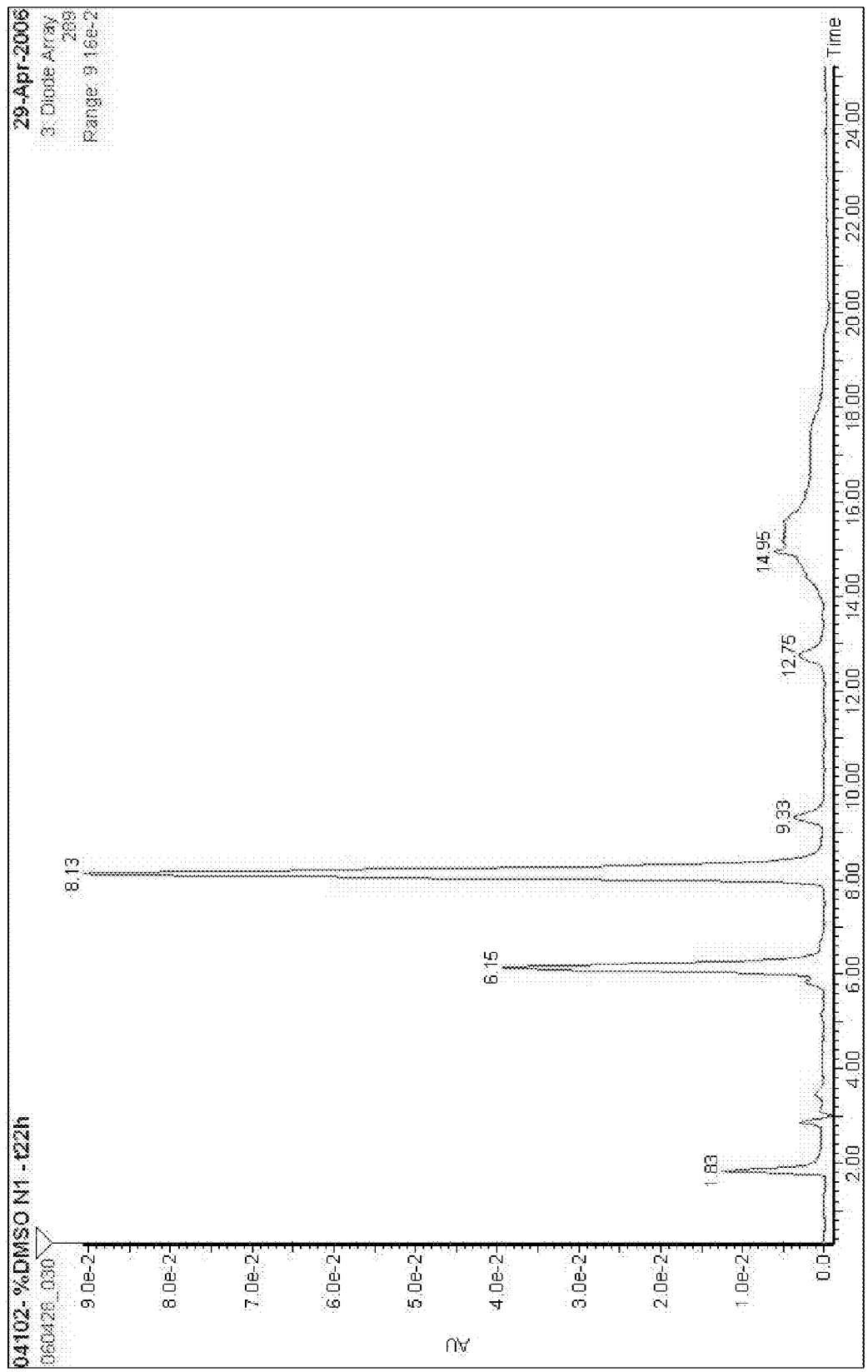
FIG. 13—HPLC chromatogram of the reaction medium containing Taxifolin as glucoside acceptor (289 nm). Incubation duration: 22 hours.

FIG. 13 shows a the HPLC chromatogram of an aqueous solution containing Taxifolin and Taxifolin glucoside after carrying out purification to remove the enzyme, dextran, fructose and DMSO and a fraction of residual Taxifolin. The eluting conditions are those previously described in which the initial content of methanol is 10% (method 1). Taxifolin is eluted at 24.01 minutes and Taxifolin glucoside at 22.33 minutes.

Taxifolin glucoside has been purified extensively to reduce as much as possible the Taxifolin concentration. A solution was finally obtained by titrating more than 93 mM of Taxifolin glucoside with a Taxifolin residual concentration of less than 2 mM (FIG. 14; Taxifolin eluted at 8.95 minutes and Taxifolin glucoside eluted at 6.55 minutes).

Concentrations of Taxifolin glucoside were determined as follows: after having established the relationship between the molar concentration of Taxifolin and the pic areas with a precisely characterized Taxifolin preparation (SIGMA), concentrations of Taxifolin glucoside were determined by applying the relationship between area and concentration to Taxifolin glucoside, since Taxifolin and Taxifolin glucoside have the same UV spectra. Then, concentrations in g/L were obtained by multiplying the molar concentration by the value of the Taxifolin glucoside molecular weight (466). Whereas the Taxifolin solubility in water at 25° C. is measured at 1.19 g/L (3.91 mM), the solubility of Taxifolin glucoside in water at 25° C. is higher than 43.5 g/L (93.2 mM).

It is thus possible, according to the described method, to synthesize a new substance, Taxifolin glucoside, with a molecular weight of 466 and a solubility in water at around 25° C. higher than 93 mM, corresponding to an increase in water solubility regarding the Taxifolin residue higher than 23. Taxifolin glucoside can be purified according to the techniques previously mentioned (resin adsorption, elution, concentration, liquid extraction, solvent removal and concentration and eventually drying).

The Taxifolin glucoside solution can be stored during a long period of time without loss of the glucosidic bond and with a quite satisfactory resistance to oxidation.

Accelerated shelf-life studies were performed using temperature chambers at 4° C., 22° C., 37° C. and 45° C. for 4 months. The Taxifolin glucoside content was frequently measured and color and odor were roughly controlled. The Taxifolin glucoside content was determined by HPLC as previously described (500 fold dilution of an aliquot of the solution and analysis using method 2; detection: 210-400 nm).

The following table describes the observed quantity of Taxifolin glucoside versus the storage time at different storage temperatures.

| | Measured quantity of taxifolin glucoside (in % of the initial quantity) | | | |
|---|---|---|---|---|
| Days | Stored at +4° C. | Stored at +22° C. | Stored at +37° C. | Stored at +45° C. |
| 0 | 100 | 100 | 100 | 100 |
| 9 | 100 | 100 | 100 | 100 |
| 23 | 100 | 100 | 100 | 91 |
| 37 | 100 | 100 | 100 | 94 |
| 63 | 100 | 95 | 96 | 79 |
| 118 | 100 | 100 | 91 | 73 |

No colour or odour changes have been observed whatever the temperature of storage.

Therefore, the glucoside bond between Taxifolin and the glucose moiety is stable in the above-tested conditions. At 37° C. and 45° C., a slight degradation of the Taxifolin glucoside has been observed, probably due to oxidation; indeed, no Taxifolin concentration increase that would indicate a hydrolysis of the glucosidic bond was observed in the corresponding solutions. In the above mentioned conditions, the half-life of Taxifolin glucoside is estimated at 1.6 year at 37° C. and 0.67 year at 45° C.

This example demonstrates that Taxifolin glucoside has a high chemical stability even in harsh storage conditions.

Example 2

Influence of the DMSO Concentration on the Efficiency of the Synthesis of Taxifolin Glucoside Taxifolin glucoside enzymatic synthesis was carried out as described in Example 1 with the following exceptions:
enzyme concentration was 1 U/ml, and
DMSO concentration was 35%, 25%, 15% or 5%.

After 22 hours of incubation, relative Taxifolin glucoside concentrations in the four reaction media are reported in the following table.

| | DMSO, % | | | |
|---|---|---|---|---|
| | 35 | 25 | 15 | 5 |
| Taxifolin glucoside (relative concentration), % | 100 | 133 | 161 | 17 |

The optimal DMSO concentration for the synthesis of Taxifolin glucoside appears to be at a value significantly lower than 30% and close to 15%.

Example 3

Activation of Taxifolin Glucoside by Human Skin Microflora

Cutaneous flora were separately collected from 5 donors. The forearms and forehead of each donor were scraped with a cotton-wool swab saturated with NaCl solution (v=5 mL, 8 g/l). After each scraping, the swab was divided into the remaining NaCl solution and squeezed to deliver the sampled material. After two cycles of scraping/squeezing on both forearms and three on the forehead, the obtained trouble preparation was filtered (40 µm) to eliminate squama and finally centrifuged (4° C., 5000 g, 15 min). The microbial pellets were resuspended in a NaCl solution (v=1 mL, 8 g/l) and characterized by OD at 600 nm.

The five microbial samples were mixed to form the final microbial suspension used for the test. Microbial cells were cultivated using the Hickey-Tresner culture medium (yeast extract at 1.0 g/L, meat extract at 1.0 g/L, casein peptone at 2.0 g/L, starch at 10.0 g/L, cobalt chloride hexahydrate at 20 mg/l; pH=6). Microbial growth was carried out in 100 ml Erlenmeyer flasks at 37° C. under continuous agitation (100 rpm). The sterile culture broth (20 ml) was inoculated with 0.1 mL of suspension. Microbial growth was controlled by measuring the OD at 600 nm.

Figure 14:
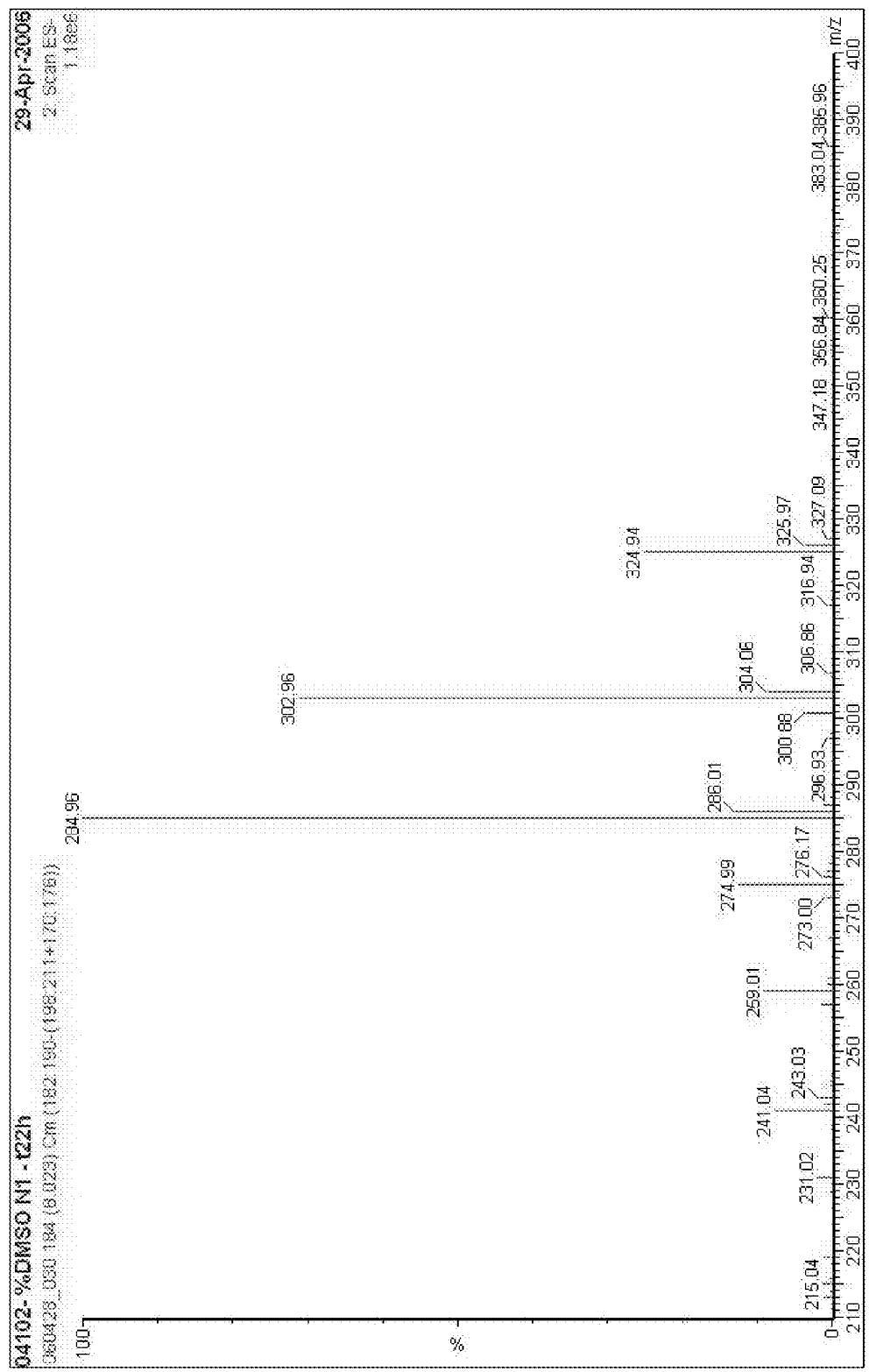
FIG. 14—Mass spectrum of the substance eluted at around 8.13 minutes. Incubation duration: 22 hours.

Taxifolin glucoside was obtained as described in example 1 (highly purified preparation corresponding to the HPLC chromatogram reported in FIG. 14). Taxifolin glucoside was added or not at day 0 (V=0.5 mL of 0.20 µm sterilized solution). Control was made by growing the final microbial suspension without Taxifolin glucoside.

After centrifugation of an aliquot of cell culture media, the supernatant was diluted 4-fold with a solution containing methanol and water in the proportions of 40/60. Taxifolin glucoside and taxifolin concentrations in the supernatants were determined by HPLC (method 2).

Figure 15:
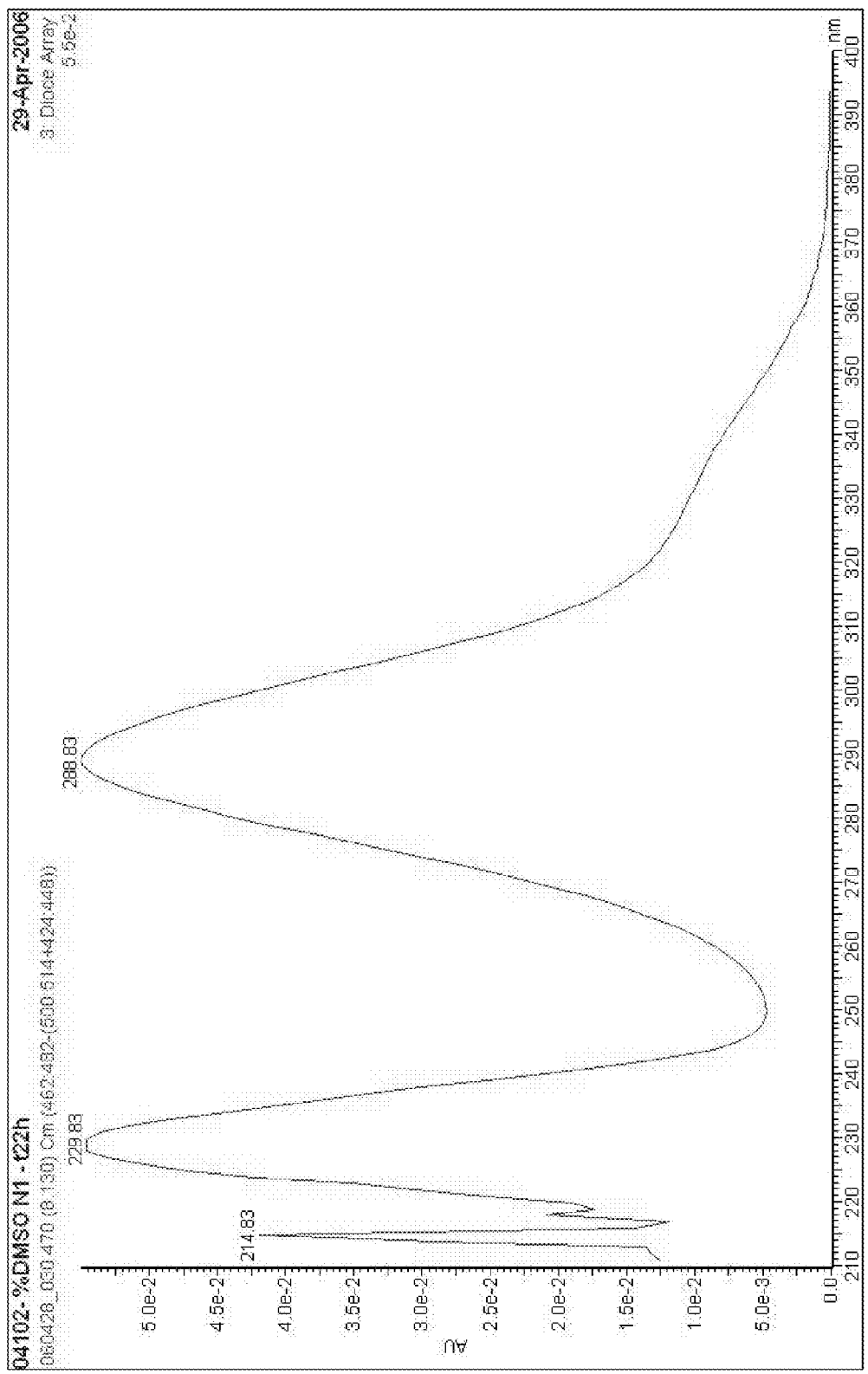
FIG. 15—UV spectrum of the substance eluted at around 8.13 minutes. Incubation duration: 22 hours.

FIG. 15 shows the apparent bacterial growth during a week in the Hickey-Tresner culture medium. From day 3 to day 7, the apparent biomass production is higher in the presence of Taxifolin glucoside than in its absence. This might be explained by a higher concentration of carbon and energy source due to the liberation of the glucose from the taxifolin glucoside under the bacterial hydrolysis.

Figure 16:
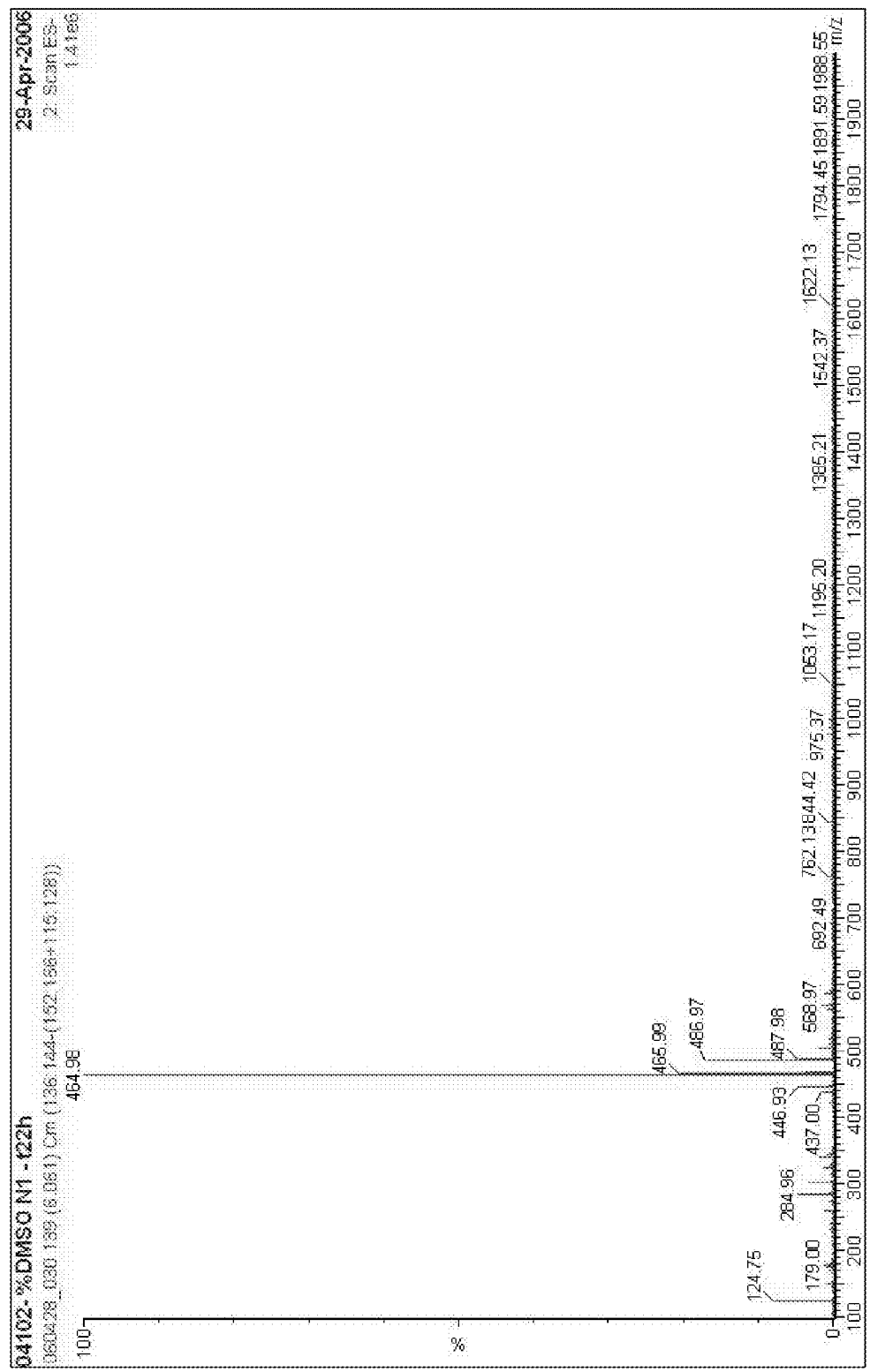
FIG. 16—Mass spectrum of the substance eluted at around 6.15 minutes. Incubation duration: 22 hours.

In FIG. 16, the hydrolysis of Taxifolin glucoside cannot be detected during the first three days. After three days of incubation, probably when the carbon and energy source become limiting, the concentration of Taxifolin glucoside diminishes in a significant manner and the aglycone flavonoid, Taxifolin, appears concomitantly. The nutritional stress undergone by the bacterial community originating from the human cutaneous flora might stimulate the liberation of the glucosyl residue through the action of the secreted enzymes.

This example demonstrates that human cutaneous flora recognize and are able to hydrolyze the flavonoid glucosidic bond with a high output, offering a new pathway for the delivery of active ingredients.

Example 4

Activation of Taxifolin Glucoside by an α-Glucosidase Preparation

Taxifolin glucoside was incubated in the presence of an α-glucosidase enzyme in the following conditions:

Taxifolin glucoside obtained as described in example 1 (highly purified preparation corresponding to the HPLC chromatogram reported in FIG. 14): 0.25 ml;

α-glucosidase (from *Saccharomyces cerevisiae*; FLUKA 70797; lot 0641337/1; activity: 5.8 U/mg): 50.1 mg in 5 ml of potassium phosphate buffer 0.1 M, pH 7.3; no enzyme in the control reaction medium;

Temperature: 30° C.;

Moderate agitation.

The reaction media were analysed by HPLC (method 2) after a 2-fold dilution of an aliquot with methanol.

After 18 hours of incubation, the Taxifolin glucoside molecule remained unchanged in the medium which did not contain the α-glucosidase enzyme whereas the Taxifolin glucoside molecule was totally converted into Taxifolin in the presence of the α-glucosidase enzyme.

These results show that an isolated enzyme specific for the hydrolysis of α-glucosidic bonds is able to hydrolyse the Taxifolin glucoside molecule; this indicates that the Taxifolin glucoside molecule contains Taxifolin and glucose with glucose being linked to a hydroxyl group of Taxifolin through an α-glucosidic bond. For this reason, the synthesized new glucoside derivatives are claimed O-α-D-glucoside derivatives.

Example 5

Enzymatic Synthesis of O-α-D-Glycosides of Pyrocatechol, Protocatechuic Acid and Protocatechuic Acid Ethyl Ester Reaction media were prepared as described in example 1, Taxifolin being replaced by pyrocatechol (SIGMA, reference C 9510), by protocatechuic acid (ALDRICH, reference D10,980-0) or by protocatechuic acid ethyl ester (ALDRICH, reference E 2,485-9).

After 21 hours of incubation, a sample of each reaction medium was diluted 5 times with a solution containing methanol and water in the proportions of 40/60 and then analysed by HPLC (method 1).

The results are reported in the following table.

It is thus possible, according to the described method, to synthesize the new glucosylated derivatives of pyrocatechol, protocatechuic acid and protocatechuic acid ethyl ester; the resulting products are a family of substances containing at least monoglucosylated, diglucosylated, triglucosylated and tetraglucosylated derivatives.

Example 6

Enzymatic Synthesis of O-α-D-Glycosides of Caffeic Acid, 3,4-Dihydroxyhydrocinnamic Acid (Hydrocaffeic Acid) and Rosmarinic Acid Reaction media were prepared as described in example 1, Taxifolin being replaced by caffeic acid (SIGMA, reference C 0625), by 3,4-dihydroxyhydrocinnamic acid (ALDRICH, reference D10,980-0) or by rosmarinic acid (FLUKA, reference 44699; the concentration of rosmarinic acid in the reaction medium was 1 g/L).

After 21 hours of incubation, a sample of each reaction medium was diluted 5 times with a solution containing methanol and water in the proportions of 40/60 and then analysed by HPLC (method 1).

The results are reported in the following table.

| Glucosyl acceptor | Retention time, minutes | m/z [M − H] | Identification (theoretical molecular weight) |
|---|---|---|---|
| Pyrocatechol (chromatogram at 276 nm) | 13.78 | 108.74 | Pyrocatechol (110) |
| | 16.80 | 271.01 | Pyrocatechol monoglucoside (272) |
| | 14.88 | 433.05 | Pyrocatechol diglucoside (434) |
| | 13.22 | 595.06 | Pyrocatechol triglucoside (596) |
| | 11.87 | 919.35 | Pyrocatechol pentaglucoside (920) |
| Protocatechuic acid (chromatogram at 294 nm) | 11.26 | 152.88 | Protocatechuic acid (154) |
| | 8.25 | 315.05 | Protocatechuic acid monoglucoside (316) |
| | 7.89 | 477.00 | Protocatechuic acid diglucoside (478) |
| | 7.15 | 801.26 | Protocatechuic acid tetraglucoside (802) |
| Protocatechuic acid ethyl ester (chromatogram at 295 nm) | 28.28 | 180.96 | Protocatechuic acid ethyl ester (182) |
| | 27.30 | 343.02 | Protocatechuic acid ethyl ester monoglucoside (344) |
| | 24.99 | 505.05 | Protocatechuic acid ethyl ester diglucoside (506) |
| | 20.54 | 829.30 | Protocatechuic acid ethyl ester tetraglucoside (830) |

| Glucosyl acceptor | Retention time, minutes | m/z [M − H] | Identification (theroretical molecular weight) |
|---|---|---|---|
| Caffeic acid | 19.53 | 178.97 | Caffeic acid (180) |
| (chromatogram at 322 nm) | 15.46 | 341.09 | Caffeic acid monoglucoside (342) |
| | 14.62 | 503.16 | Caffeic acid diglucoside (504) |
| 3,4-dihydroxyhydrocinnamic acid (hydrocaffeic acid) (chromatogram at 278 nm) | 18.72 | 343.02 | Hydrocaffeic acid monoglucoside (344) |
| | 17.93 | 505.05 | Hydrocaffeic acid diglucoside (506) |
| | 17.80 | 180.96 | Hydrocaffeic acid (182) |
| | 17.50 | 343.02 | Hydrocaffeic acid monoglucoside (344) |
| | 17.06 | 667.21 | Hydrocaffeic acid triglucoside (668) |
| | 16.23 | 829.25 | Hydrocaffeic acid tetraglucoside (830) |
| | 16.01 | 505.05 | Hydrocaffeic acid diglucoside (506) |
| | 15.70 | 992.36 | Hydrocaffeic acid pentaglucoside (992) |
| | 14.70 | 667.21 | Hydrocaffeic acid triglucoside (668) |
| | 13.92 | 829.39 | Hydrocaffeic acid tetraglucoside (830) |
| | 13.22 | 991.50 | Hydrocaffeic acid pentaglucoside (992) |
| | 12.61 | 1153.60 | Hydrocaffeic acid hexaglucoside (1154) |
| | 12.08, 11.21 | # | Polymerization degree higher than 6 |
| Rosmarinic acid | 28.36 | 359.09 | Rosmarinic acid (360) |
| (chromatogram at 295 nm) | 27.18 | 521.16 | Rosmarinic acid monoglucoside (522) |

It is thus possible, according to the described method, to synthesize the new glucosylated derivatives of caffeic acid, hydrocaffeic acid and rosmarinic acid; the resulting products are a family of substances containing at least monoglycosylated, diglucosylated, triglucosylated and tetraglucosylated derivatives. As far as hydrocaffeic acid is concerned, it clearly appears that both hydroxyl groups have been substituted; indeed, at least two series of derivatives can be seen, both containing at least monoglucosylated (344), diglucosylated (506), triglucosylated (668), tetraglucosylated (830) and pentaglucosylated (992) derivatives. This shows that in some cases that cannot be predicted by a skilled man, both hydroxylated groups can accept a glucose moiety.

Example 7

Enzymatic Synthesis of O-α-D-Glycosides of 3,4-Dihydroxymandelic Acid, Esculetin and Esculin Reaction media were prepared as described in example 1, Taxifolin being replaced by 3,4-dihydroxymandelic acid (ALDRICH, reference 151610), or by esculetin (ALDRICH, reference 24,657-3) or by esculin (SIGMA, reference E 8250).

After 21 hours of incubation, a sample of each reaction medium was diluted 5 times with a solution containing methanol and water in the proportions of 40/60 and then analysed by HPLC (method 1).

The results are reported in the following table.

| Glucosyl acceptor | Retention time, minutes | m/z [M − H] | Identification (theroretical molecular weight) |
|---|---|---|---|
| 3,4-dihydroxymandelic acid (chromatogram at 322 nm) | 14.68 | 136.82 | Unknown |
| | 5.32 | 136/164 | unknown |
| | 4.10 | 182.95 | 3,4-Dihydroxymandelic acid (184) |
| | 3.45 | 341.03 | Unknown |
| | 2.79 | 341.03 | Unknown |
| | 2.49 | 140.80 | Unknown |
| Esculetin (chromatogram at 346 nm) | 18.36 | 176.91 | Esculetin (178) |
| | 15.65 | 339.03 | Esculetin monoglucoside (340) |
| | 14.74 | 501.06 | Esculetin diglucoside (502) |
| | 12.25 | 987.40 | Esculetin pentaglucoside (988) |
| | 11.686 | 1149.55 | Esculetin hexaglucoside (1150) |
| Esculin or esculetin 6-O-β-D-glucopyranoside (chromatogram at 343 nm) | 18.30 | 176.91 | Esculetin (178) |
| | 13.69 | 338.99 | Esculin or Esculetin 6-O-β-D-glucopyranoside |
| | 11.38 | 501.06 | Esculin monoglucoside (502) |
| | 10.73 | 663.15 | Esculin diglucoside (664) |
| | 9.38 | 1149.48 | Esculin tetraglucoside (1150) |

3,4-dihydroxymandelic acid contains a pyrocatechol structure as Taxifolin, pyrocatechol, protocatechuic acid, or caffeic acid; nevertheless, no glucosylated derivative of 3,4-dihydroxymandelic acid has been synthesized in the present conditions.

In an unexpected manner, the 6,7-dihydroxycoumarin skeleton is also a glucoside acceptor which leads to a series of glucosylated esculetin. It has to be underlined that the synthesized esculetin monoglucoside has a retention time of 15.65 minutes whereas the natural glucosylated esculetin (esculin or esculetin 6-O-β-D-glucopyranoside) has a retention time of 13.69 minutes; this has to be attributed to the fact that the osidic bond in the case of the natural molecule is of the α-type whereas the osidic bond in esculin is of the type-β.

In an unexpected manner, esculin is a glucoside acceptor, probably by its glucose moiety.

Example 8

Enzymatic Synthesis of O-α-D-Glycosides of Gallic Acid, Propyl Gallate and Epigallocatechin Gallate Reaction media were prepared as described in example 1, Taxifolin being replaced by gallic acid (FLUKA, reference 48630), by propyl gallate (SIGMA, reference P3130) or by epigallocatechin gallate (SIGMA, reference 44699) and the DMSO concentration being reduced to 15% v/v.

After 6 hours of incubation, a sample of each reaction medium was diluted 5 times with a solution containing methanol and water in the proportions of 40/60 and then analysed using the HPLC equipment previously described with a combination of eluant A (deionized water containing 1% v/v acetic acid) and eluant B (HPLC grade methanol containing 1% v/v acetic acid) as reported hereafter.

The results are reported in the following table.

| Glucosyl acceptor | Retention time, min Identification | Retention time, min Identification | Analysis conditions |
|---|---|---|---|
| Gallic acid | 7.92 Gallic acid | 10.40 Gallic acid O-α-glucoside | G6 |
|  | 5.95 Gallic acid | 6.75 Gallic acid O-α-glucoside | G1 |
| Propyl gallate | 27.22 Propyl gallate | 25.35 Propyl gallate O-α-glucoside | G1 |
| Epigallocatechin gallate | 17.03 Epigallocatechin gallate | 18.30 and 17.60 Epigallocatechin gallate O-α-glucoside and epigallocatechin gallate di-O-α-glucoside | G1 |

Analysis conditions:
G1: flow rate 1 ml/min; from 0 to 10 min: B increases linearly from 10 to 20%; from 10 to 25 min: B increases linearly from 20 to 50%; from 25 to 30 min: B is stable at 50%; from 30 to 35 min: B decreases linearly from 50 to 10%.
G6: flow rate 1 ml/min; from 0 to 20 min: B increases linearly from 2.5 to 25%; from 20 to 25 min: B is stable at 25%; from 25 to 28 min: B decreases linearly from 25 to 2.5%.

It is thus possible, according to the described method, to synthesize the new glucosylated derivatives of gallic acid, propyl gallate and epigallocatechin gallate; the resulting products are a family of substances containing at least a monoglucosylated derivative.

Example 9

Enzymatic Synthesis of O-α-D-Glycosides of Caffeic Acid Phenethyl Ester, Chlorogenic Acid and 3,4-Dihydroxybenzophenone Reaction media were prepared as described in example 1, Taxifolin being replaced by caffeic acid phenethyl ester (SIGMA, reference C8221), by chlorogenic acid (SIGMA, reference C3878) or by 3,4-dihydroxybenzophenone (ALDRICH, reference 579815) and the DMSO concentrations were 15% and 25% v/v.

After 6 hours of incubation, a sample of each reaction medium was diluted 5 times with a solution containing methanol and water in the proportions of 40/60 and then analysed using the HPLC equipment previously described with a combination of eluant A (deionized water containing 1% v/v acetic acid) and eluant B (HPLC grade methanol containing 1% v/v acetic acid) as reported hereafter.

The results are reported in the following table.

| Glucosyl acceptor (DMSO 15 and 25%) | Retention time, min Identification | Retention time, min Identification | Analysis conditions |
|---|---|---|---|
| Caffeic acid phenethyl ester | 20.15 Caffeic acid Phenethyl ester | 17.42 and 16.88: majority products 18.42, 15.65, 14.22 and 13.77 O-α-glucosides of caffeic acid phenethyl ester | G2 |

-continued

| Glucosyl acceptor (DMSO 15 and 25%) | Retention time, min Identification | Retention time, min Identification | Analysis conditions |
|---|---|---|---|
| Chlorogenic acid | 15.53 Chlorogenic acid | 11.00 and 10.67 Chlorogenic acid mono-O-α-glucoside and chlorogenic acid di-O-α-glucoside | G1 |
| 3,4-dihydroxybenzo-phenone | 32.35 3,4-dihydroxybenzo-phenone | 27.98 and 27.68 3,4-dihydroxybenzophenone O-α-glucoside and 3,4-dihydroxybenzophenone di-O-α-glucoside | G1 |

Analysis conditions:
G1: see example 8
G2: flow rate 1 ml/min; from 0 to 20 min: B increases linearly from 40 to 80%; from 20 to 22 min: B is stable at 80%; from 22 to 27 min: B decreases linearly from 80 to 40%.

It is thus possible, according to the described method, to synthesize the new glucosylated derivatives of caffeic acid phenethyl ester, chlorogenic acid and 3,4-dihydroxybenzo-phenone; the resulting products are a family of substances containing at least a monoglucosylated derivative.

Example 10

Enzymatic Synthesis of O-α-D-Glycosides of Catechin, Eriodictyol, Fisetin, Oleuropein and Nordihydroguaiaretic Acid Reaction media were prepared as described in example 1, Taxifolin being replaced by catechin (FLUKA, reference 22110), by eriodictyol (EXTRASYNTHESE, reference 0056), by fisetin (SIGMA, reference F4043), by oleuropein (EXTRASYNTHESE, reference 0204) or by nordihydroguaiaretic acid (EXTRASYNTHESE, reference 6135) and the DMSO concentrations were 15% and 25% v/v.

After 6 hours of incubation, a sample of each reaction medium was diluted 5 times with a solution containing methanol and water in the proportions of 40/60 and then analysed using the HPLC equipment previously described with a combination of eluant A (deionized water containing 1% v/v acetic acid) and eluant B (HPLC grade methanol containing 1% v/v acetic acid) as reported hereafter.

The results are reported in the following table.

| Glucosyl acceptor (DMSO 15 and 25%) | Retention time, min Identification | Retention time, min Identification | Analysis conditions |
|---|---|---|---|
| Catechin | 14.07 | 12.60 Catechin O-α-glucoside | G1 |
| Eriodictyol | 30.10 Eriodictyol | 27.18 and 26.90 Eriodictyol O-α-glucoside and eriodictyol di-O-α-glucoside | G1 |
| Fisetin | 29.37 Fisetin | 26.05 Fisetin O-α-glucoside | G1 |
| Oleuropein | 28.28 Oleuropein | 26.45 and 24.68 Oleuropein O-α-glucoside and oleuropein di-O-α-glucoside | G1 |
| Nordihydroguaia-retic acid | 18.53 Nordihydroguaia-retic acid | 16.97 and 16.40: majority products 15.53 O-α-glucosides of nordihydroguaiaretic acid | G2 |

Analysis conditions:
G1: see example 8
G2: see example 9

It is thus possible, according to the described method, to synthesize the new glucosylated derivatives of catechin, eriodictyol, fisetin, oleuropein and nordihydroguaiaretic acid; the resulting products are a family of substances containing at least a monoglucosylated derivative.

Example 11

Enzymatic Synthesis of O-α-D-Glycosides of Catechin, 3,4-Dihydroxybenzoic Acid, Gallic Acid, Rosmarinic Acid, Caffeic Acid and Chlorogenic Acid in Strictly Aqueous Media Reaction media were prepared as described in example 1, Taxifolin being replaced by catechin (FLUKA, reference 22110) at a concentration of 7.5 g/L, by 3,4-dihydroxybenzoic acid (ALDRICH, reference D10,980-0) at a concentration of 9.0 g/L, by gallic acid (FLUKA, reference 48630) at a concentration of 9.0 g/L, by rosmarinic acid (FLUKA, reference 44699) at a concentration of 7.5 g/L, by caffeic acid (SIGMA, reference C0625) at a concentration of 9.0 g/L or by chlorogenic acid (SIGMA, reference C3878) at a concentration of 7.5 g/L. The DMSO was omitted whereas the sodium acetate buffer concentration was increased to 100 mM and the enzyme activity was reduced to 1.0 U/ml.

After 6 hours of incubation, a sample of each reaction medium was diluted 5 times with a solution containing methanol and water in the proportions of 40/60 and then analysed using the HPLC equipment previously described with a combination of eluant A (deionized water containing 1% v/v acetic acid) and eluant B (HPLC grade methanol containing 1% v/v acetic acid) as reported hereafter.

The results are reported in the following table.

| Glucosyl acceptor | Retention time, min Identification | Retention time, min Identification | Analysis conditions |
|---|---|---|---|
| Catechin | 13.57 Catechin | 12.57 Catechin O-α-glucoside | G1 |
| Gallic acid | 5.95 Gallic acid | 6.75 Gallic acid O-α-glucoside | G1 |
| Caffeic acid | 18.62 Caffeic acid | 14.27 caffeic acid O-α-glucoside | G1 |
| 3,4-dihydroxybenzoic acid | 10.58 3,4-dihydroxybenzoic acid | 6.83 3,4-dihydroxybenzoic acid O-α-glucoside | G1 |
| Rosmarinic acid | 27.65 Rosmarinic acid | 26.42, 25.15 and 24.33 O-α-glucosides of rosmarinic acid | G1 |
| Chlorogenic acid | 15.63 Chlorogenic acid | 10.95 Chlorogenic acid O-α-glucoside | G1 |

Analysis conditions:
G1: see example 8

It is thus possible, according to the described method, to synthesize the new glucosylated derivatives of catechin, gallic acid, caffeic acid, 3,4-dihydroxybenzoic acid, rosmarinic acid and chlorogenic acid in the absence of organic solvent; the resulting products are a family of substances containing at least a monoglucosylated derivative.

Example 12

Attempt for the Enzymatic Synthesis of O-α-D-Glycosides of Ellagic Acid, Alizarin, Epinephrine, Rutin and Baicalein Reaction media were prepared as described in example 1, Taxifolin being replaced by ellagic acid (FLUKA, reference 45140), by rutin (SIGMA, reference R5143), by alizarin (EXTRASYNTHESE, reference 0411), by epinephrine (SIGMA, reference E4250) or by baicalein (FLUKA, reference 11712). The DMSO concentration was 25% v/v.

After 6 hours and 21 hours of incubation, a sample of each reaction medium was diluted 5 times with a solution containing methanol and water in the proportions of 40/60 and then analysed using the HPLC equipment previously described with a combination of eluant A (deionized water containing 1% v/v acetic acid) and eluant B (HPLC grade methanol containing 1% v/v acetic acid) as reported hereafter.

The results are reported in the following table.

| Glucosyl acceptor | Retention time, min Identification | Retention time, min Identification | Analysis conditions |
|---|---|---|---|
| Ellagic acid | 27.42 Ellagic acid | No other pic and thus no O-α-glucoside of ellagic acid | G1 |
| Rutin | 26.33 Rutin | No other pic and thus no O-α-glucoside of ellagic acid | G1 |
| Alizarin | 19.17 Alizarin | No other pic and thus no O-α-glucoside of ellagic acid | G2 |
| Epinephrine | 5.96 Epinephrine | No other pic and thus no O-α-glucoside of ellagic acid | G6 |
| Baicalein | 11.60 Baicalein | No other pic and thus no O-α-glucoside of ellagic acid | G4 |

Analysis conditions:
G1: see example 8
G2: see example 9
G6: see example 8
G4: flow rate 1 ml/min; from 0 to 10 min: B increases linearly from 40 to 80%; from 10 to 15 min: B is stable at 80%; from 15 to 20 min: B decreases linearly from 80 to 40%.

Though the tested substances contain a pyrocatechol structure the substituents of the ring do not allow their recognition by the enzyme. In the case of rutin, the saccharide part of quercetin 3-O-rutinoside appears to be very important for the enzyme recognition since quercetin is glucosylated in the 3' and/or 4' position (BERTRAND et al.) whereas rutin is not.

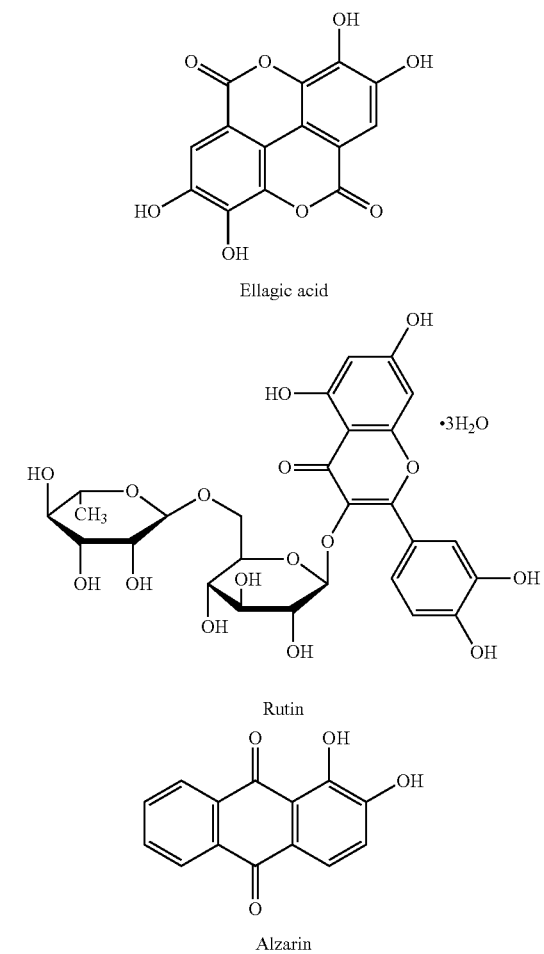

Ellagic acid

Rutin

Alzarin

-continued

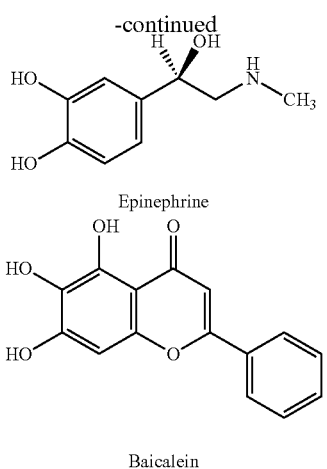

Epinephrine

Baicalein

We claim:
1. A method for producing a phenolic compound O-α-glucoside comprising incubating sucrose and a glucansucrase EC 2.4.1.5 from *Leuconostoc* species with a phenolic compound selected from catechin gallate, epicatechin gallate, gallocatechin gallate, hamamelitannin (2',5-di-O-galloyl-hamamelose), rosmarinic acid, esculetin, 4-methylesculetin, nordalbergin (6,7-dihydroxyphenylcoumarin), chlorogenic acid, chicoric acid (dicaffeoyl tartaric acid), echinacoside (2-(3,4-dihydroxyphenyl)ethyl O-6-deoxy-alpha-1-mannopyranosyl-(1→3)-O-(beta-D-glucopyranosyl-(1→6))-, 4-(3-(3,4-dihydroxyphenyl)-2-propenoate), beta-d-glucopyranoside), verbascoside and a phenolic compound having the following formula:

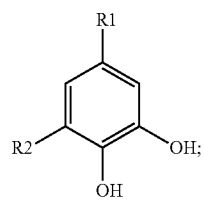    (I)

wherein
R2 is H or OH; and
R1 is selected from the group consisting of

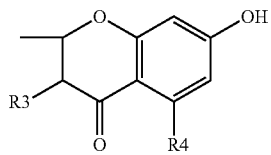

wherein R3 and R4, independently, are H or OH, with the proviso that at least one among R3 and R4 represents OH;

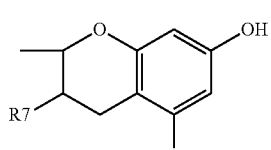

wherein R7 is selected from the group consisting of H, or —OH and R8 is H or OH, with the proviso that at least one among R7 and R8 represents OH;

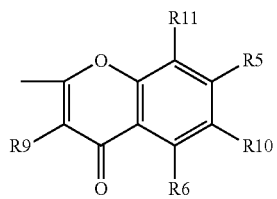

wherein R5 is OH or OCH$_3$; R6 is H or OH, R9 is H or OH, R10 is H, OCH$_3$ or C$_6$H$_{11}$O$_3$, and R11 is H, OH or C$_6$H$_{11}$O$_5$, with the proviso that R10 and R11 cannot be both H when R5 and R6 are both OH and that when R10 is C$_6$H$_{11}$O$_5$ then R11 is H;
—(CH$_2$)$_n$—COOR or —(CH$_2$)$_n$—CONHR, with n being an integer from 0 to 2;
—(CR12═CH)—COOR or —(CR12═CH)—CONHR, R12 being H or a C$_1$-C$_6$ linear or cyclic alkyl or alkenyl;
—(CH$_2$)$_n$—COR or —(CH═CH)$_n$—COR with n being an integer from 0 to 2;
—H;

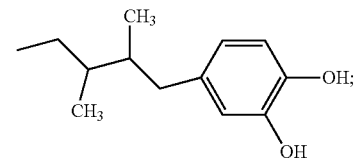

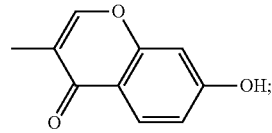

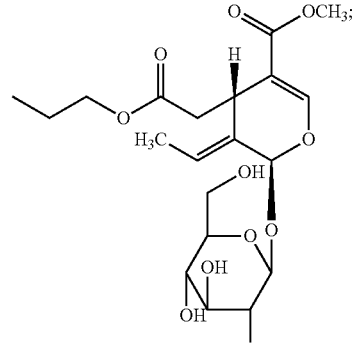

and

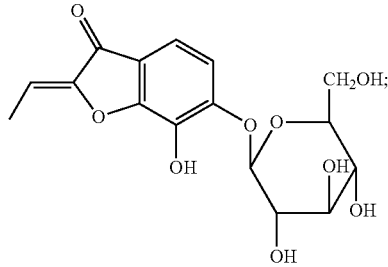

and
a C$_1$-C$_{10}$ hydrocarbon group which forms with the represented ring of formula (I) a fused ring (bi or tricyclic)

together with the ortho carbon of R1, said ring being optionally interrupted by at least one heteroatom;

wherein R is H or a linear, branched, or cyclic, aromatic or not, saturated or unsaturated, $C_1$-$C_{10}$ hydrocarbon group, optionally interrupted by at least one heteroatom, wherein said hydrocarbon group comprises an alkyl, an alkenyl, or an alkynyl, which can be substituted by one or several substituents selected from the group consisting of: an ($C_5$-$C_9$)aryl, a ($C_4$-$C_9$)heterocycle, an ($C_1$-$C_3$)alkoxy, an ($C_2$-$C_3$)acyl, an ($C_1$-$C_3$) alcohol, a carboxylic group (—COOH), an ($C_2$-$C_3$) ester, an ($C_1$-$C_3$)amine, an amino group (—NH$_2$), an amide (—CONH$_2$), an ($C_1$-$C_3$)imine, a nitrile, a hydroxyl (—OH), an aldehyde group (—CHO), a halogen, a ($C_1$-$C_3$)halogenoalkyl, a thiol (—SH), a ($C_1$-$C_3$) thioalkyl, a ($C_1$-$C_3$)sulfone, a ($C_1$-$C_3$)sulfoxide, and a combination thereof.

2. The method according to claim 1, wherein:
a) R1 of the phenolic compound is

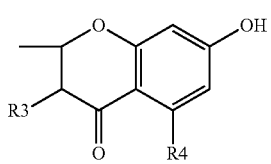

wherein R3 and R4, independently, are H or OH, with the proviso that at least one among R3 and R4 represents OH; or
b) R1 of the phenolic compound is

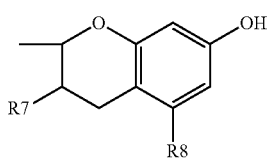

wherein R7 is selected from the group consisting of H, or —OH and R8 is H or OH, with the proviso that at least one among R7 and R8 represents OH; or
c) R1 of the phenolic compound is

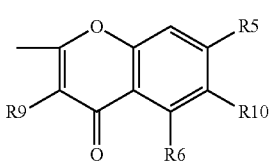

wherein R5 is OH or OCH$_3$; R6 is H or OH, R9 is H or OH, R10 is H, OCH$_3$ or $C_6H_{11}O_5$, and R11 is H, OH or $C_6H_{11}O_5$, with the proviso that R10 and R11 cannot be both H when R5 and R6 are both OH and that when R10 is $C_6H_{11}O_5$ then R11 is H; or
d) R1 of the phenolic compound is —(CH$_2$)$_n$—COOR or —(CH$_2$)$_n$—CONHR with n being an integer from 0 to 2; or
e) R1 of the phenolic compound is —(CR12=CH)— COOR or —(CR12=CH)—CONHR, R12 being H or a $C_1$-$C_6$ linear, branched or cyclic alkyl or alkenyl; or
f) R1 of the phenolic compound is —(CH$_2$)$_n$—COR or —(CH=CH)$_n$—COR with n being an integer from 0 to 2; or g) R1 of the phenolic compound is H; or
h) R1 of the phenolic compound is

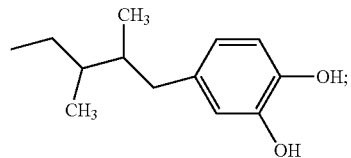

or
i) R1 of the phenolic compound is

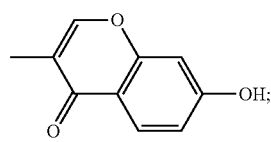

or
j) R1 of the phenolic compound is

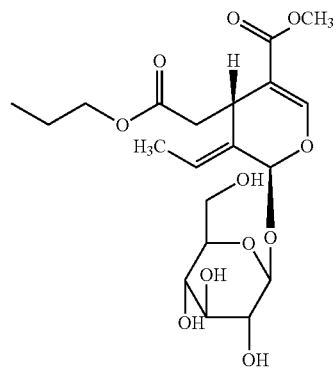

or
k) R1 of the phenolic compound is

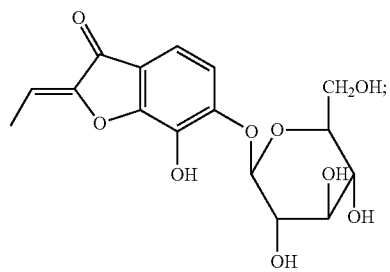

or
l) R1 of the phenolic compound is a $C_1$-$C_{10}$ hydrocarbon group which forms with the represented ring of formula (I) a fused ring (bi or tricyclic) together with the ortho carbon of R1, said ring being optionally interrupted by at least one heteroatom; or
m) phenolic compound is selected from the group consisting of

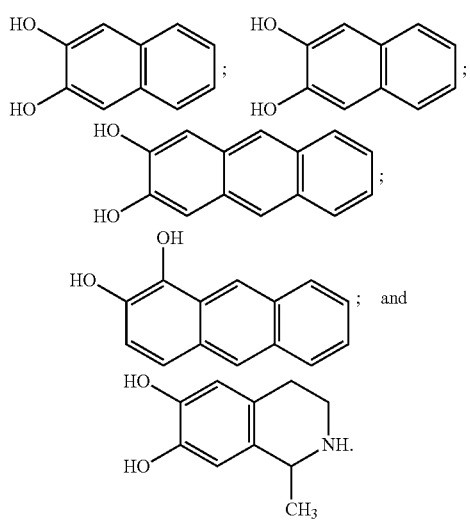

3. The method according to claim 2, wherein the phenolic compound is selected from the group consisting of the taxifolin, the eriodictyol, the dihydrorobinetin and the fustin.

4. The method according to claim 1, wherein the phenolic compound is selected in the group consisting of catechin, epicatechin, catechin gallate, epicatechin gallate, gallocatechin, epigallocatechin, and gallocatechin gallate.

5. The method according to claim 2, wherein the phenolic compound is selected from the group consisting of rhamnetin, fisetin, robinetin, gossypetin, orientin, homoorientin and cirsiliol.

6. The method according to claim 1, wherein the phenolic compound is selected from the group consisting of homoprotocatechuic acid, dihydrocaffeic acid, protocatechuic acid ethyl ester, propyl gallate, gallic acid, hamamelitannin (2',5-di-O-galloyl-hamamelose) and protocatechuic acid.

7. The method according to claim 1, wherein the phenolic compound is selected from the group consisting of caffeic acid, rosmarinic acid, esculetin, 4-methylesculetin, nordalbergin (6,7-dihydroxyphenylcoumarin), chlorogenic acid, caffeic acid phenethyl ester, chicoric acid (dicaffeoyl tartaric acid), echinacoside (2-(3,4-dihydroxyphenyl)ethyl O-6-deoxy-alpha-1-mannopyranosyl-(1→3)-O-(beta-D-glucopyranosyl-(1→6))-, 4-(3-(3,4-dihydroxyphenyl)-2-propenoate), beta-d-glucopyranoside) and verbascoside.

8. The method according to claim 2, wherein the phenolic compound is selected from the group consisting of maclurine, 3,4-dihydroxybenzaldehyde, 3,4-dihydroxybenzophenone, butein (2',3,4,4'-tetrahydroxychalcone), 3,4-dihydroxyacetophenone, marein (2',3,3',4,4'-pentahydroxy-4'-glucosylchalcone), and eriodictyolchalcone (2',4',6',3,4-pentahydroxychalcone).

9. The method according to claim 1, wherein the reaction is conducted in a water/co-solvent mixture comprising water and dimethyl sulfoxide (DMSO), and wherein DMSO concentration ranges from 15% to 25% (v/v).

10. The method according to claim 6, wherein the phenolic compound O-α-glucoside is glycosylated at the para position with respect to the carbon to which the R1 group is attached.

11. The method according to claim 2, wherein the phenolic compound is gallic acid.

12. The method according to claim 11, wherein gallic acid is glycosylated at the para position with respect to the carbon to which the carboxyl group is attached.

13. The method according to claim 9, wherein the phenolic compound is taxifolin.

14. The method according to claim 1, wherein the glucansucrase EC 2.4.1.5 from *Leuconostoc* species is from *Leuconostoc mesenteroides* NRRL B-512F.

15. The method according to claim 9, wherein water/co-solvent mixture has a pH ranging from 5 to 7.

16. The method according to claim 9, wherein DMSO concentration in said water/co-solvent mixture is 15%+/−3%.

17. The method according to claim 9, wherein DMSO concentration in said water/co-solvent mixture is 15%+/−3% and the water/co-solvent mixture has a pH of 5.2.

18. The method according to claim 1, wherein the method comprises incubating a mixture of acetate buffer at 10 mM to 100 mM, DMSO at 10% to 35% (volume/volume), sucrose at 100 mM to 900 mM, phenolic compound at 2 to 200 mM, calcium salts at 0.5 mg to 1 g/l and said glucansucrase EC 2.4.1.5 at a final concentration of 0.5 to 5 U/ml at 30° C. to form said phenolic compound O-α-glucoside.

* * * * *

UNITED STATES PATENT AND TRADEMARK OFFICE
CERTIFICATE OF CORRECTION

PATENT NO. : 9,828,407 B2
APPLICATION NO. : 14/084793
DATED : November 28, 2017
INVENTOR(S) : Daniel Auriol et al.

It is certified that error appears in the above-identified patent and that said Letters Patent is hereby corrected as shown below:

In the Specification

Column 12,
Line 24, "cis-glucoside glucosidase)" should read --cis-glucoside (β-glucosidase)--.

Column 33,

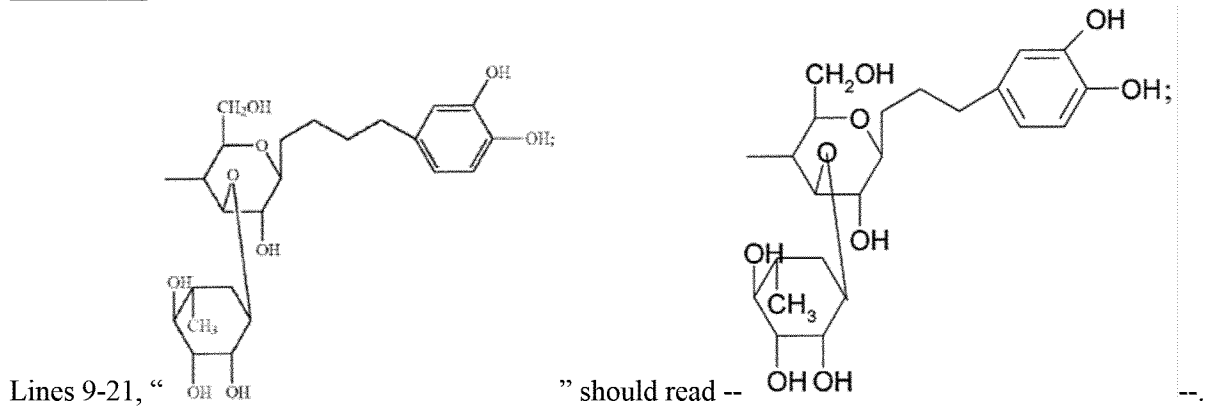

Lines 9-21, " " should read -- --.

Column 38,
Line 53, "1 g/l'" should read --1 g/l--.

Column 45,
Line 45, "OCH3" should read --OCH$_3$--.
Line 46, "OCH3" should read --OCH$_3$--.
Line 47, "OCH3" should read --OCH$_3$--.
Line 48, "OCH3" should read --OCH$_3$--.
Line 49, "OCH3" should read --OCH$_3$--.
Line 50, "OCH3" should read --OCH$_3$--.

Signed and Sealed this
Thirteenth Day of November, 2018

Andrei Iancu
*Director of the United States Patent and Trademark Office*

CERTIFICATE OF CORRECTION (continued)
U.S. Pat. No. 9,828,407 B2

Column 48,

Lines 1-15, " 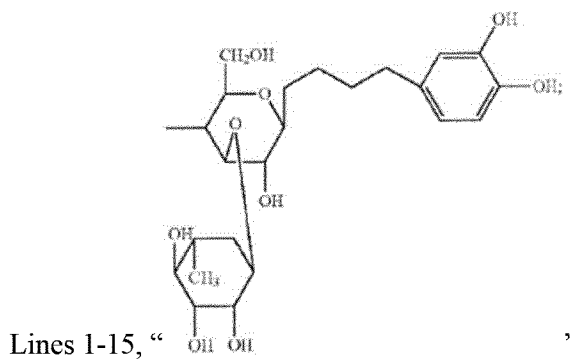 " should read -- 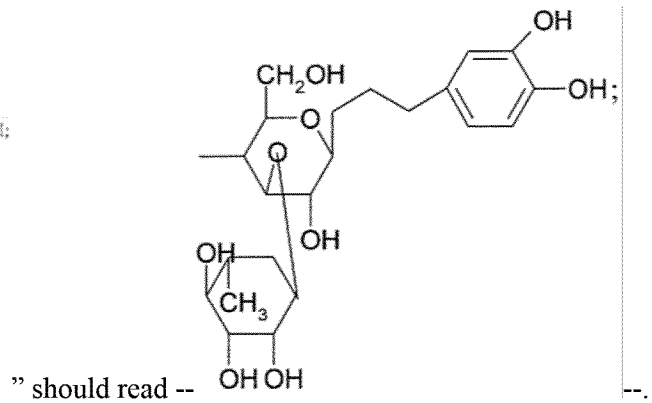 --.

Column 72,
Line 67, "Alzarin" should read --Alizarin--.

In the Claims

Column 73,
Lines 30-32, "O-6-deoxy-alpha-l-mannopyranosyl-(1→3)-O-(beta-D-glucopyranosyl-(1→6))-," should read --*O*-6-deoxy-alpha-l-mannopyranosyl-(1→3)-*O*-(beta-D-glucopyranosyl-(1→6))-,--.

Column 74,
Line 15, "or $C_6H_{11}O_3$," should read --or $C_6H_{11}O_5$,--.

Column 78,
Lines 1-2, "O-6-deoxy-alpha-l-mannopyranosyl-(1→3)-O-(beta-D-glucopyranosyl-(1→6))-," should read --*O*-6-deoxy-alpha-l-mannopyranosyl-(1→3)-*O*-(beta-D-glucopyranosyl-(1→6))-,--.